United States Patent
Callol et al.

(10) Patent No.: US 8,337,540 B2
(45) Date of Patent: Dec. 25, 2012

(54) STENT FOR TREATING BIFURCATIONS AND METHOD OF USE

(75) Inventors: Joseph R. Callol, San Francisco, CA (US); W. Stan Wilson, Missoula, MO (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 457 days.

(21) Appl. No.: 10/022,996

(22) Filed: Dec. 17, 2001

(65) Prior Publication Data

US 2003/0125802 A1 Jul. 3, 2003

Related U.S. Application Data

(63) Continuation-in-part of application No. 09/861,473, filed on May 17, 2001, now Pat. No. 6,749,628.

(51) Int. Cl.
*A61F 2/84* (2006.01)

(52) U.S. Cl. .................................................. 623/1.11

(58) Field of Classification Search ............... 623/1.11, 623/1.23, 1.35, 1.37, 1.15, 1.16
See application file for complete search history.

(56) References Cited

U.S. PATENT DOCUMENTS

| | | | | |
|---|---|---|---|---|
| 5,591,222 | A | * | 1/1997 | Susawa et al. ............ 606/195 |
| 5,607,444 | A | | 3/1997 | Lam |
| 5,632,762 | A | | 5/1997 | Myler |
| 6,099,497 | A | * | 8/2000 | Adams et al. ............ 604/96.01 |
| 6,129,738 | A | * | 10/2000 | Lashinski et al. ........... 606/194 |
| 6,129,754 | A | | 10/2000 | Kanesaka et al. |
| 6,165,195 | A | | 12/2000 | Wilson et al. |
| 6,183,509 | B1 | | 2/2001 | Dibie |
| 6,187,036 | B1 | | 2/2001 | Shaolian et al. |
| 6,210,429 | B1 | | 4/2001 | Vardi et al. |
| 6,221,098 | B1 | | 4/2001 | Wilson et al. |
| 6,254,593 | B1 | | 7/2001 | Wilson |
| 6,258,116 | B1 | | 7/2001 | Hojeibane |
| 6,264,682 | B1 | | 7/2001 | Wilson et al. |
| 6,270,524 | B1 | * | 8/2001 | Kim ........................... 623/1.15 |
| 6,346,089 | B1 | | 2/2002 | Dibie |
| 6,652,578 | B2 | * | 11/2003 | Bailey et al. ............... 623/1.24 |

(Continued)

FOREIGN PATENT DOCUMENTS

EP 0740928 A2 11/1996
(Continued)

OTHER PUBLICATIONS

Communication Pursuant to Article 94(3) EPC dated Apr. 23, 2010.

*Primary Examiner* — Ryan Severson
(74) *Attorney, Agent, or Firm* — Fulwider Patton LLP

(57) ABSTRACT

An improved stent design and stent delivery catheter assembly for repairing a main vessel proximal to a side branch vessel and the opening to the side branch vessel forming a bifurcation. The stent is particularly useful in treating a bifurcation where plaque is present proximal to the side branch vessel but not distal to the side branch vessel. The present invention includes a trap door stent design, a stent delivery catheter assembly, and the method for delivering and implanting the stent in a bifurcated vessel. More particularly, the invention relates to a stent having rings aligned along a common longitudinal axis and connected by links. The stent has first rings that are implanted in the main vessel proximal to the bifurcation and one or more second rings forming a trap door section to appose the opening to the side branch vessel and the main vessel.

6 Claims, 39 Drawing Sheets

U.S. PATENT DOCUMENTS

| | | |
|---|---|---|
| 2001/0010013 A1 | 7/2001 | Cox et al. |
| 2001/0037137 A1 | 11/2001 | Vardi et al. |
| 2001/0049548 A1 | 12/2001 | Vardi et al. |
| 2001/0056297 A1 | 12/2001 | Hojeibane |
| 2002/0035389 A1 | 3/2002 | Richter et al. |
| 2002/0042650 A1 | 4/2002 | Vardi et al. |
| 2003/0144724 A1 | 7/2003 | Murray |
| 2003/0181969 A1 | 9/2003 | Kugler |
| 2004/0186508 A1 | 9/2004 | Adams et al. |

FOREIGN PATENT DOCUMENTS

| | | |
|---|---|---|
| EP | 0812928 A1 | 6/1997 |
| EP | 0 857 471 A2 | 8/1998 |
| EP | 0857471 A2 | 8/1998 |
| JP | 11-319113 | 11/1999 |
| JP | 2000-511444 | 9/2000 |
| WO | WO 96/34580 * | 11/1996 |
| WO | WO 00/27463 * | 5/2000 |
| WO | 0071055 A1 | 11/2000 |
| WO | 0121095 A2 | 3/2001 |
| WO | WO 01/52769 A1 | 7/2001 |
| WO | WO 02/091951 A2 | 11/2002 |
| WO | 2003051234 A1 | 6/2003 |
| WO | WO 03/051234 A1 | 6/2003 |
| WO | 2005/009295 A1 | 2/2005 |

\* cited by examiner

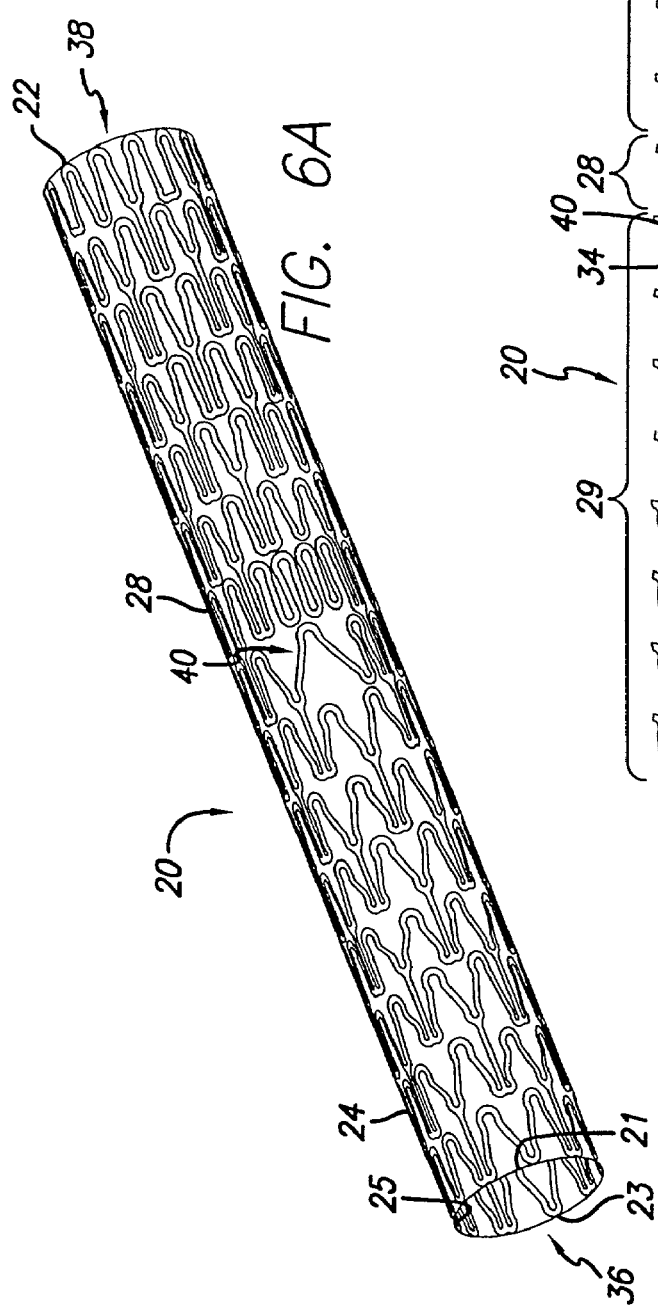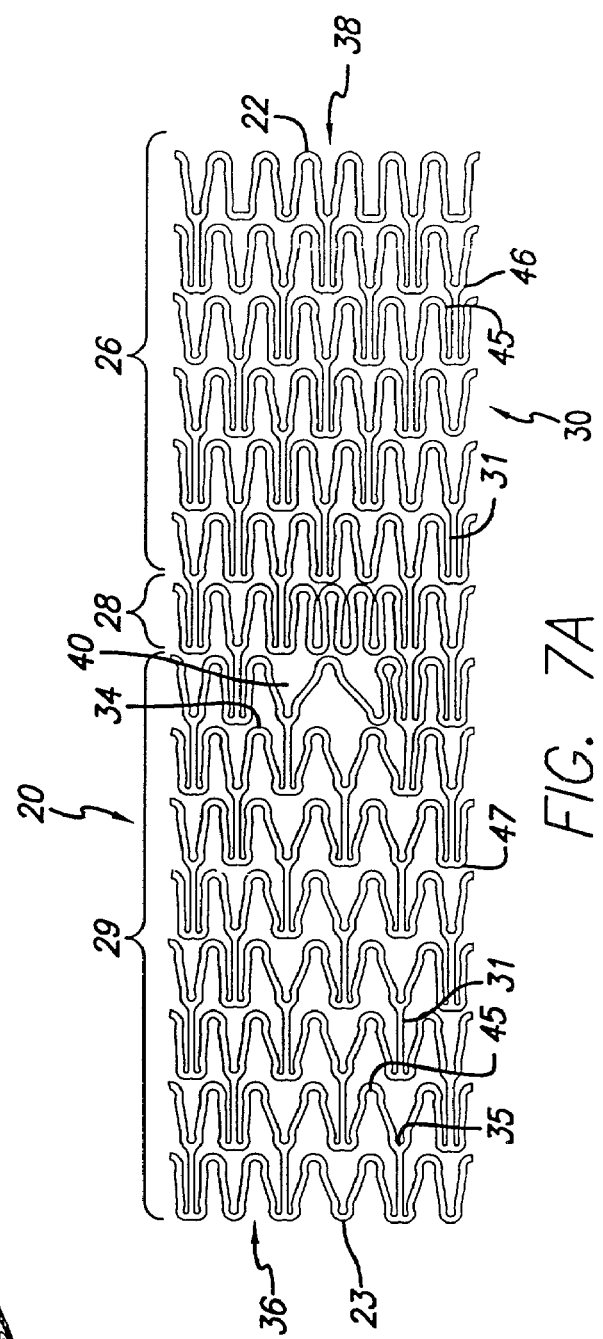

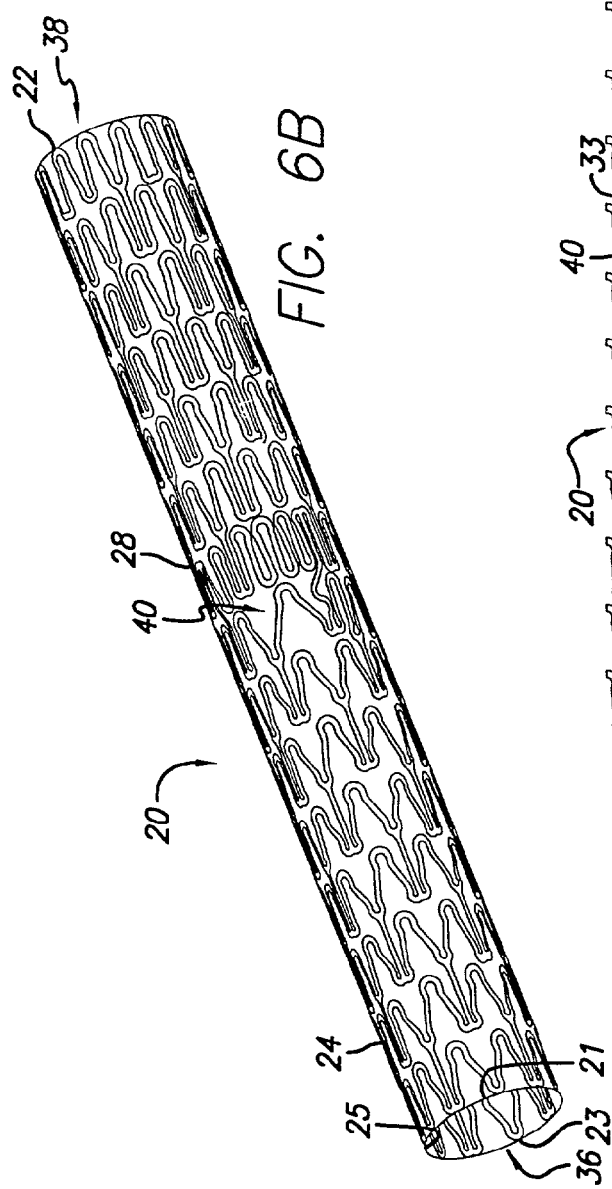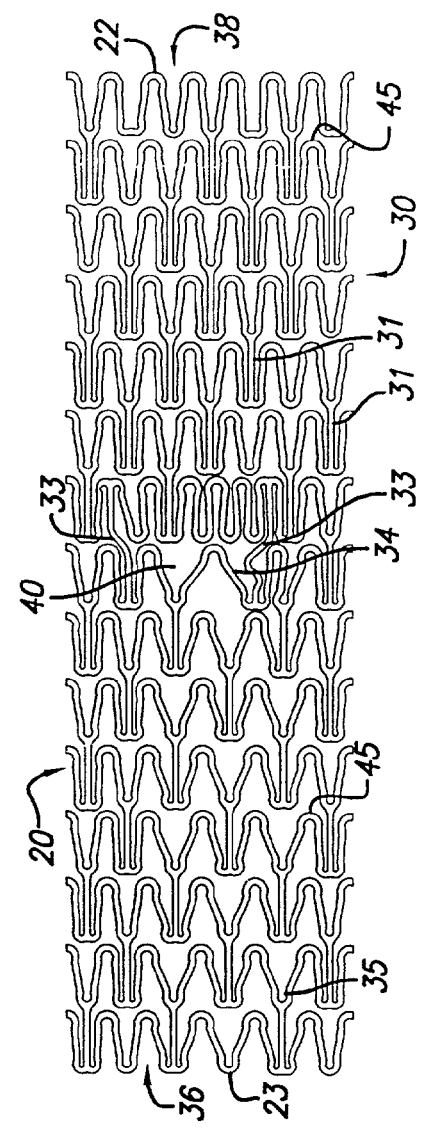

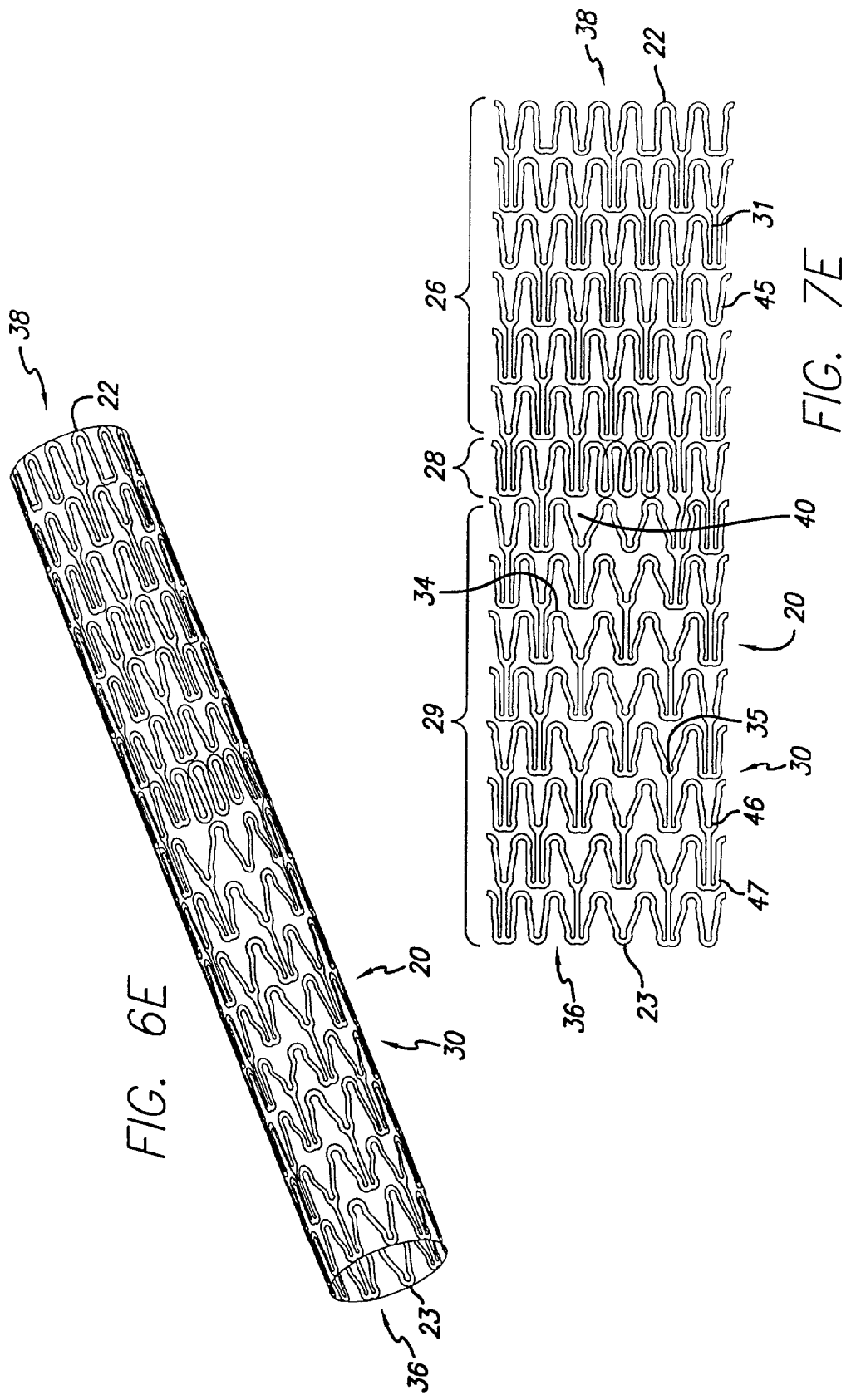

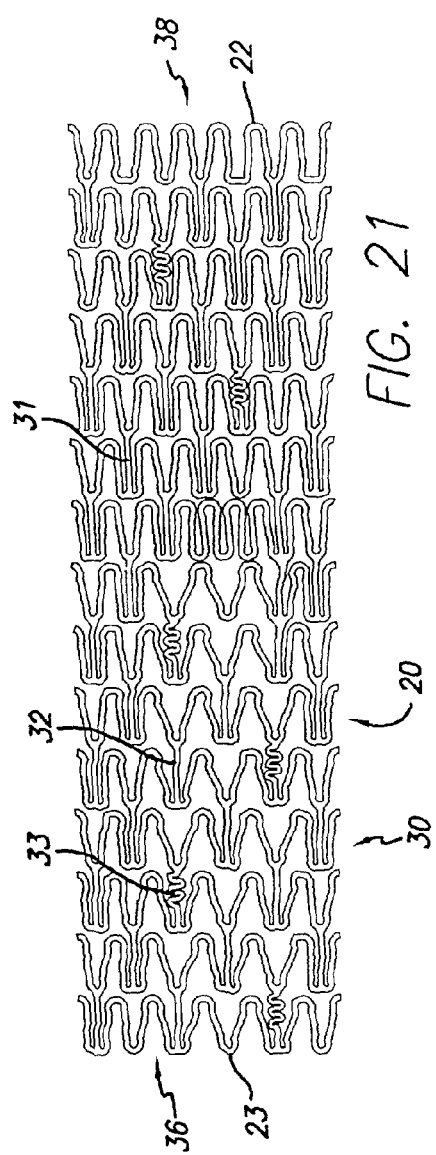
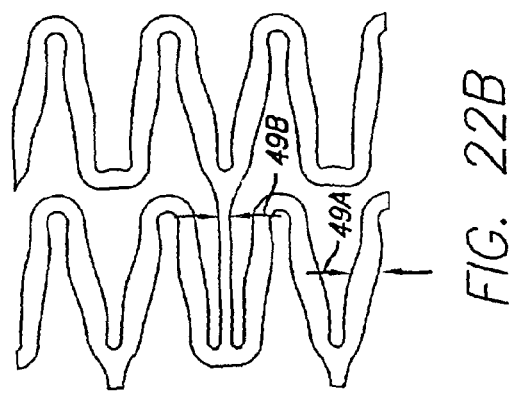
FIG. 21
FIG. 22B

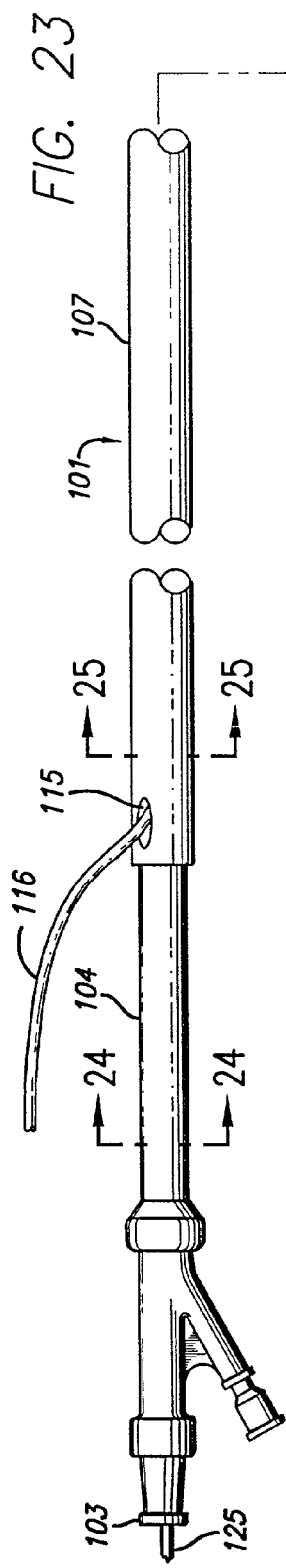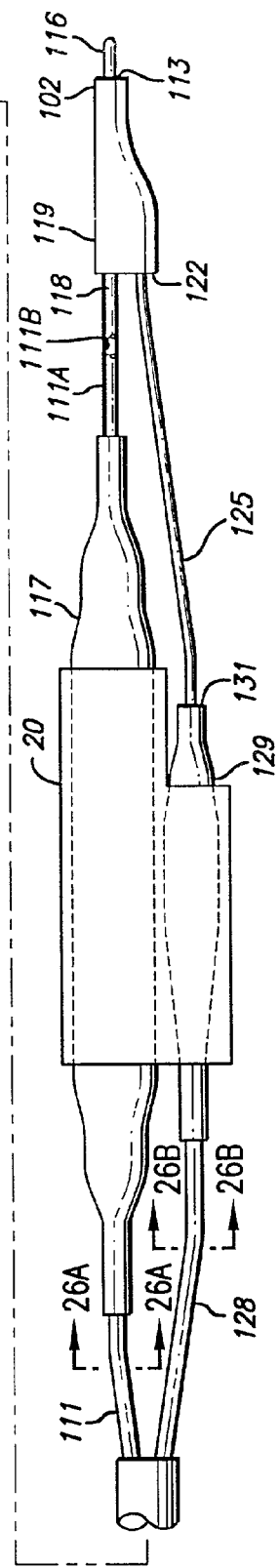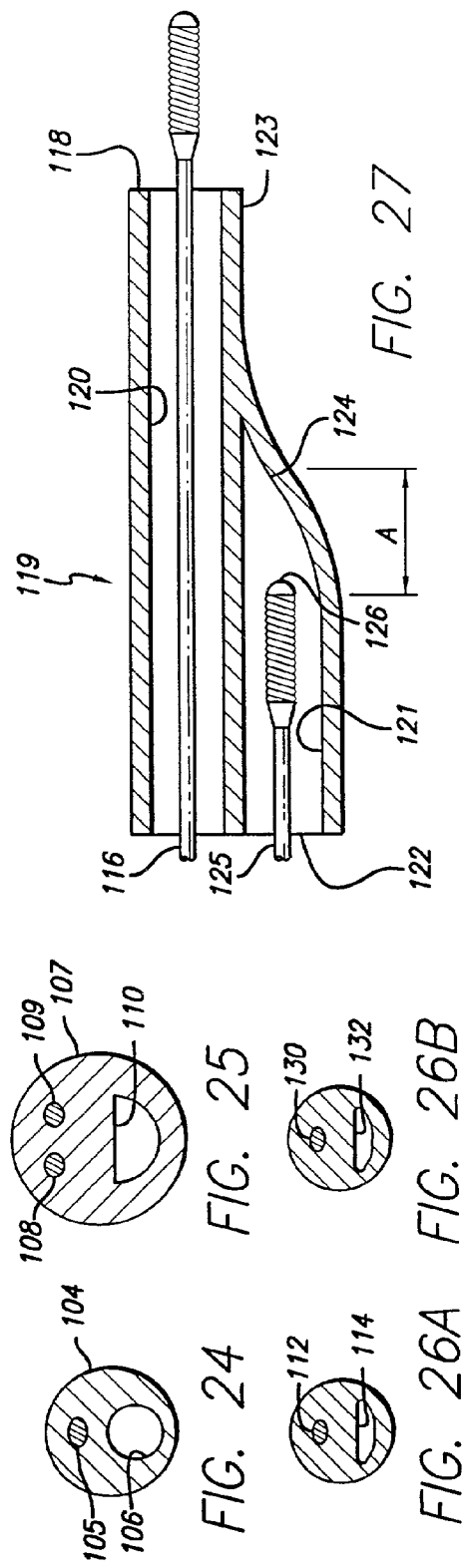

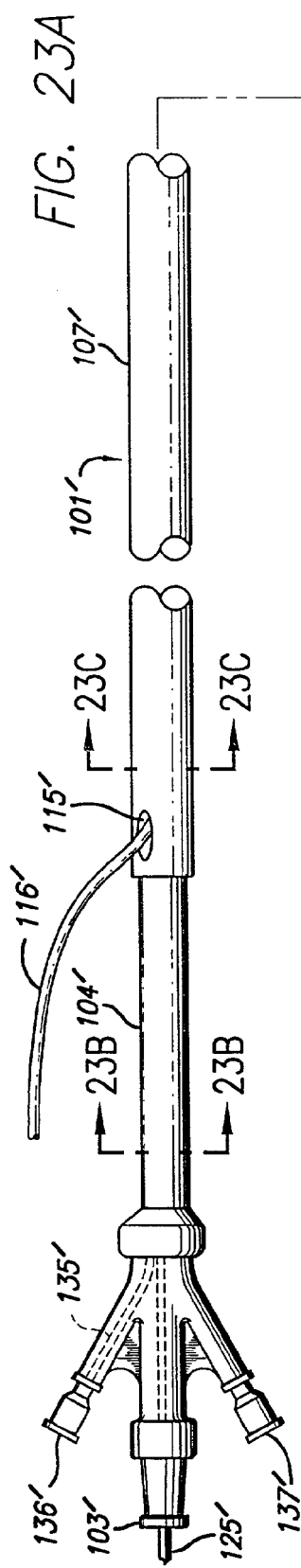
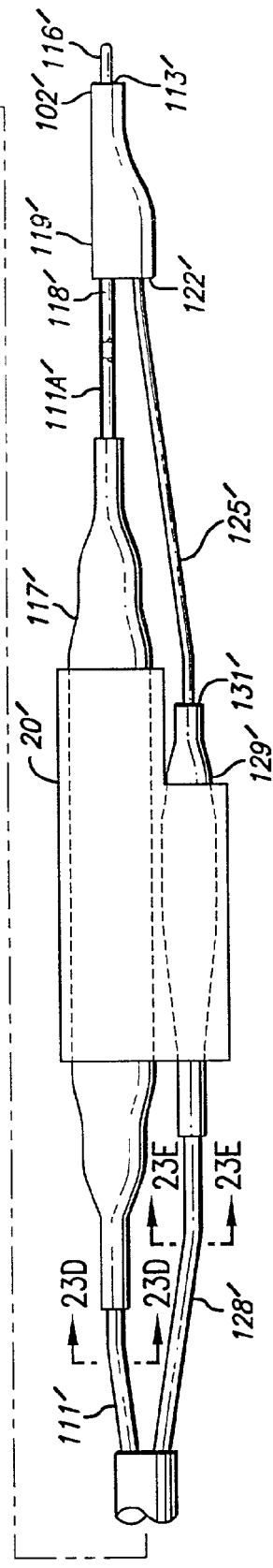
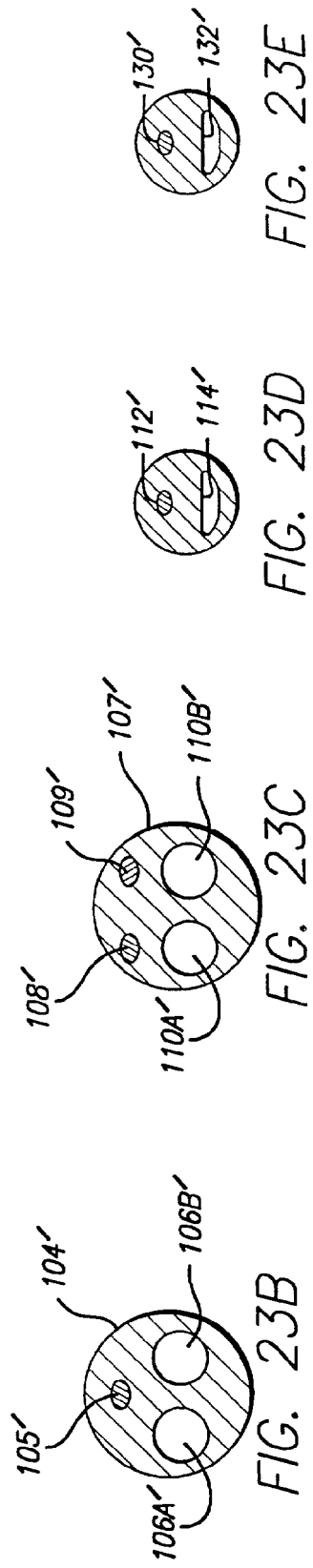
FIG. 23A
FIG. 23B
FIG. 23C
FIG. 23D
FIG. 23E

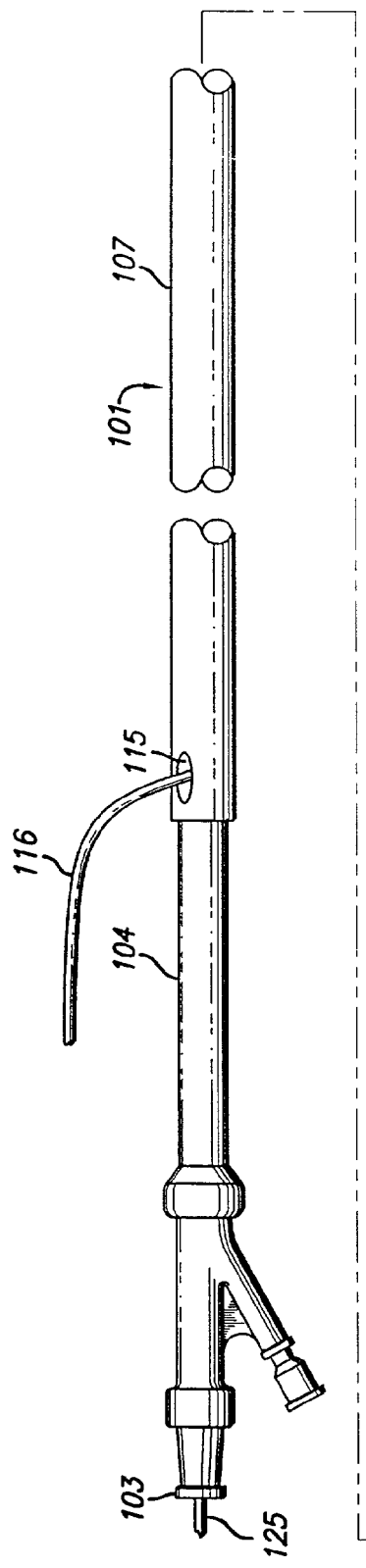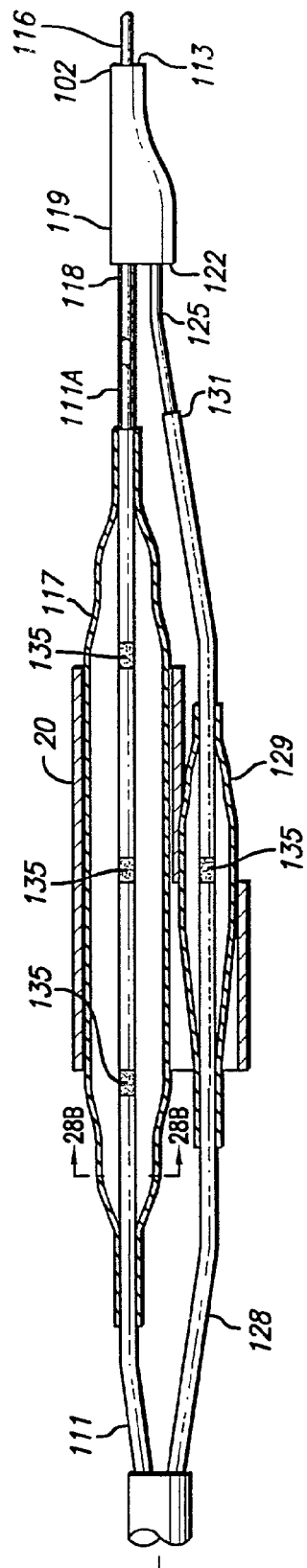
FIG. 28A
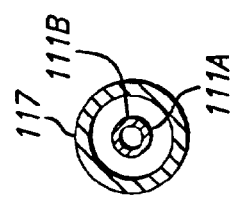
FIG. 28B

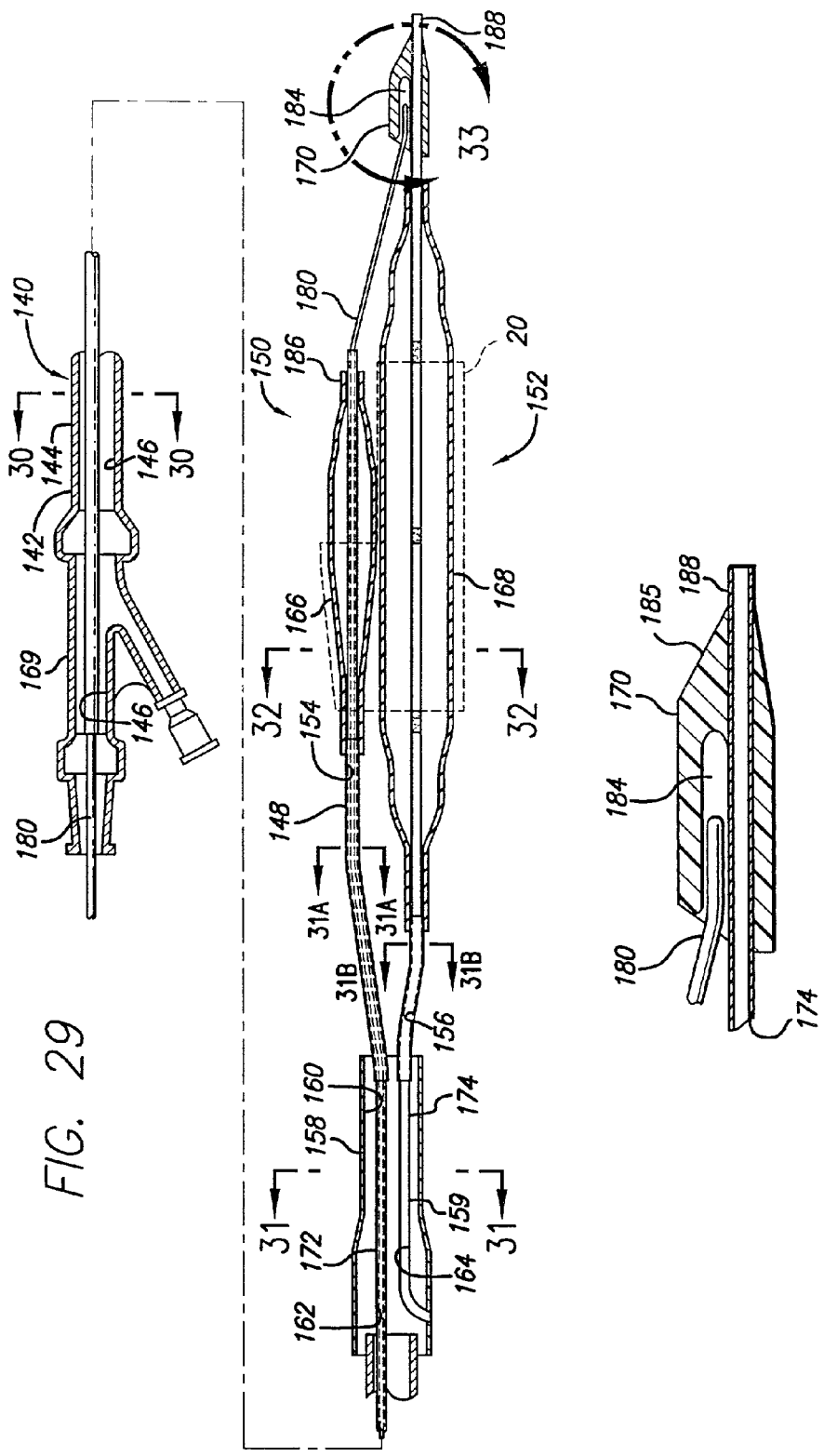

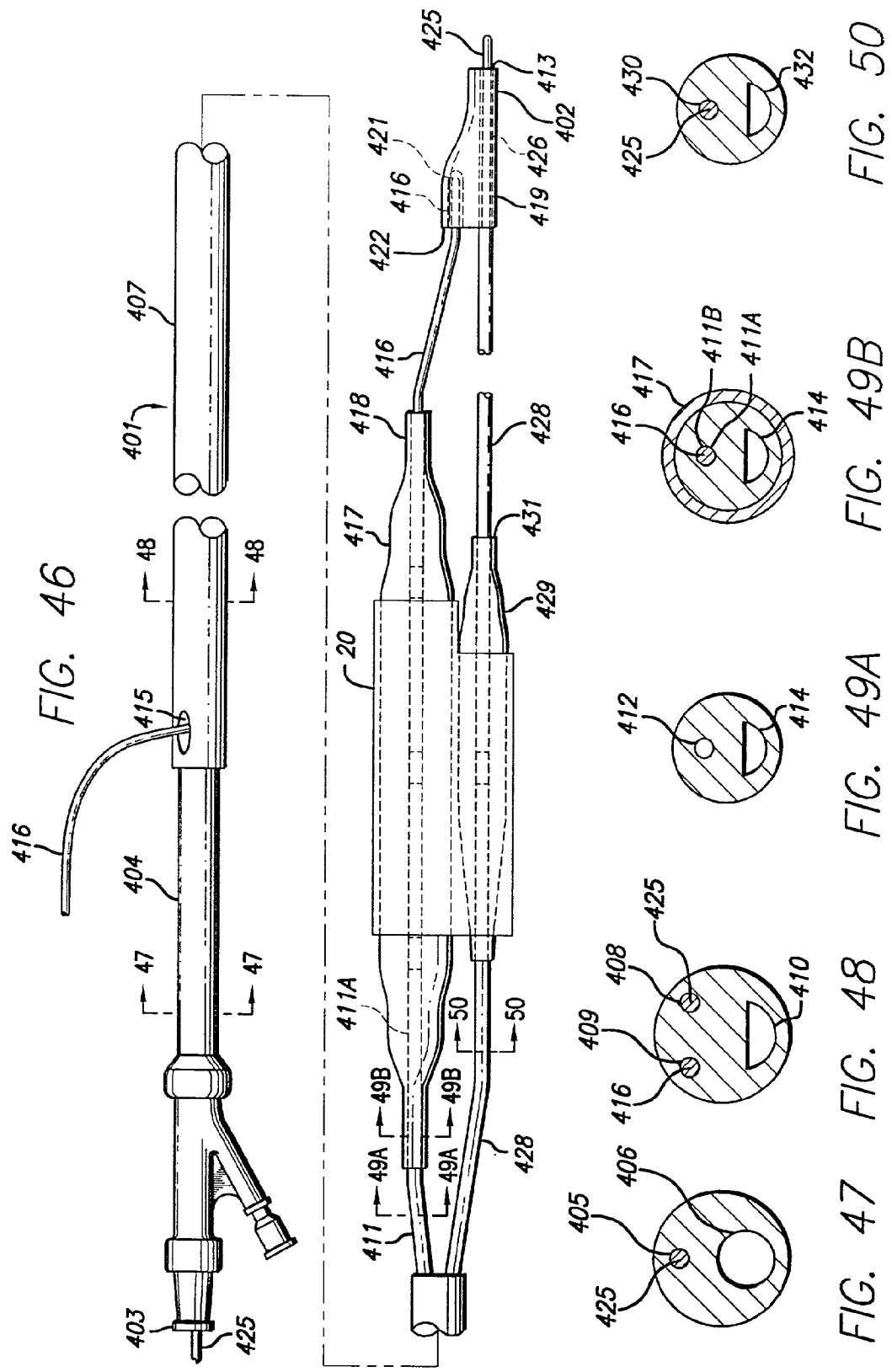

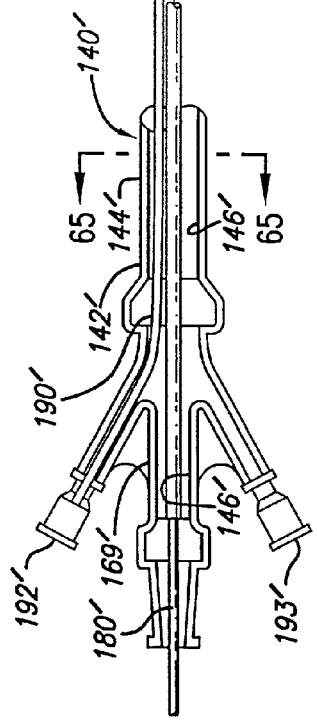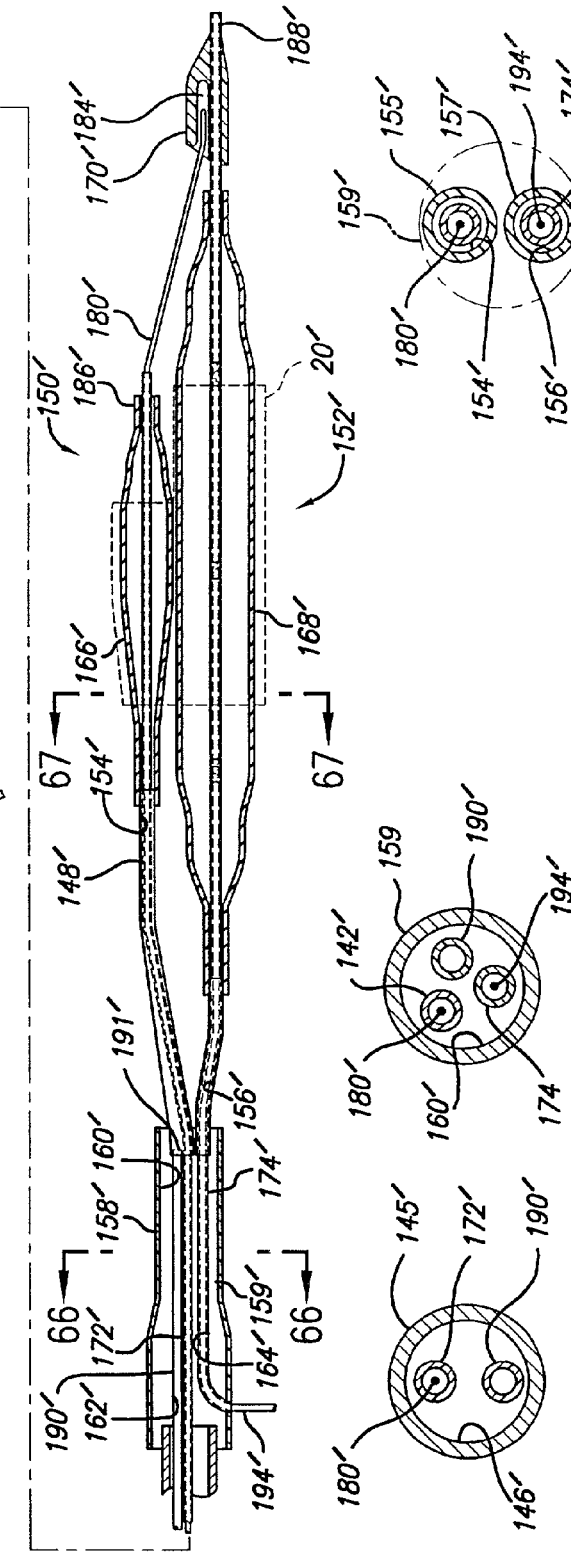

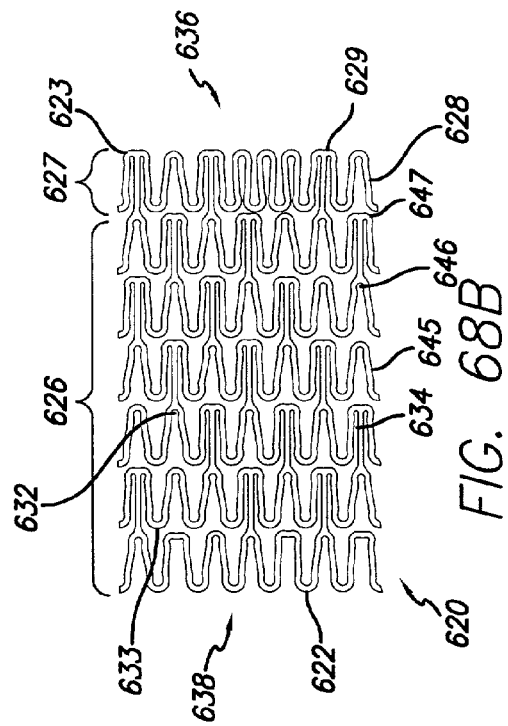
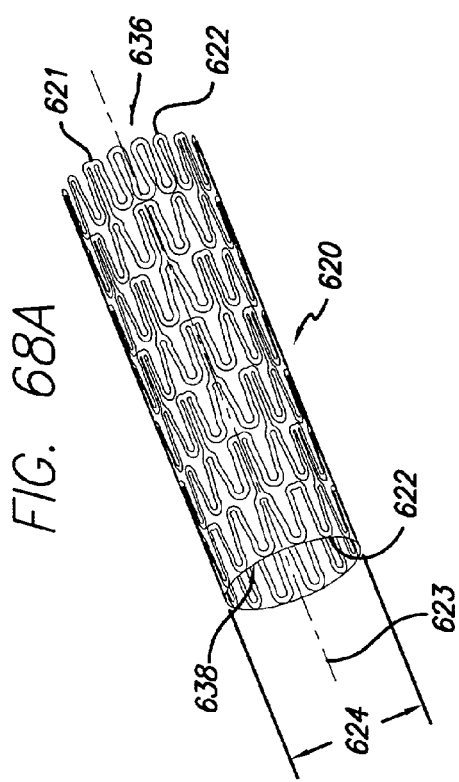
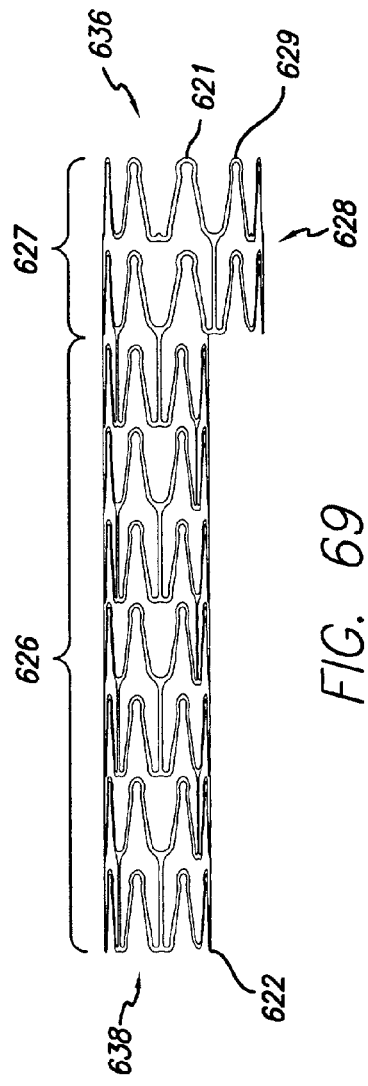

STENT FOR TREATING BIFURCATIONS AND METHOD OF USE

This application is a continuation-in-part of U.S. Ser. No. 09/861,473 filed May 17, 2001 now U.S. Pat. No. 6,749,628, which is incorporated herein by reference.

BACKGROUND OF THE INVENTION

The invention relates to stents and stent delivery and deployment assemblies for use at a bifurcation and, more particularly, one or more stents for repairing bifurcations, blood vessels that are diseased, and a method and apparatus for delivery and implantation of the stents.

Stents conventionally repair blood vessels that are diseased. Stents are generally hollow and cylindrical in shape and have terminal ends that are generally perpendicular to their longitudinal axis. In use, the conventional stent is positioned at the diseased area of a vessel and, after deployment, the stent provides an unobstructed pathway for blood flow.

Repair of vessels that are diseased at a bifurcation is particularly challenging since the stent must be precisely positioned, provide adequate coverage of the disease, provide access to any diseased area located distal to the bifurcation, and maintain vessel patency in order to allow adequate blood flow to reach the myocardium. Therefore, the stent must provide adequate coverage to the diseased portion of the bifurcated vessel, without compromising blood flow, and extend to a point within and beyond the diseased portion. Where the stent provides coverage to the vessel at the diseased portion, yet extends into the vessel lumen at the bifurcation, the diseased area is repaired, but blood flow may be compromised in other portions of the bifurcation. Unapposed stent elements may promote lumen compromise during neointimal formation and healing, producing restenosis and requiring further procedures. Moreover, by extending into the vessel lumen at the bifurcation, the stent may block access to further interventional procedures.

Conventional stents are designed to repair areas of blood vessels that are removed from bifurcations, and, therefore are associated with a variety of problems when attempting to use them to treat lesions at a bifurcation. Conventional stents are normally deployed so that the entire stent is either in the parent vessel or the proximal portion of the stent is in the parent vessel and the distal portion is located in the side branch vessel. In both cases, either the side branch vessel (former case) or the parent vessel (later case); would become "jailed" by the stent struts. This technique repairs one vessel at the bifurcation at the expense of jailing or obstructing the alternate vessel. Blood flow into the jailed vessel would be compromised as well as future access and treatment into the distal portion of the jailed vessel.

Alternatively, access into a jailed vessel can be attained by carefully placing a guide wire through the stent, and subsequently tracking a balloon catheter through the stent struts. The balloon could then be expanded, thereby deforming the stent struts and forming an opening into the previously jailed vessel. The cell to be spread apart must be randomly and blindly selected by re-crossing the deployed stent with a guide wire. The drawback with this approach is that there is no way to determine or guarantee that the main-vessel stent struts are properly oriented with respect to the side branch or that an appropriate stent cell has been selected by the wire for dilatation. The aperture created often does not provide a clear opening and creates a major distortion in the surrounding stent struts. A further drawback with this approach is that there is no way to tell if the main-vessel stent struts have been properly oriented and spread apart to provide a clear opening for stenting the side branch vessel. This technique also causes stent deformation to occur in the area adjacent to the carina, pulling the stent away from the vessel wall and partially obstructing flow in the originally non-jailed vessel. Deforming the stent struts to regain access into the previously jailed strut is also a complicated and time consuming procedure associated with attendant risks to the patient and is typically performed only if considered an absolute necessity. Vessels which supply a considerable amount of blood supply to the myocardium and may be responsible for the onset of angina or a myocardial infarct would necessitate the subsequent strut deformation in order to reestablish blood flow into the vessel. The risks of procedural complications during this subsequent deformation are considerably higher than stenting in normal vessels. The inability to place a guide wire through the jailed lumen in a timely fashion could restrict blood supply and begin to precipitate symptoms of angina or even cardiac arrest. In addition, platelet agitation and subsequent thrombus formation at the jailed site could further compromise blood flow into the side branch.

Plaque shift is also a phenomena which is of concern when deploying a stent across a bifurcation. Plaque shift occurs when treatment of disease or plaque in one vessel causes the plaque to shift into another location. This is of greatest concern when the plaque is located on the carina or the apex of the bifurcation. During treatment of the disease the plaque may shift from one side of the carina to the other thereby shifting the obstruction from one vessel to the alternate vessel.

In another prior art method of implanting stents, a "T" stent procedure includes implanting a stent in the side branch ostium of the bifurcation followed by stenting the main vessel across the side branch and subsequently deforming the struts as previously described, to allow blood flow and access into the side branch vessel. Alternatively, a stent is deployed in the parent vessel and across the side branch origin followed by subsequent strut deformation as previously described, and finally a stent is placed into the side branch vessel. T stenting may be necessary in some situations in order to provide further treatment and additional stenting in the side branch vessel. This is typically necessitated when the disease is concentrated at the origin of the jailed vessel. This procedure is also associated with the same issues and risks previously described when stenting only one vessel and deforming the struts through the jailed vessel. In addition, since a conventional stent generally terminates at right angles to its longitudinal axis, the use of conventional stents to treat the origin of the previously jailed vessel (typically the side branch vessel) may result in blocking blood flow of the originally non-jailed vessel (typically the parent vessel) or fail to provide adequate coverage of the disease in the previously jailed vessel (typically a side branch vessel). The conventional stent might be placed proximally in order to provide full coverage around the entire circumference of the side branch, however this leads to a portion of the stent extending into the pathway of blood flow of the parent vessel. The conventional stent might alternatively be placed distally to, but not entirely overlaying the circumference of the origin of the side branch to the diseased portion. Such a position of the conventional stent results in a bifurcation that does not provide full coverage or has a gap on the proximal side (the origin of the side branch) of the vessel and is thus not completely repaired. The only conceivable situation that the conventional stent, having right-angled terminal ends, could be placed where the entire circumference of the ostium is repaired without compromising blood flow, is where the bifurcation is formed of right angles. In such scenarios, extremely precise positioning of the conventional stent is required. This extremely precise positioning of the conventional stent may result with the right angled terminal ends of the conventional stent overlying the entire circumference of the ostium to the diseased portion without extending into a side branch, thereby repairing the right-angled bifurcation.

To circumvent or overcome the problems and limitations associated with conventional stents in the context of repairing diseased bifurcated vessels, a stent that consistently overlays most of the diseased area of the bifurcation and provides adequate access to distal disease without subjecting the patient to any undue risks may be employed. Such a stent would have the advantage of providing adequate coverage at the proximal edge of the origin of the side branch such that a conventional stent which terminates at right angles to its longitudinal axis can be deployed in the side branch or alternate vessel without leaving a significant gap at the origin of the side branch. In addition, such a stent would allow access to all portions of the bifurcated vessel should further interventional treatment be necessary.

In another prior art method for treating bifurcated vessels, commonly referred to as the "Culotte technique," the side branch vessel is first stented so that the stent protrudes into the main or parent vessel. A dilatation is then performed in the main or parent vessel to open and stretch the stent struts extending across the lumen from the side branch vessel. Thereafter, a stent is implanted in the side branch so that its proximal end overlaps with the parent vessel. One of the drawbacks of this approach is that the orientation of the stent elements protruding from the side branch vessel into the main vessel is completely random. In addition excessive metal coverage exists from overlapping strut elements in the parent vessel proximal to the carina area. Furthermore, the deployed stent must be recrossed with a wire blindly and arbitrarily selecting a particular stent cell. When dilating the main vessel the stent struts are randomly stretched, thereby leaving the possibility of restricted access, incomplete lumen dilatation, and major stent distortion.

In another prior art procedure, known as "kissing" stents, a stent is implanted in the main vessel with a side branch stent partially extending into the main vessel creating a double-barrelled lumen of the two stents in the main vessel distal to the bifurcation. Another prior art approach includes a so-called "trouser legs and seat" approach, which includes implanting three stents, one stent in the side branch vessel, a second stent in a distal portion of the main vessel, and a third stent, or a proximal stent, in the main vessel just proximal to the bifurcation.

All of the foregoing stent deployment assemblies suffer from the same problems and limitations. Typically, there is uncovered intimal surface segments on the main vessel and side branch vessels between the stented segments or there is excessive coverage in the parent vessel proximal to the bifurcation. An uncovered flap or fold in the intima or plaque will invite a "snowplow" effect, representing a substantial risk for sub-acute thrombosis, and the increased risk of the development of restenosis. Further, where portions of the stent are left unapposed within the lumen, the risk for subacute thrombosis or the development of restenosis again is increased. The prior art stents and delivery assemblies for treating bifurcations are difficult to use and deliver making successful placement nearly impossible. Further, even where placement has been successful, the side branch vessel can be "jailed" or covered so that there is impaired access to the stented area for subsequent intervention. The present invention solves these and other problems as will be shown.

In addition to problems encountered in treating disease involving bifurcations for vessel origins, difficulty is also encountered in treating disease confined to a vessel segment but extending very close to a distal branch point or bifurcation which is not diseased and does not require treatment. In such circumstances, very precise placement of a stent covering the distal segment, but not extending into the distal side branch, may be difficult or impossible. The present invention also offers a solution to this problem.

SUMMARY OF THE INVENTION

The invention provides for improved stent designs and stent delivery catheter assemblies for repairing a main vessel and side branch-vessel forming a bifurcation, without compromising blood flow, thereby allowing access to all portions of the bifurcated vessels should further interventional treatment be necessary. The present invention includes a trap-door stent pattern, a stent delivery catheter assembly, and the method for delivering and implanting the stent in a bifurcated vessel.

The Stent Pattern

The stent of the present invention includes a cylindrical body having rings aligned along a longitudinal axis, where each ring has a delivered diameter in which it is crimped or compressed tightly onto the balloon catheter, and an implanted diameter where the stent is implanted in a bifurcated vessel. Each ring also includes a number of peaks that are configured to spread apart to permit the rings to be greatly expanded outwardly or to be compressed radially inwardly onto the balloon portion of a delivery catheter. In one embodiment of the stent of the present invention, the cylindrical body of the stent includes a plurality of first rings and at least one second ring along a longitudinal axis. The rings are attached to each other by links having either a linear configuration, a non-linear configuration, or a combination of both. Each of the rings has a series of undulations in the form of peaks and valleys which can compress or expand radially so that the stent can be crimped onto a balloon catheter, and be expanded by the balloon portion of the catheter in a vessel such as a coronary artery. A trap door section includes a distal end ring which, when expanded, will appose the opening to a side branch vessel at a bifurcation. The first rings are expanded and implanted in the main vessel at a point proximal to the side branch vessel. The trap door section, with the distal end ring, is expanded and implanted at the opening of the side branch vessel. When expanded, the first rings have a substantially circular cross-section while the distal end ring has a substantially elliptical cross-section since it expands into not only the opening to the side branch vessel, but also extends into and apposes the main vessel wall. The stent of this embodiment can be used with any of the stent delivery catheters described herein and the method of implanting is further described herein.

The links connecting the rings can have various embodiments including straight segments, curved segments, undulating segments, and non-linear segments.

The stent of the present invention includes struts that make up the rings and links, the struts having either uniform cross-sections, or cross-sections having various widths and thicknesses.

The Stent Delivery Catheter

The present invention also includes a stent delivery catheter assembly for repairing bifurcated vessels including an elongated catheter body which has a proximal catheter shaft, an intermediate section or mid-section, and a distal section. The catheter assembly contains an over-the-wire (OTW)

guide wire lumen extending from the proximal catheter hub to one of the distal tips of the distal end of the catheter. The catheter assembly also includes a rapid exchange (Rx) guide wire lumen which extends from the proximal end of the mid-section to one of the distal tips of the distal end of the catheter. The proximal catheter shaft also contains an inflation lumen which extends from the proximal hub of the proximal catheter shaft to the mid-section of the catheter and is in fluid communication with the inflation lumen contained within the mid-section. The mid-section contains lumens for both an OTW and an Rx guide wire lumen. The Rx guide wire lumen begins at about the proximal section of the intermediate shaft and extends to one of the distal tips of the distal catheter shaft. The OTW guide wire lumen extends through the intermediate section of the catheter and extends proximally to the catheter hub connected to the proximal catheter shaft and extends distally to one of the tips of the distal section of the catheter. The distal section of the catheter consists of two shafts extending from the distal end of the mid-shaft to the distal end of the catheter tips. Each shaft has a balloon connected adjacent the distal end followed by a tip connected to the distal end of the balloon. Each shaft contains a guide wire lumen and an inflation lumen. The inflation lumen of each shaft is in fluid communication with the inflation lumen of the mid-shaft. One of the shafts of the distal section contains an Rx guide wire lumen, which extends proximally through the mid-section of the catheter and exits at about the proximal end of the mid-section of the catheter, the Rx guide wire lumen also extends distally to one of the tips of the distal section of the catheter. The second shaft of the distal section contains an OTW guide wire lumen, which extends proximally through the mid-section and proximal section of the catheter and exits at the proximal hub connected to the distal end of the proximal catheter section, the OTW guide wire lumen also extends distally to one of the tips of the distal section of the catheter. The distal section of the catheter includes two balloons. One balloon is longer and is connected to one of the shafts of the distal catheter section. The long balloon is connected to the catheter shaft such that the inflation lumen of the shaft is in fluid communication with the balloon and the guide wire lumen contained within the shaft extends through the center of the balloon. The proximal section of the balloon is sealed to the distal end of the shaft and the distal end of the balloon is sealed around the outside of the guide wire lumen or inner member running through the center of the balloon. The proximal and distal seals of the balloon allow for fluid pressurization and balloon inflation from the proximal hub of the catheter. The short balloon is connected in the same manner as the long balloon described above to the alternate shaft of the distal section of the catheter. Each balloon has a tip extending from their distal ends. The tips are extensions of the inner members extending through the center of the balloon and contain a lumen for a guide wire associated with each guide wire lumen. The distal end of the catheter has two tips associated with their respective balloons and the guide wire lumen or inner member. One tip is longer and contains a coupler utilized for joining the tip during delivery of the previously described stent.

The stent of the present invention is crimped or compressed onto the long balloon and the short balloon such that the long balloon extends through the distal opening and the proximal opening in the stent, while the short balloon extends through the proximal opening and the central opening of the stent.

In one embodiment of the bifurcated catheter assembly, the OTW guide wire lumen extends through the short balloon and the short tip. The OTW guide wire and short balloon are configured for treating the side branch or alternate vessel. The Rx guide wire lumen extends through the long balloon and the long tip and coupler. The Rx guide wire and the long balloon and long tip are configured for treating the parent or main vessel. The coupler consists of a joining lumen adjacent to and connected to the long tip. The lumen extends from the proximal end of the long tip and extends between 1 mm to about 20 mm to the end of the long tip where it terminates. The proximal end of the joining lumen is located distal to the position of the short tip. A joining wire extends through the proximal hub and distally exits the short tip and then enters the joining lumen of the coupler on the long tip thereby joining the two tips. The proximal hub has a mechanism which locks the joining wire into position while the catheter and stent are tracked into position. The wire can then be released or unlocked at the appropriate time and retracted to release or uncouple the tips. The locking mechanism on the proximal hub is similar to a Rotating Hemostatic Valve (RHV) mechanism which consists of a two part housing with an O ring inside. The two part housing has one piece with male threads and another with female threads. The housing is screwed together until compression is applied to the O ring causing the inside diameter of the O ring to continually decrease until it locks onto the joining wire. Alternatively, the OTW guide wire can be used as the joining wire.

In another embodiment of the bifurcated catheter assembly, the long tip contains a series of holes on the distal section of the long tip and the short tip contains a series of holes on the distal section of the short tip. The holes are aligned and spaced on the long and short tip such that a staggered relationship between hole pairs is created between the holes on the long and short tip. The tips are then coupled by a joining wire which is threaded through the staggered hole pairs in the distal section of the long and short tips. The joining wire extends proximally through the OTW guide wire lumen to the proximal hub where it is locked in place as previously described. The Rx guide wire extends through the Rx guide wire lumen proximally through the center of the long balloon and exits the Rx notch located on the mid-section of the catheter and extends distally through the long tip and into the distal anatomy. The diameter of the joining wire is such that it occupies minimal space in the Rx guide wire lumen and does not create interference with the Rx guide wire. The tips are uncoupled at the appropriate time by unlocking the joining wire and removing it from the anatomy.

In another embodiment of the bifurcated catheter assembly, the OTW guide wire lumen extends through the long tip and coupler, and the long tip is connected to the short balloon. The OTW guide wire lumen and short balloon are configured for treatment of the side branch or alternate vessel. The OTW guide wire lumen extends to the proximal hub of the proximal section of the catheter. The Rx guide wire lumen extends through the long balloon and short tip distally and extends proximally to the exit notch located on the mid-section of the catheter. The Rx guide wire lumen and long balloon are configured to treat the parent or main vessel. The coupler consists of a joining lumen adjacent to and attached to the distal end of the long tip. The proximal end of the joining lumen is located distal to the short tip and the distal end of the joining lumen extends slightly beyond the long tip. The end of the joining lumen is open and the Rx guide wire extends distally through the joining lumen and into the distal anatomy and extends proximally through the short tip and long balloon to the exit notch located on the mid-section of the catheter. The OTW guide wire extends from the distal end of the long tip to the proximal hub located on the proximal section of the catheter. The tips are uncoupled at the appropriate location and time during the procedure by retracting the Rx guide wire such that the tip of the wire exits the coupling lumen located in the distal section of the Rx tip.

In another embodiment of the bifurcated catheter assembly, the long tip contains a slit used for coupling the two tips together. The Rx guide wire extends through the Rx guide wire lumen contained in the short tip and extends proximally through the center of the long balloon and exits the Rx guide wire exit notch located on the mid-section of the catheter. The Rx guide wire extends distally through the Rx guide wire lumen and exits the short tip and then enters the distal section of long tip through the slit. The Rx guide wire exits the long tip and continues distally through the anatomy. The OTW guide wire extends from the distal end of the long tip to the proximal hub located on the proximal section of the catheter. The tips are uncoupled at the appropriate location and time during the procedure by retracting the Rx guide wire such that the tip of the wire exits the slit located in the distal section of the long tip.

In another embodiment of the bifurcated catheter assembly, the long tip contains two slits on the distal section of the long tip. The Rx guide wire extends through the Rx guide wire lumen contained in the short tip and extends proximally through the center of the long balloon and exits the Rx guide wire exit notch located on the mid-section of the catheter. The Rx guide wire extends distally through the Rx guide wire lumen and exits the short tip and then enters the distal section of long tip through one of the slits. The Rx guide wire exits the long tip and continues distally through the anatomy. The OTW guide wire extends from the distal end of the long tip to the proximal hub located on the proximal section of the catheter. The tips are uncoupled at the appropriate location and time during the procedure by retracting the Rx guide wire such that the tip of the wire exits the slit located in the distal section of the long tip. Before the tips are uncoupled, the OTW guide wire is advanced through the long tip and exits the alternate slit and continues into the distal anatomy. Advancement of the OTW guide wire before retracting the Rx guide wire for uncoupling always ensures wire placement in the distal and diseased anatomy. Maintaining a wire in the distal and diseased anatomy ensures access to the vessel in the event of vessel closure due to vessel dissection or spasm.

In another embodiment of the bifurcated catheter assembly, the long tip contains a slit in the distal section of the long tip and is configured to allow the inner diameter of the lumen to expand when an outward radial force is applied (by a guide wire pushed from the proximal end) and contract to its original shape when the guide wire is removed. The tip is formed from a material having elastic and retractable properties such as found in a variety of elastomers. An expandable pattern such as minute cuts or slits, can then be cut (with a laser) in the distal section of the long tip. The expandable pattern contains elements which deform when an outward radial force is applied to the inside of the lumen. The elements then return to their original shape when the outward radial force is removed. An alternate method of creating an expandable tip would be to utilize a more conventional tip or inner member material, and then subsequently cut an expandable pattern (slits) in the distal section of the tip. An additional material with the appropriate elastic and retractable properties can then be coated or bonded over the distal section of the long tip to impart the expandable properties of the tip. The Rx guide wire extends through the Rx guide wire lumen contained in the short tip and extends proximally through the center of the long balloon and exits the Rx guide wire exit notch located on the mid-section of the catheter. The Rx guide wire extends distally through the Rx guide wire lumen and exits the short tip and then enters the distal section of long tip through the slit. The Rx guide wire exits the long tip and continues distally through the anatomy. The OTW guide wire extends from the distal end of the long tip to the proximal hub located on the proximal section of the catheter. During delivery of the stent, the distal end of the OTW guide wire remains in the distal section of the long tip just proximal of the slit. Before the tips are uncoupled, the OTW guide wire is advanced through the long tip which will expand upon advancement of the OTW guide wire since both of the guide wires will exit through the portion of the long tip distal of the slit. The tips are then uncoupled at the appropriate location and time during the procedure by retracting the Rx guide wire such that the tip of the wire exits the slit located in the distal section of the long tip.

The present invention also includes a stent delivery catheter assembly for repairing bifurcated vessels including an elongated catheter body which has a proximal end and a distal end and a proximal catheter shaft and an over-the-wire (OTW) guide wire lumen extending therethrough. The catheter assembly also includes a rapid exchange (Rx) catheter portion attached to the distal end of the proximal catheter shaft, the Rx catheter portion having a distal end and a proximal end with an Rx guide wire lumen extending therethrough and a coupler associated with the distal end of the Rx catheter portion. The catheter body also includes an OTW catheter portion attached to the distal end of the proximal catheter shaft, where the OTW catheter portion includes an OTW guide wire lumen that corresponds with and aligns with the OTW guide wire lumen in the proximal catheter shaft. A long balloon is associated with the Rx catheter portion and a short balloon is associated with the OTW catheter portion. The Rx catheter portion is configured for treating the main vessel of a bifurcation and the OTW catheter portion is configured for treating a side branch vessel of the bifurcation. Alternatively, the OTW catheter portion is configured for treating the main vessel of a bifurcation, while the Rx catheter portion is configured for treating a side branch vessel of the bifurcation. The stent of the present invention is crimped or compressed onto the long balloon and the short balloon such that the long balloon extends through the distal opening and the proximal opening in the stent, while the short balloon extends through the proximal opening and the central opening of the stent.

In another embodiment of the bifurcated catheter assembly of the invention, the bifurcated catheter can be used for a variety of procedures such as dilatation, drug delivery, and delivering and deploying the stent of the invention in a body lumen. The bifurcated catheter assembly includes an elongated shaft having a proximal shaft section with a first inflation lumen and a multifurcated distal shaft section with a first branch and at least a second branch. The first branch has a second inflation lumen with at least a portion thereof in fluid communication with the first inflation lumen. An intermediate shaft section joins the proximal and distal sections together and defines a fourth inflation lumen in fluid communication with the first, second and third inflation lumens. A joining wire lumen extends within the proximal section, the intermediate section, and the first branch of the multifurcated distal section. The guide wire lumen extends within the intermediate section and the second branch of the multifurcated distal section. The guide wire lumen extends within the intermediate section and the second branch of the multifurcated distal section. A first balloon is positioned on the first branch and a second balloon is positioned on the second branch, with interiors of the balloons in fluid communication with the inflation lumens. A coupler is associated with the second branch, distal to the second balloon, and is configured for releasably coupling the first and second branches together to form a coupled configuration.

Delivering and Implanting the Stent

The method of delivering and implanting the stent mounted on the catheter assembly are contemplated by the present invention. The bifurcated catheter assembly of the present invention provides two separate balloons in parallel which are advanced into separate passageways of an arterial bifurcation and the balloons are inflated either simultaneously or independently (or a combination thereof) to expand and implant the stent. More specifically, and in keeping with the invention, the catheter assembly is advanced through a guiding catheter (not shown) until the distal end of the catheter assembly reaches the ostium to the coronary arteries. An Rx guide wire is advanced out of the Rx shaft and into the coronary arteries to a point distal of the bifurcation or target site. In a typical procedure, the Rx guide wire will already be positioned in the main vessel after a pre-dilatation procedure. The catheter assembly is advanced over the Rx guide wire so that the catheter distal end is just proximal to the opening to the side branch vessel. Up to this point in time, the OTW guide wire (or mandrel or joining wire) remains within the catheter assembly and within the coupler so that the long balloon and the short balloon of the catheter assembly remain adjacent to one another to provide a low profile. As the catheter assembly is advanced to the bifurcated area, the coupler moves axially relative to the distal end of the OTW guide wire (or mandrel or joining wire) a small distance (approximately 0.5 mm up to about 5.0 mm), but not pull completely out of the coupler, making it easier for the distal end of the catheter to negotiate tortuous turns in the coronary arteries. Thus, the slight axial movement of the coupler relative to the OTW guide wire (or mandrel or joining wire) distal end allows the tips to act or move independently, thereby increasing flexibility over the tips joined rigidly and it aids in the smooth tracking of the catheter assembly over the Rx guide wire. The proximal end of the OTW guide wire is releasably attached to the proximal hub as previously described. The OTW guide wire (or mandrel or joining wire) is removed or withdrawn proximally from the coupler, thereby uncoupling the long balloon and the short balloon. Thereafter, the OTW guide wire is advanced distally into the side branch vessel so that the catheter assembly can next be advanced distally over the Rx guide wire in the main vessel and the OTW guide wire in the side branch vessel. The separation between the Rx guide wire and the OTW guide wire allows the long balloon and the short balloon to separate slightly as the catheter assembly is further advanced over the Rx guide wire and the OTW guide wire. The catheter assembly advances distally until it reaches a point where the distal end of the stent is approximately adjacent to the opening to the side branch vessel, so that the catheter assembly can no longer be advanced distally since the stent is now pushing up against the opening to the side branch vessel. One or more radiopaque markers are placed on the distal portion of the catheter assembly to aid in positioning the stent with respect to the bifurcation or target site. Once the long and short balloons with the stent mounted thereon are positioned in the main vessel just proximal to the side branch vessel, the long balloon and the short balloon are next inflated simultaneously or independently (or a combination thereof), to expand the stent in the main vessel and the opening to the side branch vessel. The distal portion of the stent is expanded into contact with the opening to the side branch vessel and the distal opening should substantially coincide with the opening to the side branch vessel providing a clear blood flow path through the proximal opening of the stent and into the side branch vessel. By inflating the long balloon and the short balloon substantially simultaneously, plaque shifting is avoided and better vessel wall coverage results. After implanting the stent, the distal opening will have a substantially elliptical shape due to the shape of the vessel opening. Importantly, the proximal section of the stent apposes the main vessel wall at a location proximal to the opening to the side branch vessel so that the stent does not cover the main vessel distal to the bifurcation which does not require repair or treatment.

After the stent of the present invention has been implanted at the bifurcation, if necessary a second stent can be implanted in the side branch vessel so that the second stent abuts the central opening of the stent of the present invention.

BRIEF DESCRIPTION OF THE DRAWINGS

FIGS. 6A-6E are perspective views depicting different embodiments of the stent of the present invention in an unexpanded configuration.

FIGS. 7A-7E are flattened elevational views of the stents of FIGS. 6A-6E respectively, depicting different embodiments of the stent of the present invention in a flattened configuration.

FIG. 21 is a flattened elevation view depicting one embodiment of the stent of the present invention in which at least some of the links have an undulating portion.

FIG. 22B is a portion of the stent pattern of the invention depicting struts of variable width.

FIG. 23 is an elevational view of the catheter assembly for delivering and implanting the stent of the invention.

FIG. 23A is an elevational view of the catheter assembly configured for independent inflation.

FIG. 23B is a cross-sectional view taken along lines 23B-23B depicting the cross-section of the proximal shaft of the independent inflation catheter.

FIG. 23C is a cross-sectional view taken along lines 23C-23C depicting the cross-section of the mid-shaft of the independent inflation catheter.

FIG. 23D is a cross-sectional view taken along lines 23D-23D depicting the cross-section of the Rx shaft of the independent inflation catheter.

FIG. 23E is a cross-sectional view taken along lines 23E-23E depicting the cross-section of the OTW shaft of the independent inflation catheter.

FIG. 24 is a cross-sectional view taken along lines 24-24 depicting the cross-section of the proximal shaft of the catheter.

FIG. 25 is a cross-sectional view taken along lines 25-25 depicting the cross-section of a portion of the catheter shaft.

FIG. 26A is a cross-sectional view taken along lines 26A-26A depicting the cross-section of the Rx catheter shaft.

FIG. 26B is a cross-sectional view taken along lines 26B-26B depicting the cross-section of the over-the-wire shaft.

FIG. 27 is a longitudinal cross-sectional view of the coupler.

FIG. 28A is a longitudinal cross-sectional view depicting a portion of the catheter distal end including the radiopaque markers.

FIG. 28B is a transverse cross-sectional view taken along lines 28B-28B depicting the inner member and long balloon.

FIG. 29 is an elevational view of one embodiment of the catheter assembly for delivering and implanting the stent of the invention.

FIG. 33 is a longitudinal cross-sectional view of the coupler depicting a guide wire slidably positioned in the dead-end lumen of the coupler.

FIG. 46 is an elevational view of an alternative embodiment of the catheter assembly.

FIG. 47 is a transverse cross-sectional view taken along lines 47-47 depicting the proximal shaft of the catheter.

FIG. 48 is a transverse cross-section view taken along lines 48-48 depicting the mid-shaft portion of the catheter.

FIG. 49A is a transverse cross-section view taken along lines 49A-49A depicting the Rx distal shaft of the catheter.

FIG. 49B is a transverse cross-sectional view taken along lines 49B-49B depicting the inner member associated with the Rx shaft portion of the catheter.

FIG. 50 is a transverse cross-sectional view taken along lines 50-50 depicting the OTW shaft portion of the catheter.

FIG. 64 is an elevational view of one embodiment of the catheter assembly configured for independent inflation of the balloons.

FIG. 65 is a transverse cross-sectional view taken along lines 65-65 depicting the proximal shaft section of the catheter.

FIG. 66 is a transverse cross-sectional view taken along lines 66-66 depicting the mid or intermediate shaft section of the catheter.

FIG. 67 is a transverse cross-sectional view taken along lines 67-67 depicting the multifurcated distal section of the catheter.

FIG. 68A is a perspective view depicting one embodiment of the stent of the present invention in an unexpanded configuration.

FIG. 68B is a flattened elevational view of the stent of 68A depicting a stent of the present invention in a flattened configuration.

FIG. 69 is an elevational view depicting the stent of FIGS. 68A and 68B.

DETAILED DESCRIPTION OF THE PREFERRED EMBODIMENTS

Figure 1:
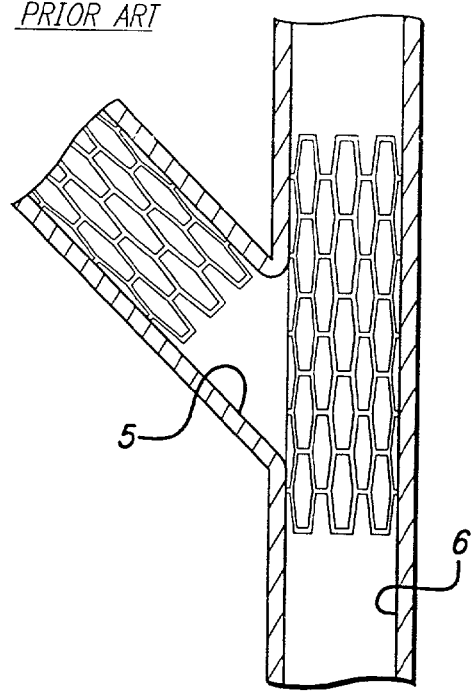
FIG. 1 is an elevational view of a bifurcation in which a prior art "T" stent is in a side branch ostium followed by the stenting of the main vessel across the branch ostium.

The present invention includes a stent and stent delivery catheter assembly and method for treating bifurcations in, for example, the coronary arteries, veins, peripheral vessels and other body lumens. Prior art attempts at implanting intravascular stents in a bifurcation have proved less than satisfactory. For example, FIGS. 1-4 depict prior art devices which include multiple stents being implanted in both the main vessel and a side branch vessel. In FIG. 1, a prior art "T" stent is implanted such that a first stent is implanted in the side branch near the origin of the bifurcation, and a second stent is implanted in the main vessel, into the side branch. With this approach, portions of the side branch vessel are left uncovered, and blood flow to the side branch vessel must necessarily pass through the main vessel stent, causing possible obstructions or thrombosis.

Figure 2:
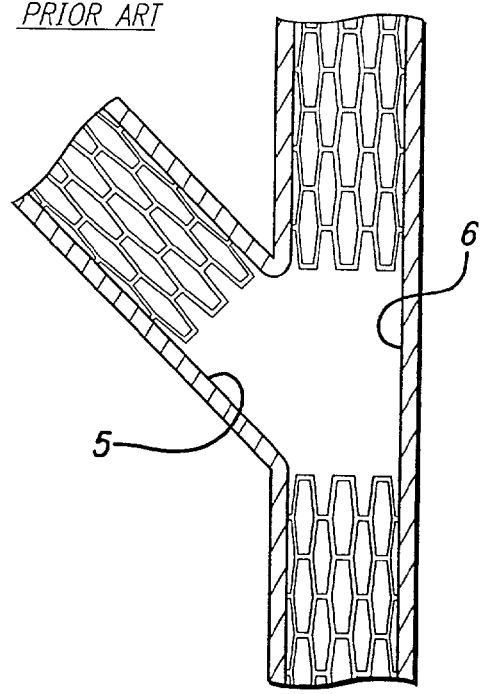
FIG. 2 is an elevational view of a bifurcation in which "touching" prior art stents are depicted in which one stent is implanted in the side branch, a second stent implanted in a proximal portion of the main vessel next to the branch stent, with interrupted placement of a third stent implanted more distally in the main vessel.
Figure 3:
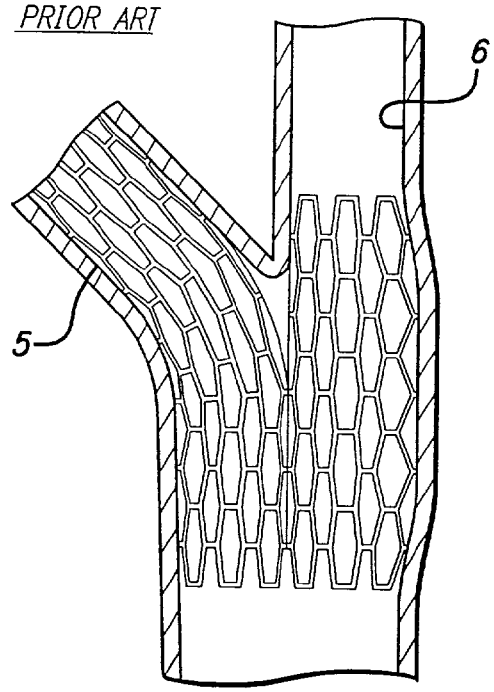
FIG. 3 is an elevational view of a bifurcation depicting "kissing" stents where a portion of one stent is implanted in both the side branch and the main vessel and adjacent to a second stent implanted in the main vessel creating a double-barreled lumen in the main vessel distal to the bifurcation.
Figure 4:
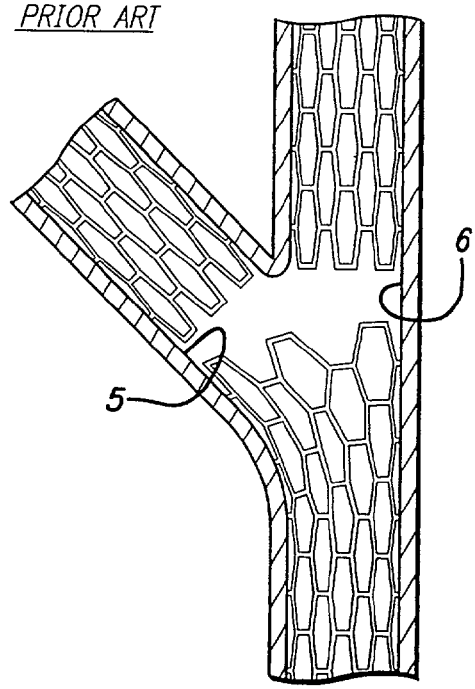
FIG. 4 is an elevational view of a prior art "trouser legs and seat" stenting approach depicting one stent implanted in the side branch vessel, a second stent implanted in a proximal portion of the main vessel, and a close deployment of a third stent distal to the bifurcation leaving a small gap between the three stents of an uncovered luminal area.

Referring to FIG. 2, three prior art stents are required to stent the bifurcation. In FIG. 3, the prior art method includes implanting two stents side by side, such that one stent extends into the side branch vessel and the main vessel, and the second stent is implanted in the main vessel. This results in a double-barreled lumen which can present problems such as thrombosis, and turbulence in blood flow. Referring to the FIG. 4 prior art device, a first stent is implanted in the side branch vessel, a second stent is implanted in a proximal portion of the main vessel, and a third stent is implanted distal to the bifurcation, thereby leaving a small gap between the stents and an uncovered luminal area.

All of the prior art devices depicted in FIGS. 1-4 have various drawbacks which have been solved by the present invention.

Figure 5A:
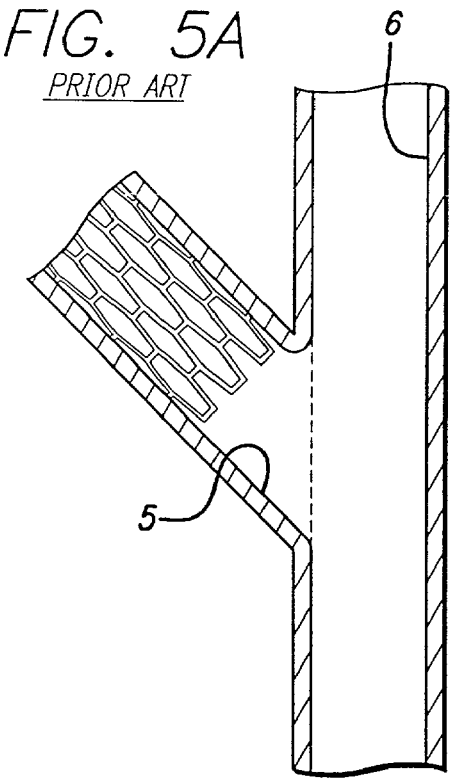
FIG. 5A is an elevational view of a bifurcation in which a prior art stent is implanted in the side branch vessel.
Figure 5B:
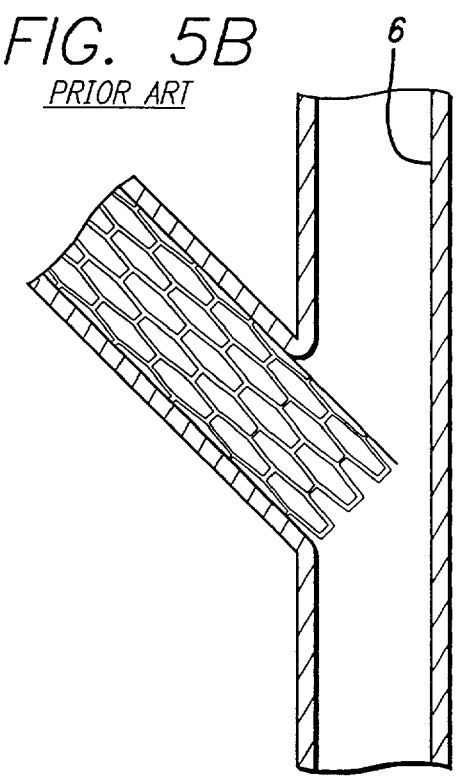
FIG. 5B is an elevational view of a bifurcation in which a prior art stent is implanted in the side branch vessel, with the proximal end of the stent extending into the main vessel.
Figure 6C:
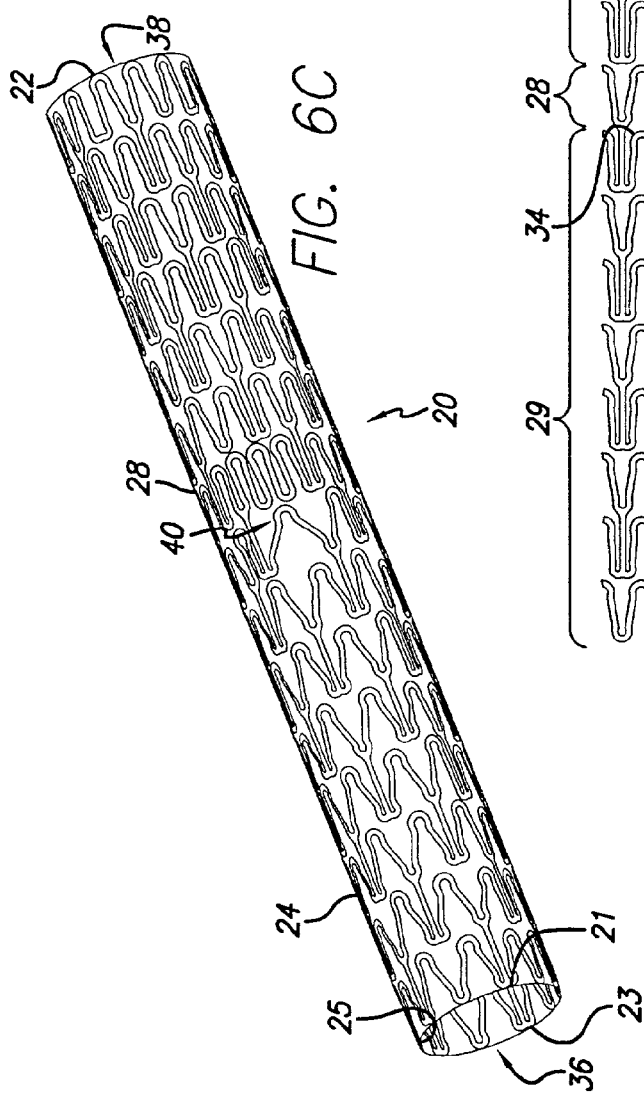
Figure 7C:
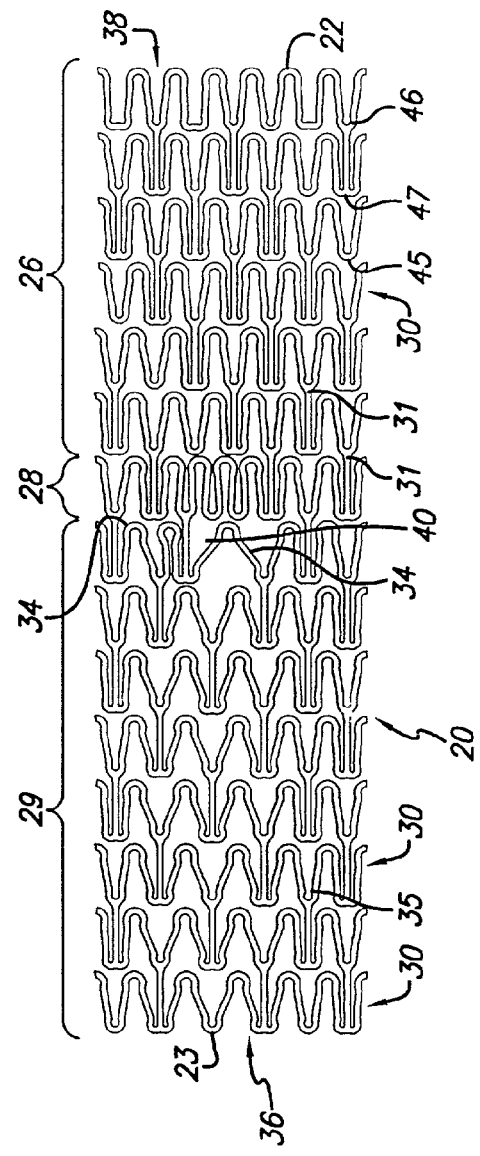
Figure 6D:
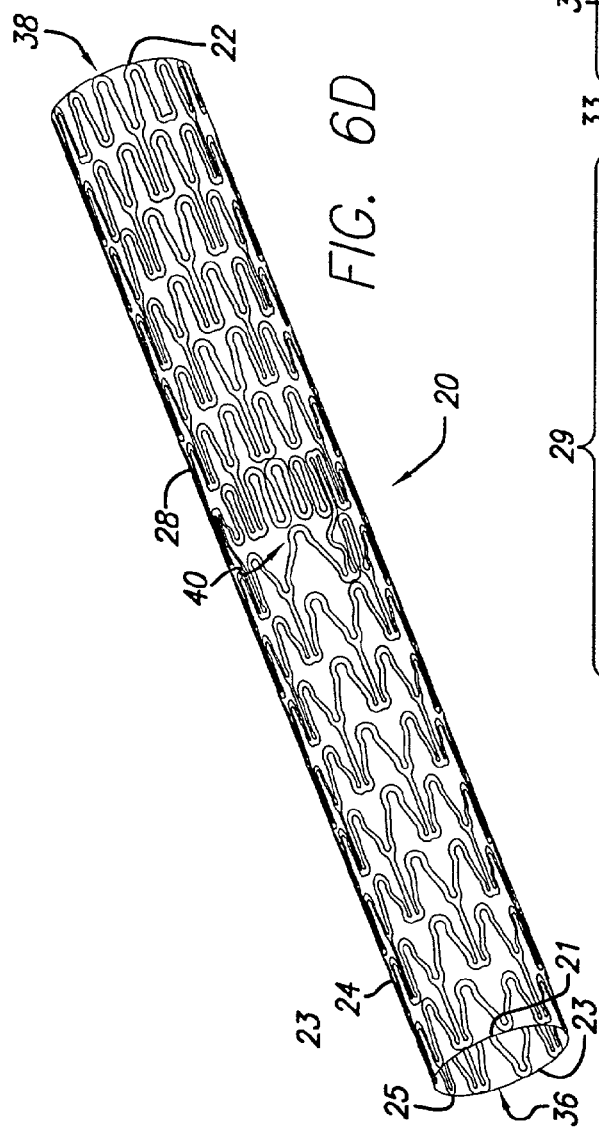
Figure 7D:
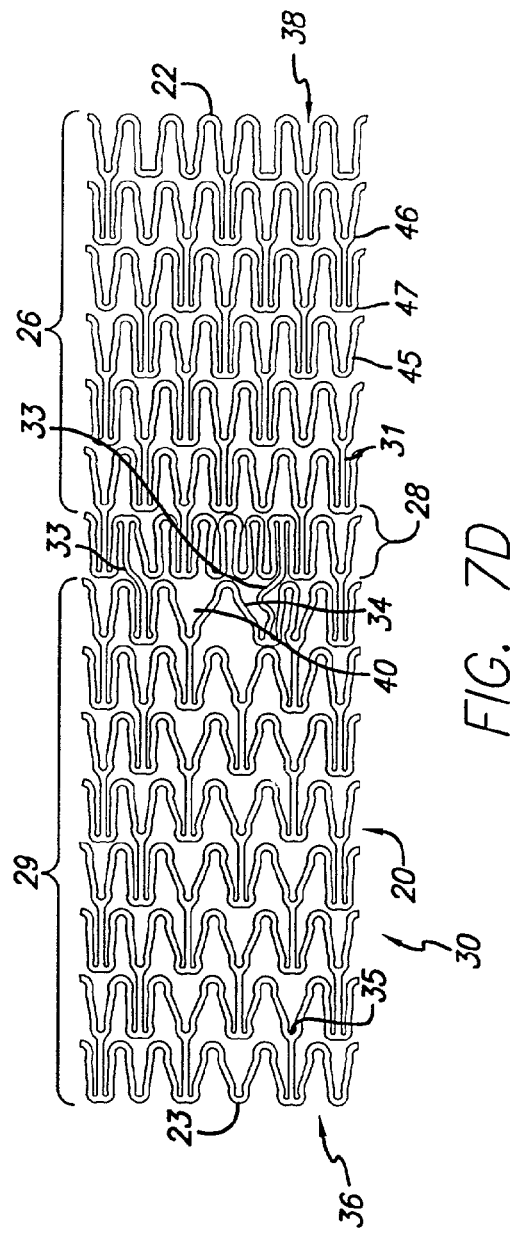
Figure 8:
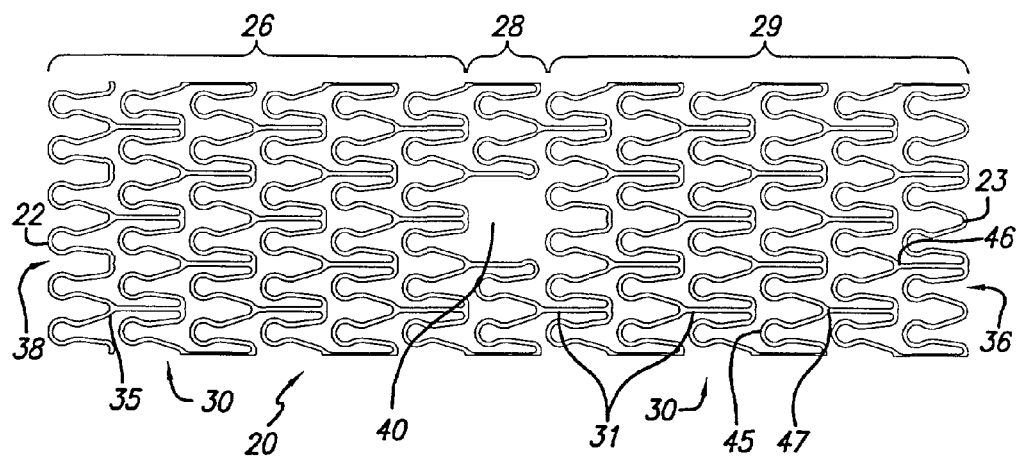
FIG. 8 is a flattened elevational view of one embodiment of the stent of the present invention.
Figure 9:
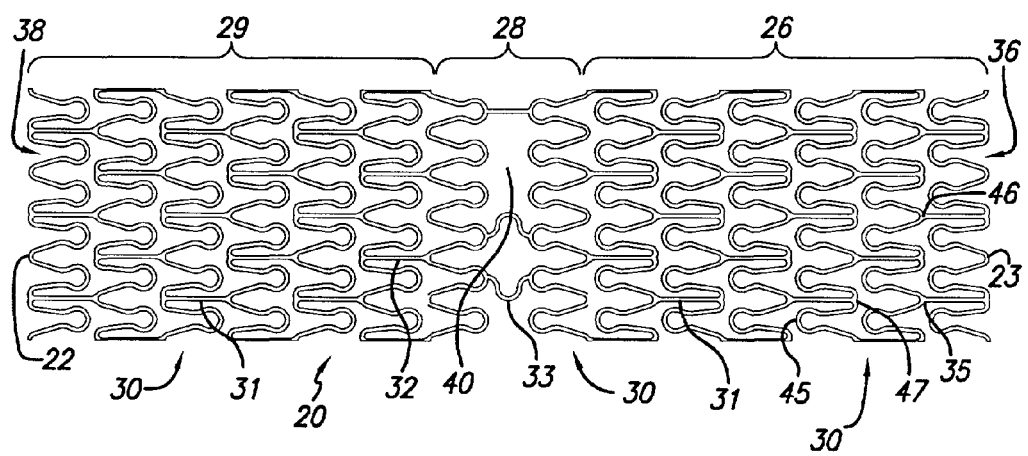
FIG. 9 is a flattened elevational view of one embodiment of the stent of the present invention.
Figure 10:
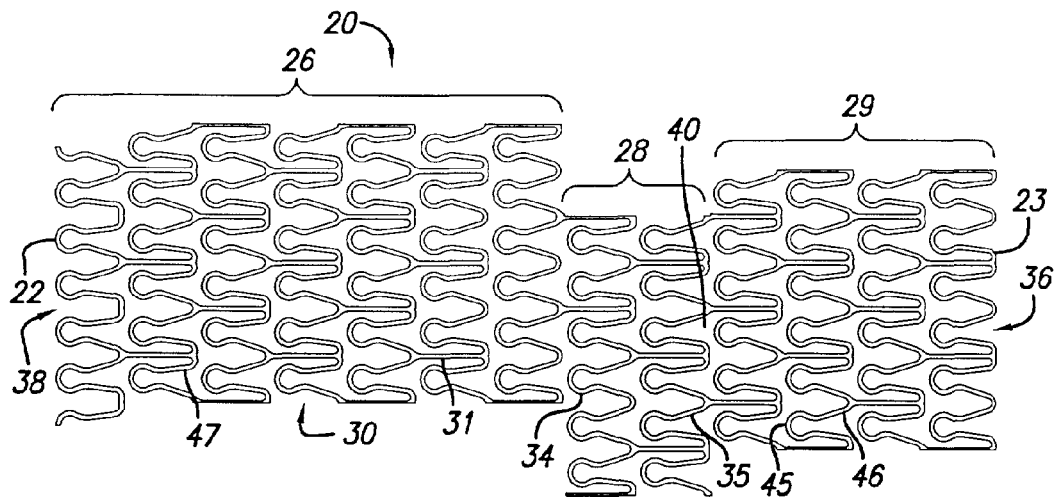
FIG. 10 is a flattened elevational view of one embodiment of the stent of the present invention.
Figure 11:
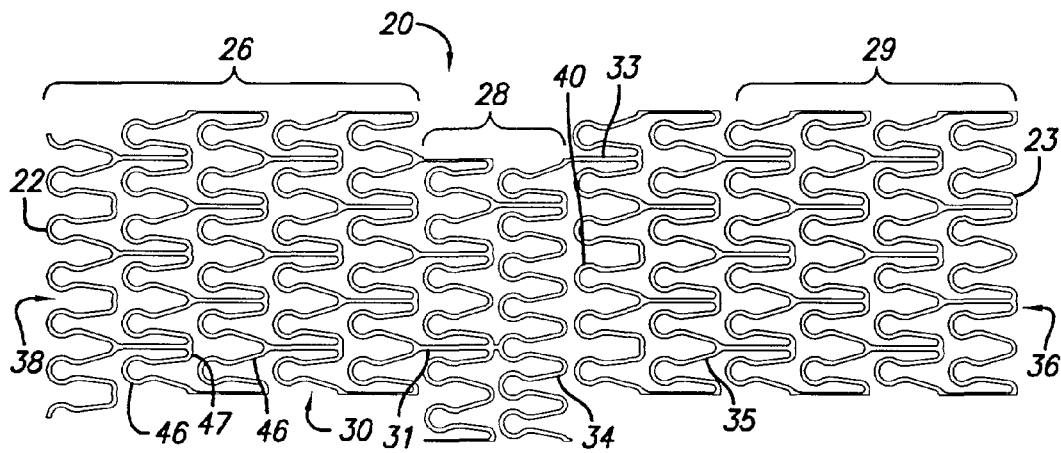
FIG. 11 is a flattened elevational view of one embodiment of the stent of the present invention.
Figure 12:
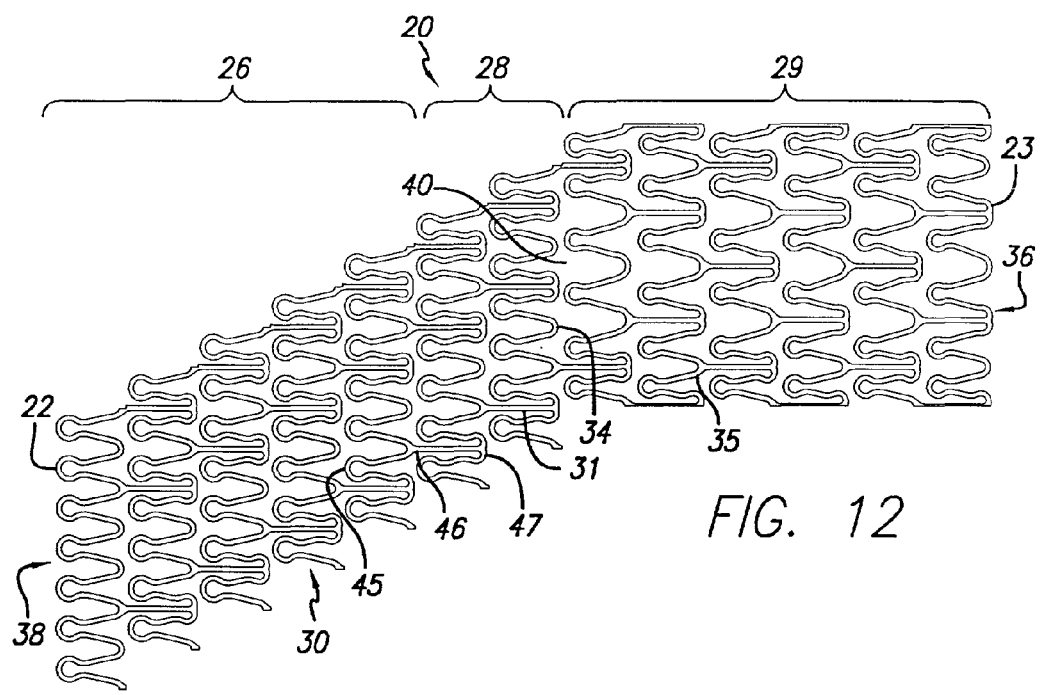
FIG. 12 is a flattened elevational view of one embodiment of the stent of the present invention.
Figure 13:
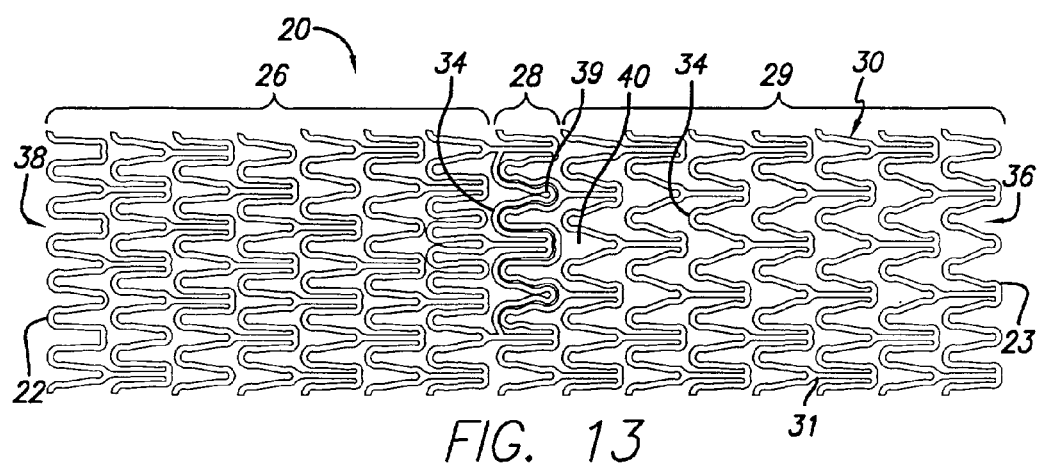
FIG. 13 is a flattened elevational view depicting a central section of the stent having a nested ring portion.
Figure 14:
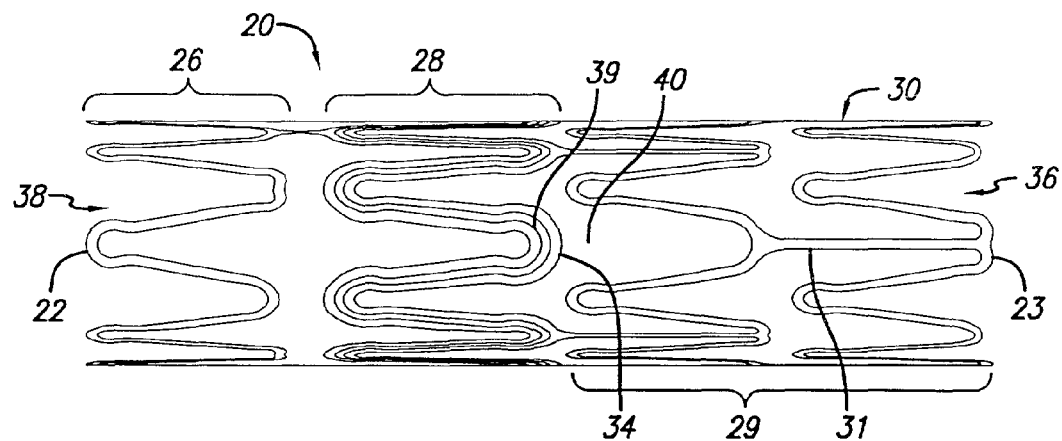
FIG. 14 is a partial elevational view of the stent of FIG. 13 in a cylindrical configuration and depicting an enlarged view of the nested ring portion.
Figure 15:
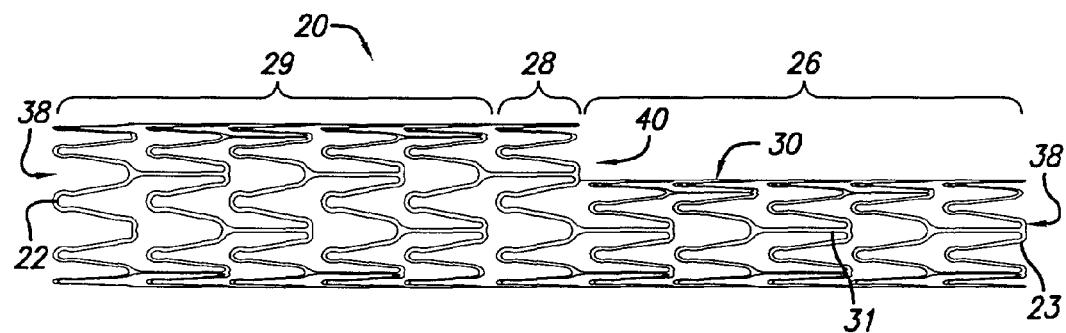
FIG. 15 is an elevational view depicting the central opening of the stent of the invention.
Figure 16:
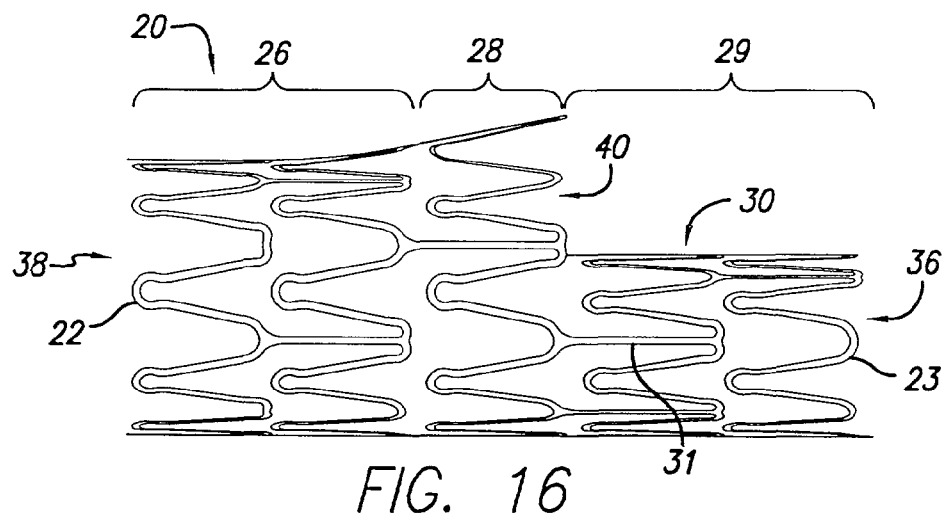
FIG. 16 is an enlarged partial elevational view of the stent of FIG. 15 depicting the central section and the central opening.
Figure 17:
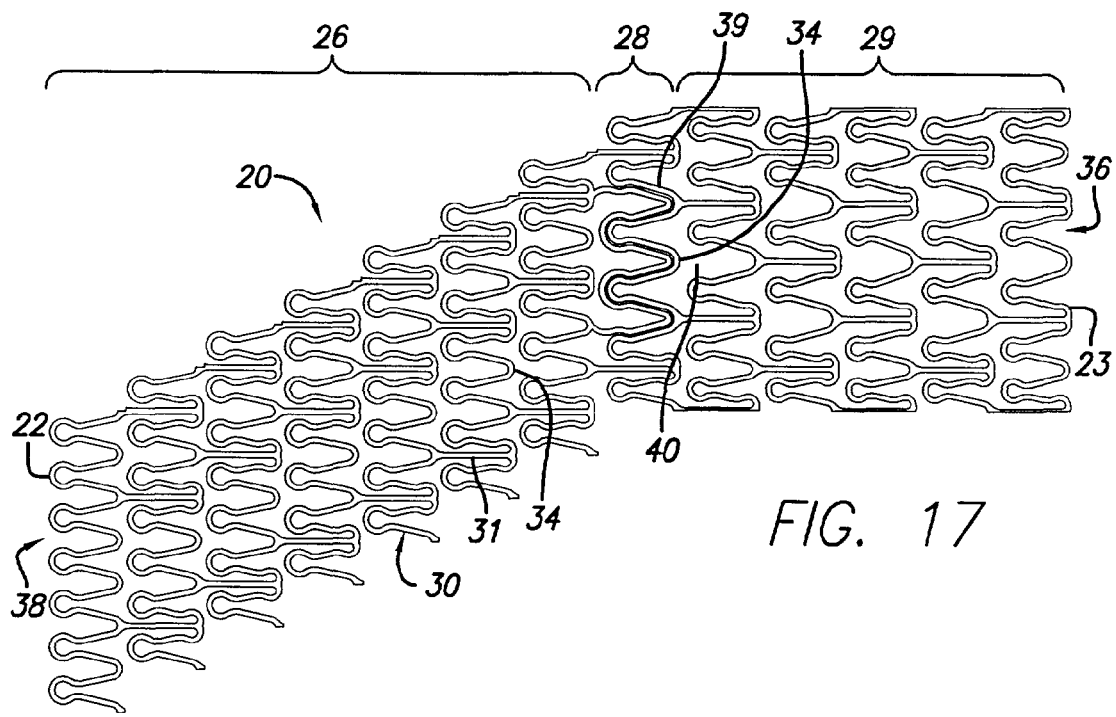
FIG. 17 is a flattened elevational view of one embodiment of the stent of the invention depicting a nested ring portion.
Figure 18:
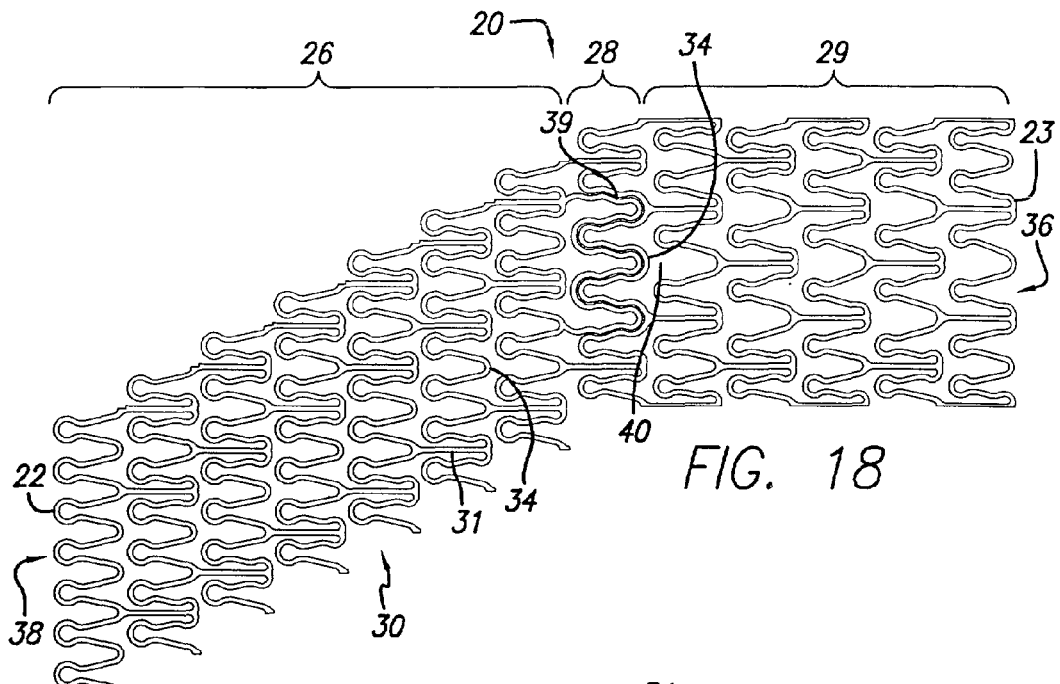
FIG. 18 is a flattened elevational view of one embodiment of the stent of the invention depicting a nested ring portion.
Figure 19:
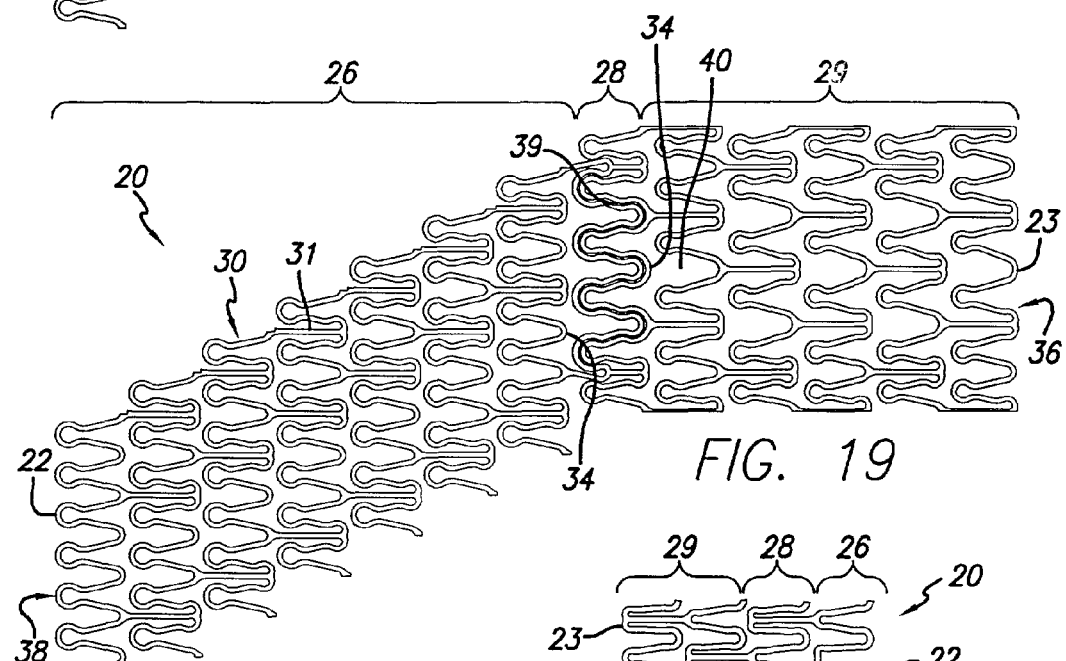
FIG. 19 is a flattened elevational view of one embodiment of the stent of the invention depicting a nested ring portion.
Figure 20:
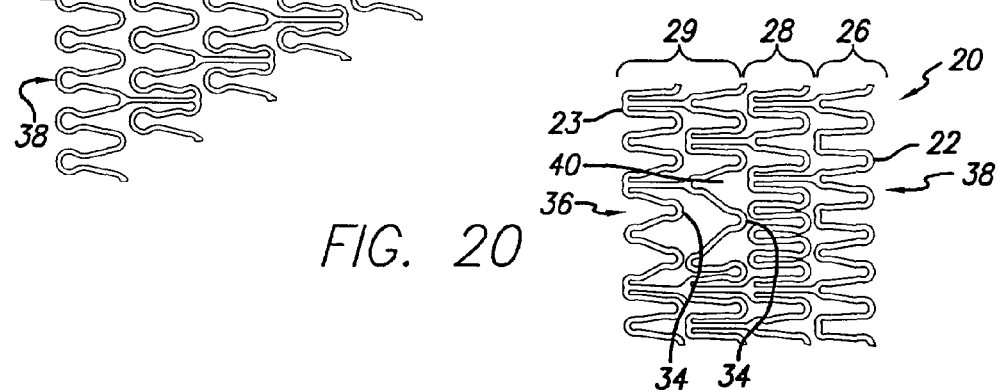
FIG. 20 is a flattened elevational view depicting one embodiment of the stent of the present invention.

In treating side branch vessel 5, if a prior art stent is used in which there is no acute angle at the proximal end of the stent to match the angle of the bifurcation, a condition as depicted in FIGS. 5A and 5B will occur. That is, a stent deployed in side branch vessel 5 will leave a portion of the side branch vessel exposed, or as depicted in 5B, a portion of the stent will extend into main vessel 6.

The stent of the present invention can be implanted in the main or side branch vessels to treat a number of disease configurations at a bifurcation, but not limited to, the following:

1. Treatment of a parent or main vessel and the origin of the side branch at a bifurcation with any angle associated between the side branch and parent vessel.
2. Treatment of a parent vessel proximal to the carina and the side branch vessel simultaneously.
3. Treatment of the proximal vessel extending only into the origin of the side branch and the origin of the distal parent at the bifurcation.
4. Treatment of the area at the bifurcation only.
5. The origin of an angulated posterior descending artery.
6. The origin of an LV extension branch just at and beyond the crux, sparing the posterior descending artery.
7. The origin of a diagonal from the left anterior descending.
8. The left anterior descending at, just proximal to, or just distal to the diagonal origin.
9. The origin of a marginal branch of the circumflex.
10. The circumflex at, just proximal to, or just distal to the marginal origin.
11. The origin of the left anterior descending from the left main.
12. The origin of the circumflex from the left main.
13. The left main at or just proximal to its bifurcation.
14. Any of many of the above locations in conjunction with involvement of the bifurcation and an alternate vessel.
15. Any bifurcated vessels within the body where conventional stenting would be considered a therapeutic means of treatment proximal or distal to the bifurcation.

The present invention solves the problems associated with the prior art devices by providing a stent which adequately covers the main branch vessel and extends partially into the side branch vessel to cover the origin of the side branch vessel as well. The invention also includes a stent delivery catheter assembly and the method of crimping the stent on the catheter and delivering and implanting the stent in the body, especially the coronary arteries.

The Stent Pattern

The stent pattern of the present invention is novel in that it provides for vessel wall coverage of the main branch vessel and at least partial coverage of the origin of the side branch vessel. More specifically, in FIGS. 6-20, several embodiments of trap-door stent 20 are shown. The stent is characterized as a "trap door" since the stent pattern is configured so that as the stent is expanded, a portion of the stent flares radially outwardly and opens to a greater diameter than the remainder of the stent, like a trap door, seemingly hidden until opened. The trap door portion, as will be further described herein, expands or opens to cover the opening to the side branch vessel. Once stent 20 is implanted in the main branch vessel and the opening to the side branch vessel, a second, conventional stent can be implanted in the side branch vessel, essentially abutting the trap door portion of the stent.

The intravascular stent 20 of the present invention is referred to as a "trap door" stent since the central portion of the stent is somewhat hidden during delivery and opens like a trap door to treat a bifurcated vessel when the stent is expanded. The stent of the present invention has a cylindrical body 21 that includes a proximal end 22 and a distal end 23. The stent has an outer surface 24 which contacts the vascular wall when implanted and an inner surface 25 through which blood flows when the stent is expanded and implanted. The stent can be described as having numerous connected rings 30 aligned along a common longitudinal axis of the stent. The rings are formed of undulating portions which include first peaks 34 that are configured to be spread apart to permit the stent to be expanded to a larger diameter or compressed tightly toward each other to a smaller diameter onto a catheter. The rings are connected to each other by at least one link 31 between adjacent rings. Typically, there are three links that connect adjacent rings and the links of one ring are circumferentially offset by about 60° from the links of an adjacent ring. While the links 31 typically are offset as indicated, this is not always the case, especially in the area of the trap door. Further, in order to enhance the expandability and the diameter of the ring or rings in the trap door area, long links 33 are about twice the length of the straight links 32. The number of links between adjacent rings does vary, however, in view of the trap door configuration.

The cylindrical body of the stent has a proximal section 26, a distal section 29 and a central section 28 where the proximal section can have between one and fifteen rings 30, the distal section can have between one and fifteen rings, and the central section will have between one and ten rings. The number of first peaks 34 in the central section generally will differ from the number of first peaks 34 in the proximal section and the distal section.

The central section 28 is essentially the trap door portion of the stent and is enlarged to appose the entrance to the side branch vessel when the stent is expanded. By way of example only, in one embodiment the rings 30 of the proximal section 26 have seven first peaks, the rings of the distal section 29 have six first peaks, and the rings of the central section 28 have eight first peaks. Thus, when expanded, the ring or rings of the central section will expand and the first peaks will spread apart to appose the entrance to the side branch vessel. The rings of the proximal section and distal section will expand into apposition with the walls of the main branch vessel. The number of peaks per section is a matter of choice depending upon the application and the type of bifurcated vessel to be treated. Each of the rings has at least one second peak 35, which is connected to link 31. The peaks are spaced on the rings in such a fashion as to provide uniformity after final expansion, since a bifurcated stent does not necessarily expand coaxially inside the vessel.

In one embodiment of the invention, a standard 18 mm-long stent 20 will have eight rings 30 in the proximal section 26, one ring in the central section 28, and six rings in the distal section 29. Each of the rings has a length that is substantially the same as the rest of the rings. In another embodiment, there is one ring in the proximal section, one ring in the central section, and one ring in the distal section. In this latter embodiment, the stent is much easier to navigate through a tortuous vessel because it is very short in its overall length (generally between about 2.0 mm to about 8.0 mm in overall length) and the distal end 23 of the stent tracks easily through the vessel in which it is to be implanted, such as a coronary artery. In addition, the short stent is more capable of rotating if it arrives at the bifurcation out of phase, whereby distal torque can be applied from the OTW and Rx guide wires to properly orient the stent.

A central opening 40 in the proximal section 26 of the stent allows the passage of a balloon contained on the delivery system. The stent is to be crimped tightly onto two separate expandable members of a catheter. Typically, and as will be described in more detail below, the expandable portions of the catheter will be balloons similar to a dilatation-type balloon for conventional dilatation catheters. In the present invention, the trap door stent 20 is configured such that the stent has a distal opening 36 and a proximal opening 38 that are in axial alignment and through which a longer balloon extends, and the central opening 40 which is adjacent the central section 28 or "trap door," through which a shorter balloon extends. The stent is crimped tightly onto both the long and short balloons as will be described.

In another embodiment, as shown in FIGS. 13-14 and 17-19, the ring 30 or rings in the central section 28 of the stent 20 have a corresponding set of nested peaks 39 nested within the first peaks 34 of the ring or rings of the central section. The nested peaks, when expanded, will appose the opening to the side branch vessel and provide additional support as well as vessel wall coverage. With the addition of the nested peaks, the central section can expand to an even greater diameter than a similar stent without the nested peaks because the extra peaks provide more material to expand.

With all of the embodiments of the trap door stent 20 disclosed herein, the rings 30 can be attached to each other by links 31 having various shapes, including straight links 32 or non-linear links 33 having curved portions. The non-linear links, as shown in FIG. 21, can have undulating portions 37 that are perpendicular (or offset) to the longitudinal axis of the stent and act as a hinge to enhance the flexibility of the stent. The links are not limited by any particular length or shape and can be a weld, laser fusion, or similar connection. Welds or laser fusion processes are particularly suited to stent patterns that are out of phase (the peaks point toward each other) as opposed to the in phase pattern (the peaks point in the same direction) shown in the drawings.

Figure 22A:
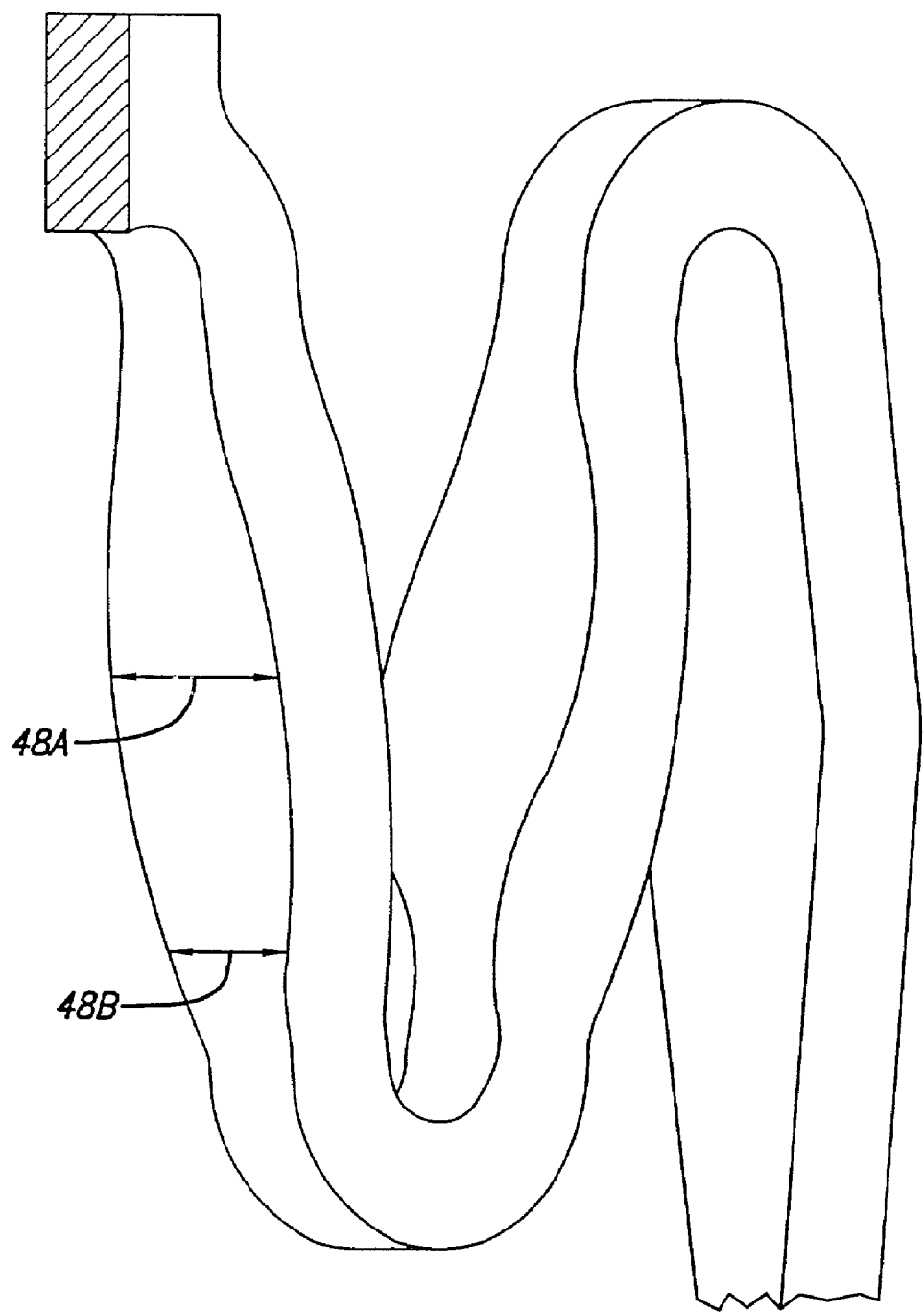
FIG. 22A is a portion of the stent pattern of the invention depicting struts of variable thickness.

Each embodiment of the stent 20 also can have rings 30 and links 31 that have variable thickness struts 48A and 48B, as shown in FIG. 22A, at various points in order to increase the radial strength of the stent, provide higher radiopacity so that the stent is more visible under fluoroscopy, and enhance flexibility in the portions where the stent has the thinnest struts. The stent also can have variable width struts 49A and 49B, as shown in FIG. 22B, to vary flexibility, maximize vessel wall coverage at specific points, or to enhance the stent radiopacity. The variable thickness struts or variable width struts, which may be more radiopaque than other struts, can be positioned along the stent to help the physician position the stent during delivery and implantation in the bifurcated vessel.

The trap door stent 20 can be formed in a conventional manner typically by laser cutting a tubular member or by laser cutting a pattern into a flat sheet, rolling it into a cylindrical body, and laser welding a longitudinal seam along the longitudinal edges of the stent. The stent can also be fabricated using conventional lithographic and etching techniques where a mask is applied to a tube or flat sheet. The mask is in the shape of the final stent pattern and is used for the purpose of protecting the tubing during a chemical etching process which removes material from unwanted areas. Electro-discharge machining (EDM) can also be used for fabricating the stent, where a mold is made in the negative shape of the stent and is used to remove unwanted material by use of an electric discharge. The method of making stents using laser cutting processes or the other described processes are well known. The stent of the invention typically is made from a metal alloy and includes any of stainless steel, titanium, nickel-titanium (NiTi or nitinol of the shape memory or superelastic types), tantalum, cobalt-chromium, cobalt-chromium-vanadium, cobalt-chromium-tungsten, gold, silver, platinum, platinum-iridium or any combination of the foregoing metals and metal alloys. Any of the listed metals and metal alloys can be coated with a polymer containing fluorine-19 ($^{19}$F) used as a marker which is visible under MRI. Portions of the stent, for example some of the links, can be formed of a polymer impregnated with $^{19}$F so that the stent is visible under MRI. Other compounds also are known in the art to be visible under MRI and also can be used in combination with the disclosed metal stent of the invention.

The stent of the invention also can be coated with a drug or therapeutic agent to assist in repair of the bifurcated vessel and may be useful, for example, in reducing the likelihood of the development of restenosis. Further, it is well known that the stent (usually made from a metal) may require a primer material coating to provide a substrate on which a drug or therapeutic agent is coated since some drugs and therapeutic agents do not readily adhere to a metallic surface. The drug or therapeutic agent can be combined with a coating or other medium used for controlled release rates of the drug or therapeutic agent. Examples of therapeutic agents that are available as stent coatings include rapamycin, actinomycin D (ActD), or derivatives and analogs thereof ActD is manufactured by Sigma-Aldrich, 1001 West Saint Paul Avenue, Milwaukee, Wis. 53233, or COSMEGEN, available from Merck. Synonyms of actinopmycin D include dactinomycin, actinomycin IV, actinomycin 11, actinomycin X1, andactinomycin C1. Examples of agents include other antiproferative substances as well as antineoplastic, antinflammatory, antiplatelet, anticoagulant, antifibrin, antithomobin, antimitotic, antibiotic, and antioxidant substances. Examples of antineoplastics include taxol (paclitaxel and docetaxel). Examples of antiplatelets, anticoagulants, antifibrins, and antithrombins include sodium heparin, low molecular weight heparin, hirudin, argatroban, forskolin, vapiprost, prostacyclin and prostacyclin analogs, dextran, D-phe-pro-arg-chloromethylketone (synthetic antithrombin), dipyridamole, glycoprotein, 11b/111a platelet membrane receptor antagonist, recombinant hirudin, thrombin inhibitor (available from Biogen), and 7E-3B® (an antiplatelet drug from Centocore). Examples of antimitotic agents include methotrexate, azathioprine, vincristine, vinblastine, fluorouracil, adriamycin, and mutamycin. Examples of cytostatic or antiproliferative agents include angiopeptin (a somatostatin analog from Ibsen), angiotensin converting enzyme inhibitors such as Captopril (available from Squibb), Cilazapril (available from Hoffman-LaRoche), or Lisinopril (available from Merck); calcium channel blockers (such as Nifedipine), colchicine fibroblast growth factor (FGF) antagonists, fish oil (omega 3-fatty acid), histamine antagonist, Lovastatin (an inhibitor of HMG-CoA reductase, a cholesterol lowering drug from Merck), monoclonal antibodies (such as PDGF receptors), nitroprusside, phosphodiesterase inhibitors, prostaglandin inhibitor (available from Glazo), Seramin (a PDGF antagonist), serotonin blockers, steroids, thioprotease inhibitors, triazolopyrimidine (a PDGF antagonist), and nitric oxide. Other therapeutic substances or agents which may be appropriate include alpha-interferon, genetically engineered epithelial cells, and dexamethasone.

It should be understood that any reference in the specification or claims to a drug or therapeutic agent being coated on the stent is meant that one or more layers can be coated either directly on the stent or onto a primer material on the stent to which the drug or therapeutic agent readily attaches.

The Stent Delivery Catheter Assembly

In keeping with the invention, as shown in FIGS. 23-28A, the stent 20 is mounted on catheter assembly 101 which has a distal end 102 and a proximal end 103. The catheter assembly includes a proximal shaft 104 which has a proximal shaft over-the-wire (OTW) guide wire lumen 105 and a proximal shaft inflation lumen 106 which extends therethrough. The proximal shaft OTW guide wire lumen is sized for slidably receiving an OTW guide wire. The inflation lumen extends from the catheter assembly proximal end where an indeflator or similar device is attached in order to inject inflation fluid to expand balloons or expandable members as will be herein described. The catheter assembly also includes a mid-shaft 107 having a mid-shaft OTW guide wire lumen 108 and a mid-shaft rapid-exchange (Rx) guide wire lumen 109. The proximal shaft OTW guide wire lumen 105 is in alignment with and an extension of the mid-shaft OTW guide wire lumen 108 for slidably receiving an OTW guide wire. The mid-shaft also includes a mid-shaft inflation lumen 110 which is in fluid communication with the proximal shaft inflation lumen 106 for the purpose of providing inflation fluid to the expandable balloons. There is an Rx proximal port or exit notch 115 positioned on the mid-shaft such that the Rx proximal port is substantially closer to the distal end 102 of the catheter assembly than to the proximal end 103 of the catheter assembly. While the location of the Rx proximal port may vary for a particular application, typically the port would be between 10 and 50 cm from the catheter assembly distal end 102. The Rx proximal port or exit notch provides an opening through which an Rx guide wire 116 exits the catheter and which provides the rapid exchange feature characteristic of such Rx catheters. The Rx port 115 enters the mid-shaft such that it is in communication with the mid-shaft Rx guide wire lumen 109.

The catheter assembly 101 also includes a distal Rx shaft 111 that extends from the distal end of the mid-shaft and which includes an Rx shaft Rx guide wire lumen 112, to the proximal end of the inner member 111A inside balloon 117. The distal Rx shaft 111 also contains an Rx shaft inflation lumen 114. The Rx shaft Rx guide wire lumen 112 is in alignment with the Rx guide wire lumen 109 for the purposes of slidably carrying the Rx guide wire 116. The Rx shaft inflation lumen 114 is in fluid communication with the mid-shaft inflation lumen 110 for the purposes of carrying inflation fluid to the long expandable member or long balloon.

The catheter assembly also contains an Rx inner member 111A that extends from the distal end of the distal Rx shaft 111 to the Rx shaft distal port 113. The Rx inner member 111A contains an Rx guide wire lumen 111B. The Rx inner member guide wire lumen 111B is in alignment with the Rx shaft Rx guide wire lumen 112 for the purpose of slidably carrying the Rx guide wire 116. The Rx guide wire will extend through the Rx proximal port 115 and be carried through Rx guide wire lumen 109 and Rx shaft Rx guide wire lumen 112, and through Rx guide wire lumen 111B and exit the distal end of the catheter assembly at Rx shaft distal port 113.

The catheter assembly further includes a long balloon 117 positioned adjacent the distal end of the catheter assembly and a distal tip 118 at the distal end of the Rx shaft. Further, a coupler 119 is associated with distal Rx shaft 111 such that the Rx shaft Rx guide wire lumen 112 extends through the coupler, with the distal port 113 being positioned at the distal end of the coupler. The coupler has an Rx guide wire lumen 120 that is an extension of and in alignment with Rx lumen 111B. The coupler 119 further includes a blind lumen 121 for receiving and carrying an OTW guide wire (or joining mandrel) 125. The blind lumen includes a blind lumen port 122 for receiving the distal end of the OTW guide wire (or joining mandrel) 125 and a dead-end lumen 124 positioned at the coupler distal end 123. The coupler blind lumen 121 will carry the distal end of a guide wire (either the distal end of the OTW guide wire (or joining mandrel) 125 or an Rx guide wire (or joining mandrel) 116 as will be further described herein) during delivery of the catheter assembly through the vascular system and to the area of a bifurcation. The blind lumen is approximately 3 to 20 mm long, however, the blind lumen can vary in length and diameter to achieve a particular application or to accommodate different sized guide wires having different diameters. Since the coupler moves axially relative to the shaft it is not connected to, the guide wire that resides in the blind lumen 121 of the coupler slides axially relative to the coupler during delivery of the catheter assembly through the vascular system and tortuous anatomy so that, additional flexibility is imported to the tips making it easier to track through tortuous circuitry. A distance "A" should be maintained between the distal end 126 of the OTW guide wire 125 and the dead end 124 of the blind lumen. The distance "A" can range from approximately 0.5 to 5.0 mm, however, this range may vary to suit a particular application. Preferably, distance "A" should be about 0.5 mm to about 2.0 mm.

In further keeping with the invention, the catheter assembly 101 also includes an OTW shaft 128 which extends from the distal end of mid-shaft 107. The OTW shaft carries a short balloon 129 that is intended to be shorter than long balloon 117 and positioned substantially adjacent to the long balloon. As is shown in FIG. 23, the two balloons 117, 129 are adjacent to one another and more accurately, are arranged laterally adjacent to one another. Such relationship is more commonly referred to as "side by side" and is not to be confused with an end to end configuration. Rather than sharing a common longitudinal axis, the longitudinal axis of one balloon is spaced apart from the longitudinal axis of the other balloon wherein the two axes are arranged substantially parallel to one another. The OTW shaft 128 also includes an OTW lumen 130 that is in alignment with the mid-shaft OTW guide wire lumen 108 and proximal shaft OTW guide wire lumen 105. Thus, an OTW lumen extends from one end of the catheter assembly to the other and extends through the OTW shaft 128. An OTW shaft distal port 131 is at the distal end of the OTW lumen 130 and the OTW shaft 128 also includes an OTW shaft inflation lumen 132. Inflation lumen 132 is in alignment and fluid communication with inflation lumens 110 and 106 for the purpose of providing inflation fluid to the long balloon 117 and the short balloon 129. In this particular embodiment, an OTW guide wire 125 would extend from the proximal end 103 of the catheter assembly and through proximal shaft OTW guide wire lumen 105, mid-shaft OTW guide wire lumen 108, OTW lumen 130 and out distal port 131 where it would extend into the coupler 119, and more specifically into blind lumen 121 through blind lumen port 122.

In order for the catheter assembly 101 to smoothly track and advance through tortuous vessels, it is preferred that the OTW lumen 130 be substantially aligned with the blind lumen 121 of coupler 119. In other words, as the OTW guide wire extends out of the OTW lumen 130, it should be aligned without bending more than about ±10° so that it extends fairly straight into the coupler blind lumen 121. If the OTW lumen 120 and the coupler blind lumen 121 are not substantially aligned, the pushability and the trackability of the distal end of the catheter assembly may be compromised and the physician may feel resistance as the catheter assembly is advanced through tortuous vessels, such as the coronary arteries.

In an alternative embodiment, as will be explained more fully herein, a mandrel (stainless steel or nickel titanium wire is preferred) resides in the OTW guide wire lumens 105,108, 130, and extends into blind lumen 121. The mandrel is used in place of an OTW guide wire until the catheter assembly has been positioned near the bifurcated vessel, at which time the mandrel can be withdrawn from the vascular system and the OTW guide wire advanced through the OTW guide wire lumens to gain access to the side branch vessel. This will be described more fully in the section related to delivering and implanting the stent.

The catheter assembly 101 of the present invention can be dimensioned for various applications in a patient's vascular system. Such dimensions typically are well known in the art and can vary, for example, for various vessels being treated such as the coronary arteries, peripheral arteries, the carotid arteries, and the like. By way of example, the overall length of the catheter assembly for treating the coronary arteries typically is approximately 135 to 150 cm. Further, for stent delivery in the coronary arteries at a bifurcated vessel, the working surface or the stent carrying surface of the long balloon 117 can be about 18.5 mm for use with an 18 mm-long stent. The short balloon 129 typically will be about 6 to 9 mm, depending on the type of trap door stent 20 that is being implanted. The lengths of the various shafts, including proximal shaft 104, mid-shaft 107, distal Rx shaft 111, and OTW shaft 128 are a matter of choice and can be varied to suit a particular application.

FIGS. 23A-23E illustrate an alternative embodiment of the bifurcated catheter assembly 101 which is configured to inflate the expandable portion or balloons either simultaneously or independently. For example, it may be advantageous to partially inflate the balloon in the main vessel and to fully inflate the balloon in the side branch vessel to avoid plaque shifting or to make sure that the central opening in the stent is fully opened and covers the opening to the side branch vessel. The present invention catheter assembly provides for independent balloon inflation and is shown in FIGS. 23A-23E. The reference numbers are primed to indicate like structure shown in FIGS. 23-27. The description of the catheter assembly set forth in FIGS. 23A-23E is essentially the same as for FIGS. 23-27 except for the independent inflation lumen and associated structure which is described as follows.

As shown in FIGS. 23A-23E, an inflation lumen 135' is located at the distal end of catheter assembly 101' and extends from the proximal end of the catheter into the proximal shaft 104. Inflation lumen 135' will connect to either inflation lumen 106A' or inflation lumen 106B', and it is a matter of choice as to which inflation lumen 106A' or 106B' is used. Inflation lumen 135' has a proximal port 136' that will be in fluid communication with an inflation source such as an indeflator. The other inflation port 137' will connect to a separate inflation source so that independent inflation occurs between ports 136' and into inflation lumen 135' and 137' which connects into either inflation lumen 106A' or inflation lumen 106B', whichever one is not connected to inflation lumen 135'. Inflation lumens 106A' and 106B' are in fluid communication with lumens 110A' and 110B' respectively and extend through mid-shaft section 107' and split, one extending into the Rx shaft 111' and the other extending into the OTW shaft 128'. With the inflation lumen separated, the long balloon 117' can be inflated independently of short balloon 129'. Alternatively, the balloons can be inflated simultaneously, or they can be inflated independently at different pressures, depending upon a particular application.

In an alternative embodiment of the independent inflation catheter 101' of FIGS. 23A-23E, both guide wires within the catheter assembly extend proximally to the catheter proximal end 103' and function as OTW guide wires. In this embodiment, lumen 135' is an OTW guide wire lumen and is in communication with lumen 106B' of the proximal section of the catheter 104'. Guide wire lumen 106B' is then in communication with either lumens 108' or 109' in the mid-section of the catheter and extends distally to tip branch 111A'. Guide wire 125' extends from the catheter proximal end through lumen 106A' in the proximal section of the catheter 104' and into lumen 108' or 109' whichever is not occupied by the other OTW guide wire previously described. Wire 125' then extends distally into lumen 130' located in branch 128' and into the coupler 122' to join the two tips.

As shown in FIG. 28A, radiopaque markers 135 are placed on the catheter assembly to help the physician identify the location of the distal end of the catheter in relation to the target area for stent implantation. While the location of the radiopaque markers is a matter of choice, preferably the long balloon 117 will have three radiopaque markers on the inner shaft of the guide wire lumen 112 and the short balloon 129 will have one radiopaque marker on the inner member of the OTW guide wire lumen 130. Preferably, the middle radiopaque marker on the inner shaft of the long balloon is aligned with the opening of the trap door. One or more of the radiopaque markers may coincide with the alignment of the stent on the balloons which will be described more fully herein.

FIG. 29 illustrates another embodiment of a bifurcated catheter 140 which embodies features of the invention. As with catheter 101, the bifurcated catheter 140 can be used for a variety of procedures such as dilatation, drug delivery, and delivering and deploying a stent, including a stent of the invention, in a body lumen. Bifurcated catheter 140 generally comprises an elongated shaft 142 having a proximal shaft section 144 with a first inflation lumen 146, and a multifurcated distal shaft section 148 with a first branch 150 and at least a second branch 152. The first branch 150 has a second inflation lumen 154 within at least a portion thereof in fluid communication with the first inflation lumen 146 and the second branch 152 has a third inflation lumen 156 within at least a portion thereof in fluid communication with the first inflation lumen 146. An intermediate shaft section 158 joins the proximal and distal sections together and defines a fourth inflation lumen 160 in fluid communication with the first, second, and third inflation lumens 146/154/156. A joining wire lumen 162 extends within the proximal section, the intermediate section, and the first branch 150 of the multifurcated distal section 148. The guide wire lumen 164 extends within the intermediate section 158 and the second branch 152 of the multifurcated distal section 148. A guide wire lumen 164 extends within the intermediate section 158 and the second branch 152 of the multifurcated distal section 148. A first balloon 166 is on the first branch 150 and a second balloon 168 is on the second branch 152, with interiors in fluid communication with the inflation lumens. An adapter 169 on the proximal end of the catheter is configured to direct inflation fluid into the inflation lumens and to provide access to joining wire lumen 162. A coupler 170 on the second branch, distal to the second balloon 168, is configured for releasably coupling the first and second branches 150/152 together to form a coupled configuration, as discussed in more detail below. The bifurcated catheter 140 is illustrated in the coupled configuration in FIG. 29.

In the embodiment illustrated in FIG. 29, the joining wire lumen 162 is defined by a first inner tubular member 172, and the guide wire lumen 164 is defined by a second inner tubular member 174. In a presently preferred embodiment, the first inner tubular member 172 is formed of a single tubular member, which may comprise one or more layers as is conventionally known in the art. However, in alternative embodiments, the first inner tubular member 172 may be formed of separate longitudinal members joined together, end to end, along the length of the first inner tubular member 172. Similarly, the second inner tubular member 174 is preferably a single or multi-layered, single tubular member, although a plurality of separate members may be joined together to form the second inner tubular member 174.

Figure 30:
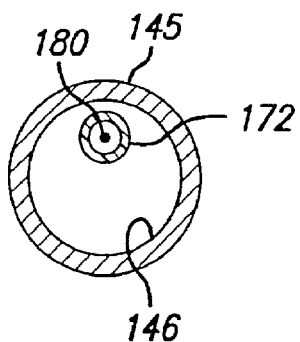
FIG. 30 is a transverse cross-sectional view taken along lines 30-30 depicting the proximal shaft section of the catheter.
Figure 31:
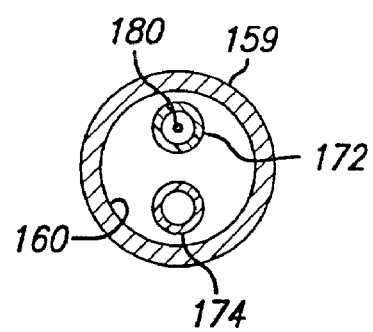
FIG. 31 is a transverse cross-sectional view taken along lines 31-31 depicting the mid or intermediate shaft section of the catheter.
Figure 31A:
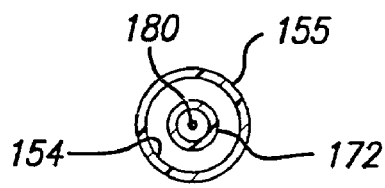
FIG. 31A is a transverse cross-sectional view taken along lines 31A-31A depicting the first distal outer member.
Figure 31B:
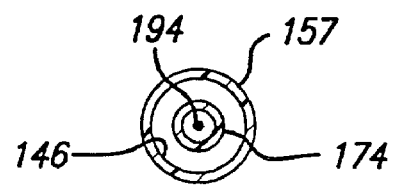
FIG. 31B is a transverse cross-sectional view taken along lines 31B-31B depicting the second distal outer member.
Figure 32:
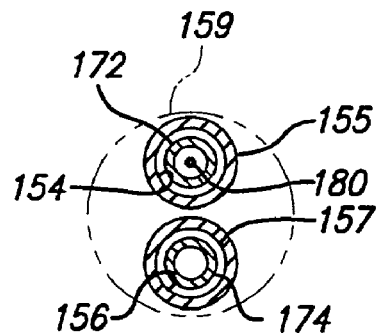
FIG. 32 is a transverse cross-sectional view taken along lines 32-32 depicting the multifurcated distal section of the catheter.

FIGS. 30-32 illustrate transverse cross sections of the catheter illustrated in FIG. 29, taken along lines 30-30, 31-31, and 32-32, respectively. In the embodiment illustrated in FIG. 29, the proximal shaft section 144 comprises a proximal outer tubular member 145 defining the first inflation lumen 146, as best illustrated in FIG. 30. Similarly, the first branch 150 of the multifurcated distal shaft section 148 is formed in part by a first distal outer tubular member 155, and the second branch 152 is formed in part by a second distal outer tubular member 157. The intermediate shaft section 158 comprises an intermediate outer tubular member 159 defining the fourth inflation lumen 160. In the embodiment illustrated in FIG. 29, the intermediate outer tubular member is a separate tubular member secured to the distal end of the proximal outer tubular member. However, in alternative embodiments, the intermediate section 158 (or intermediate outer tubular member) may be an integral, one piece unit with the proximal section 144, formed by a distal end portion of the proximal section 144. In a presently preferred embodiment, the distal end of the proximal outer tubular member 145 is tapered to form a truncated distal end which provides improved kink resistance, pushability, and a smooth junction transition. The tapered distal end of the proximal outer tubular member is preferably formed by cutting the end at an angle to form a truncated end. In one embodiment the taper is about 4 to about 10 mm in length. In a presently preferred embodiment, the proximal end of the intermediate outer tubular member 159 is expanded or flared to allow the proximal end to overlap around the outer surface of the distal end of the proximal outer tubular member 145. The intermediate outer tubular member 159 has a single distal end as illustrated in FIG. 29, which is disposed about both the proximal end of the first distal outer tubular member 155 and the proximal end of the second distal outer tubular member 157. The first inner tubular member 172 and the second inner tubular member 174 extend within the fourth inflation lumen 160 in the intermediate outer tubular member 159 in a side-by-side, radially spaced apart relation, as illustrated in FIG. 31. In the embodiment illustrated in FIG. 31, the intermediate outer tubular member 159 has a circular transverse cross sectional shape. In an alternative embodiment, the intermediate outer tubular member 159 has an oblong transverse cross sectional shape (not shown). FIGS. 31A and 31B detail the structure of first and second outer tubular members 155 and 157 respectively. Inner tubular member 172, which carries joining wire 180, is in coaxial relationship with first distal outer tubular member 155, with inflation lumen 154 between the two shaft members. Similarly, inner tubular member 174, which carries guide wire 194, is in coaxial relationship with second distal outer tubular member 157, with inflation lumen 146 between the two shaft members. As shown in FIG. 32, which illustrates the multifurcated distal shaft section with the proximal view of the intermediate tubular member 159 shown in phantom, the first inner tubular member 172 is coaxially disposed in the first distal outer tubular member 155, and second inner tubular member 174 is coaxially disposed in the second distal outer tubular member 157. The first inner tubular member 172 is configured as an OTW member, to slidably receive a joining wire 180 or guide wire in the joining wire lumen 162 therein, with the distal end of the joining wire extending out the port and into the distal end of the first branch 152 and into the coupler 170 to form the coupled configuration. The joining wire 180 is preferably a flexible, typically metal, member. In one embodiment, the joining wire 180 comprises a guide wire, and preferably a guide wire having a distal tip coil configured for use in crossing chronic total occlusions and which consequently provides a desired level of stiffness for improved retractability of the joining wire 180 proximally into the joining wire lumen 162 during uncoupling of the first and second branches 150/152. The joining wire 180 preferably performs similar to a guide wire by providing support at the proximal end of the catheter 140 and the ability to track the patient's tortuous anatomy. In one embodiment, the joining wire 180 has a proximal section with a 0.014 inch outer diameter, and two tapered sections distal thereto tapering to a smaller outer diameter, providing a smooth distal transition. In a presently preferred embodiment, the joining wire 180 has a soft distal tip comprising a polymeric tube (not shown) around the distal end of the wire 180. The polymeric tube, preferably formed of a polyether block amide adhesively bonded to the distal end of the joining wire 180, provides an a traumatic distal end and improved, secure placement of the distal end of the joining wire 180 in the coupling lumen 184 of the coupler 170, discussed below. The second inner tubular member 174 is configured as an Rx member, to slidably receive a guide wire (not shown) in the guide wire lumen 164 therein. The second inner tubular member 174 has a proximal end which is located at the intermediate section 158, with the guide wire lumen 164 therein extending between and in fluid communication with a distal port in the distal end of the second branch 152 and a proximal port in a side wall of the intermediate outer tubular member 159. The proximal port in the intermediate outer tubular member 159 is spaced a relatively short distance from the distal end of the second branch and a relatively long distance from the proximal end of the catheter. Although the proximal end of the guide wire lumen 164 is at the intermediate section 158 in the presently preferred embodiment, in alternative embodiments, the proximal end of the guide wire lumen may be at locations other than the intermediate section, such as within the proximal section 144 or within the second branch 152 of the multifurcated distal section 148.

Coupler 170 is shown in more detail in FIG. 33, illustrating an enlarged, longitudinal cross-sectional view of the distal end of the second branch 152 of the catheter illustrated in FIG. 29, taken within circle 33. The coupler 170 comprises a tubular sleeve disposed around at least a section of the second inner tubular member 174. A coupling lumen 184 is defined at least in part by the tubular sleeve, and is configured to slidably receive the distal end of the joining wire 180, to thereby releasably couple the first and second branches 150/152 together. In the embodiment illustrated in FIG. 33, the coupling lumen 184 is a blind lumen having a closed distal end and an open proximal end. In the illustrated embodiment, the coupler is formed by placing a polymeric tubular sleeve, which has a uniform inner lumen extending from the proximal end to the distal end thereof, over the distal end of the second inner tubular member, with a mandrel on one side of second tubular member between an inner surface of the tubular sleeve and an outer surface of the second outer tubular member. The mandrel has a distal taper in order to form the distal taper of the coupler 185. The tubular sleeve is preferably fusion bonded to the second inner tubular member by applying heat and optionally a radially contracting force. The mandrel is then removed, to thereby form the coupling lumen 184. As a result, the coupling lumen 184 is at least in part defined by an outer surface of the inner tubular member 174 and an inner surface of the tubular sleeve 170. Thus, the coupling lumen 184 is defined in part by a radially enlarged distal portion of the inner lumen of the tubular sleeve 170 in which the second inner tubular member is disposed. In alternative embodiments, the coupler 170 may comprise a single lumen extrusion secured in parallel to the distal end of the guide wire lumen 164 at the distal end of the second branch 152, two single lumen extrusions with one extruded lumen defining the coupling lumen 184 and bonded to the second extruded lumen which is disposed around the distal end of the tubular member defining the guide wire lumen 164 at the distal end of the second branch 152, a dual lumen extrusion with the first lumen defining the coupling lumen 184 and the second lumen either defining the distal end of the guide wire lumen 164 or disposed around the distal end of the tubular member defining the guide wire lumen 164 at the distal end of the second branch 152, or a lumen created in the tubular member defining the guide wire lumen 164 at the distal end of the second branch 152. In the embodiment illustrated in FIG. 29, the section of the second inner tubular member 174 disposed in the tubular sleeve 170 has an outer diameter not greater than an outer diameter of a section of the second inner tubular member proximally adjacent to the tubular sleeve 170.

The location of the distal end of the first branch 150 relative to the coupler 170 on the second branch 152 is selected to provide improved catheter performance, such as improved advanceability of the catheter through the tortuous anatomy, and improved retractability of the joining wire 180 proximally into the joining wire lumen 162. Specifically, the distal end of the first branch 150 is proximally spaced from a distal port of the coupling lumen 184 to avoid disadvantageous affects on advanceability of the catheter around turns in the body lumen which are caused by the first branch 150 being too far distally forward. However, the distal end of the first branch 150 is distally spaced from the second balloon 168 working length to avoid having a disadvantageously long length of joining wire 180 exposed and unsupported between the first and second branches 150/152. In the illustrated embodiment, in the coupled configuration, the distal end of the first branch is radially aligned with a proximal section of the coupler 170.

In another embodiment, the distal end of the tubular sleeve 170 is proximal to the distal end of the second branch. In the embodiment illustrated in FIG. 29, a distal tip member 186 defining a lumen is secured (preferably butt joined) to the distal end of the first inner tubular member 172 and forms the distal end of the first branch 150, and a distal tip member 188 defining a lumen is secured (preferably butt joined) to the distal end of the second inner tubular member 174 and forms the distal end of the second branch 152. The distal tip members 186/188 are typically tubular members formed of a relatively low durometer polymeric material to provide a soft, a traumatic distal tip. The tubular sleeve 170 is thus disposed about and secured to a distal section of the second inner tubular member 174 and a proximal section of the distal tip member 188. Consequently, in the embodiment illustrated in FIG. 33, the coupling lumen 184 is defined by an outer surface of the distal section of the second inner tubular member 174, an outer surface of the proximal section of the distal tip member 188, and an inner surface of the tubular sleeve 170.

The first balloon 166 on the first branch 150 has a proximal end sealingly secured to a distal section of the first distal outer tubular member 155, and a distal end sealingly secured to a distal section of the first inner tubular member 172, so that the first balloon 166 can be expanded by delivery of inflation medium to the interior of the first balloon 166 from the second inflation lumen 154. Similarly, second balloon 168 on the second branch 152 has a proximal end sealingly secured to a distal section of the second distal outer tubular member 157, and a distal end sealingly secured to a distal section of the second inner tubular member 174, so that the second balloon 168 can be expanded by delivery of an inflation medium to the interior of the second balloon 168 from the third inflation lumen 156. In the embodiment illustrated in FIG. 29, the first and second balloons 166/168 are both in fluid communication with a common proximal inflation lumen (e.g., the first inflation lumen 146), and thus are not inflated separate from one another. However, in alternative embodiments, separated or valved inflation lumens may be present to provide for independent inflation of the first and second balloons 166/168, so that the first inflation lumen 146 is in fluid communication with at least one of the second and third inflation lumens 154/156. In one embodiment, the first balloon 166 has a shorter length than the second balloon 168, and an elongated proximal tapered section having a length not less than a length of the cylindrical working length of the first balloon 166, for improved stent delivery in a main branch vessel and at the opening of a side branch vessel. In another embodiment, the length of the elongated proximal tapered section of the first balloon 166 is greater than the length of the cylindrical working length of the first balloon 166, and in one embodiment is about 5 to about 7 mm, preferably about 6 mm. However, a variety of suitable balloon sizes and configurations may be used depending on the application. Specifically, the configuration of the proximal tapered section of the first balloon 166 will vary depending on the shape of the patient's bifurcated vessel. Although illustrated as two separate balloons, it should be understood that in an alternative embodiment the first and second balloons 166/168 may comprise a bifurcated balloon (not shown) on the multifurcated distal shaft section 148. In the embodiment illustrated in FIG. 29, the first balloon 166 has an elongated proximal skirt section, with the proximal end of the first balloon 166 being radially aligned with a proximal section of the second balloon 168, in the coupled configuration. Preferably, the proximal end of the first balloon 166 is radially aligned with the junction between the proximal tapered section and the proximal skirt section of the second balloon 168, which are proximal to the working length of the second balloon 168. A variety of suitable balloon configurations can be used for the second balloon 168, including conventional stent delivery balloons, and the balloon having multiple tapered sections disclosed in U.S. Pat. No. 6,200,325, incorporated in its entirety by reference herein.

Although the first and second balloons 166/168 are illustrated in FIG. 29 in an inflated configuration with the joining wire 180 disposed in the coupling lumen 184, it should be understood that in use, the joining wire 180 is typically retracted proximally out of the coupling lumen 184 and into the joining wire lumen 162 before inflation of the balloons 166/168. Additionally, the joining wire 180 is typically releasably secured in place in the bifurcated catheter 140 during advancement of the catheter 140 in the patient's vasculature, preferably by locking a proximal portion of the joining wire 180 to the catheter 140. In one embodiment, a locking member (not shown), is provided on the proximal end of the catheter 140 to releasably lock the joining wire 180 in place. The locking member preferably comprises a modified Touhy Borst adapter having a body which screws onto the proximal adapter 169 at the guide wire port thereof, such that silicon tubing inside the locking member compresses onto the joining wire 180, and a cap which is screwed onto the body of the locking member. The proximal end of the joining wire 180 is then trimmed flush with the cap of the locking member, and an adhesive is used to fill the cap hole to provide securing of the joining wire 180. Subsequent to securing the joining wire 180 in place, a plastic tamper-proof seal may be provided over the body of the locking member and the guide wire port of the proximal adapter 169 to ensure that the joining wire 180 remains in place before use.

FIG. 29 illustrates expanded stent 20, in dashed lines, mounted on the first and second balloons 166/168, to form a catheter assembly. The method of deploying the stent 20 at a bifurcated body lumen of a patient is similar to the method disclosed herein for the embodiment of the catheter assembly 101. Generally, the catheter 140 in the coupled configuration is introduced into the patient's body lumen and advanced therein, typically over a guide wire already in position in the lumen. Specifically, the proximal end of the guide wire extending outside of the body lumen is introduced into the distal end of the guide wire lumen 164, and the catheter 140 advanced over the guide wire until the distal end of the catheter is in a desired location at the body lumen bifurcation. The joining wire 180 is then proximally retracted from the coupling lumen 184 to uncouple the first and second branches 150/152. The catheter is then advanced over the guide wires to position the stent at the bifurcation. The first and second balloons 166/168 are inflated to expand the stent 20 in the main branch vessel and at the opening to the side branch vessel. The first and second balloons 166/168 are deflated and the catheter 140 withdrawn, leaving the stent 20 implanted in the body lumen. A second stent can be implanted in the side branch vessel, as discussed herein.

In the embodiment illustrated in FIG. 29, three radiopaque marker bands are provided on the second inner tubular member 174, to facilitate positioning the distal end of the catheter 140 in place in the patient's vasculature. In an alternative embodiment (not shown), a single radiopaque marker is provided on the first or second inner tubular member 172 or 174 as a carina marker band. The single radiopaque marker is secured to the first or second inner tubular member 172 or 174, preferably by adhesive bonding or crimping, such that it is aligned with the proximal end of the first balloon 166 or preferably aligned on the trap door opening of the stent. The single radiopaque marker provides improved manufacturability and flexibility compared to multiple markers.

Bifurcated catheter 140 is similar in many respects to the catheter assembly 101 disclosed herein, and it should be understood that the disclosure and individual features of the bifurcated catheter 140 and catheter assembly 101 discussed and illustrated with respect to one of the embodiments applies to the catheter assembly 101 discussed and illustrated with respect to one of the embodiments applies to the other embodiment as well. To the extent not discussed herein, the various components of catheter 140 can be formed of conventional materials used in the construction of catheters, and joined together using conventional methods such as adhesive bonding and fusion bonding. In one embodiment, the proximal outer tubular member is formed of a relatively high strength material such as a relatively stiff nylon material or a metal hypotube. The intermediate tubular member and distal outer tubular members are preferably formed of a polymeric material including polyamides such as nylon or urethanes. The inner tubular members preferably have at least an outer layer which is fusion bondable (i.e., compatible) with the polymeric material of the balloons and the coupler. In one embodiment, the coupler and distal tip members are formed of a polyamide such as polyether block amide (PEBAX) or blend thereof.

The materials used to construct the catheter assembly 101 or 140 are known in the art and can include for example various compositions of PEBAX, PEEK (polyetherketone), urethanes, PET or nylon for the balloon materials (polyethylene terephathalate) and the like. Other materials that may be used for the various shaft constructions include fluorinated ethylene-propylene resins (FEP), polytetrafluoroethylene (PTFE), fluoropolymers (Teflon), Hytrel polyesters, aromatic polymers, block co-polymers, particularly polyamide/polyesters block co-polymers with a tensile strength of at least 6,000 psi and an elongation of at least 300%, and polyamide or nylon materials, such as Nylon 12, with a tensile strength of at least 15,000 psi. The various shafts are connected to each other using well known adhesives such as Loctite or using heat-shrink tubing over the joint of two shafts, of which both methods are well known in the art. Further, any of the foregoing catheter materials can be combined with a compound that is visible under MRI, such as $^{19}F$, as previously discussed herein.

The Stent Crimping Method

Since the present invention stent and catheter assembly are used in bifurcated vessels, and most likely in bifurcations occurring in the coronary arteries, the stent must be tightly crimped onto the catheter assembly during delivery so that the stent remains firmly in place until the balloons are expanded thereby implanting the stent at the site of the bifurcation. Due to the unique and novel design of trap door stent 20, and the particular balloon arrangement of a long balloon 117 and a short balloon 129, the apparatus and method of crimping are unique.

Figure 34:
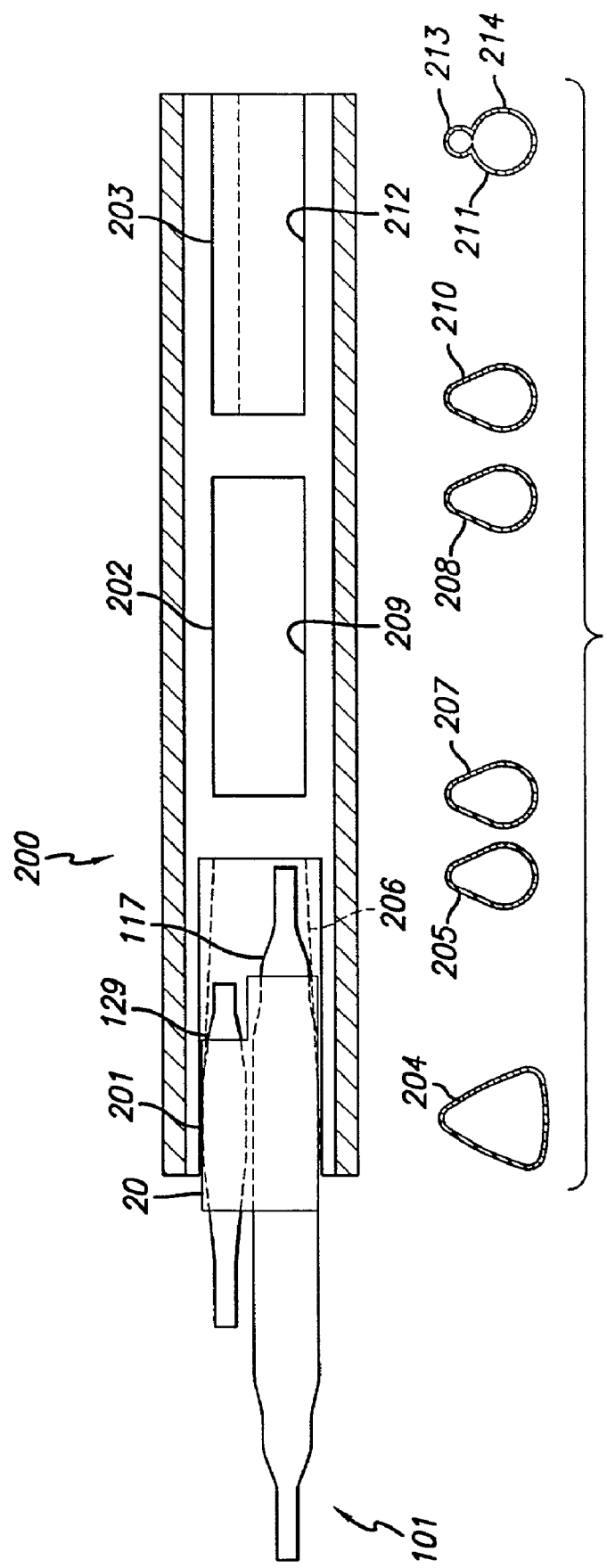
FIG. 34 is an elevational view and a partial longitudinal cross-sectional view of the crimping mold assembly.

In keeping with the invention a crimping assembly or mold assembly 200 is provided in order to tightly crimp the stent 20 onto the catheter assembly 101, and more particularly onto long balloon 117 and short balloon 129. As illustrated in FIG. 34, the mold assembly preferably has three sections, tapered section 201, straight section 202, and finish section 203, through which the stent mounted on the balloons is advanced for the purpose of crimping or compressing the stents onto the balloons. While in the preferred embodiment there are three sections used to compress the stent, more or fewer sections may be appropriate to suit a particular application. With respect to tapered section 201, it includes a first end 204 shown by way of cross-section immediately under the tapered section depicted in FIG. 34. The tapered section also has second end 205 and a tapered lumen 206 such that the lumen created by first end 204 is larger than the lumen created by second end 205. The lumen created by first end 204 is large enough to accommodate the catheter assembly with the stent premounted on the long balloon 117 and the short balloon 129. The premounting procedure can include slightly compressing the stent onto the balloons using the operator's fingers to lightly compress the stent so that it remains on the balloons prior to insertion into the mold assembly. As the catheter assembly with the stent mounted on the balloon is advanced from left to right in FIG. 34, the tapered lumen 206 progressively compresses the stent onto the two balloons and begins to shape the stent into the cross-section shown at second end 205. The stent and balloons are then advanced into straight section 202 which has a first end 207 and a second end 208 that have identical cross-sectional configurations. As the stent and balloons are advanced through straight lumen 209, the stent is uniformly compressed and any unevenness created by the tapered lumen 206 is removed, thereby providing a smooth and uniform stent outer surface having a configuration shaped like the lumen defined by second end 208. The stent and balloons are then advanced from left to right in FIG. 34 through finish section 203. Finish section 203 has a first end 210 that has substantially the same cross-sectional shape as the second end 208 of straight section 202. As the stent and balloons are advanced through finish section 203, they are progressively compressed or crimped into the cross-sectional configuration of second end 211. The finish lumen 212 gradually and progressively (moving left to right) compresses the stent onto the balloons from the cross-sectional shape of first end 210 into the cross-sectional shape of second end 211. The catheter is advanced such that the proximal portion of the stent up through the trap door resides in section 202 and the portion of the stent and catheter distal to the trap door reside in section 203. Sections 202 and 203 are shaped to accommodate the natural shape of the catheter and balloons as they change along their lengths. The balloons can be pressurized and the molds heated while the balloons (and stent) and catheter are constrained in the mold in order to compress the stent into the balloon material so that when the balloon is deflated after the stent is expanded, there is an imprint of the stent pattern on the balloon. Pressurization and heating provide additional stent retention. Cross-section 214 represents the main body of the stent that expands and is implanted in the main branch vessel.

After the stent and balloons are advanced through finish section 203, the catheter assembly can be pulled back through the mold assembly 200 without damaging or dislodging the stent, since its profile is substantially smaller in its crimped state than when it entered the mold assembly prior to crimping. The mold assembly can be made from any type of material that is compatible with the metal alloy of the stent being crimped. For example, the mold assembly can be made from stainless steel, a hardened plastic, or glass that will not scratch or cause any surface irregularities to the stent or damage the balloons or catheter in any way during the crimping process.

Delivering and Implanting the Stent

Referring to FIGS. 35-41, the bifurcated catheter assembly of the present invention provides two separate balloons in parallel which can be advanced into separate passageways of an arterial bifurcation and inflated either simultaneously or independently to expand and implant a stent. As shown in the drawings, bifurcation 300 typically includes a main vessel 301 and a side branch vessel 302 with the junction between the two referred to as the carina 304. Typically, plaque 305 will develop in the area around the junction of the main vessel and the side branch vessel in an area proximal to the side branch vessel and, as previously described with the prior art devices, is difficult to stent without causing other problems such as portions of the stent extending into the blood flow path jailing a portion of the side branch vessel, causing plaque to shift at the carina and subsequently occlude the vessel, or unnecessarily stenting the main vessel distal to the bifurcation where there is no plaque.

In keeping with the invention, the catheter assembly 101 or 140 is advanced through a guiding catheter (not shown) in a known manner. Once the distal end 102 of the catheter reaches the ostium to the coronary arteries, the Rx guide wire 310 is advanced distally into the coronary arteries (or any other bifurcated vessel) so that the Rx guide wire distal end 311 extends past the opening to the side branch vessel 303. (In most cases, the main vessel will have been predilated in a known manner prior to delivery of the trap door stent. In these cases, the Rx guide wire will have been left in place across and distal to the target site prior to loading the catheter assembly onto the Rx guide wire for advancement to the target site.) After the distal end of the Rx guide wire is advanced into the main vessel past the opening to the side branch vessel, the catheter is advanced over the Rx guide wire so that the catheter distal end 102 is just proximal to the opening to the side branch vessel. Up to this point in time, the OTW guide wire 312 (or mandrel) remains within the catheter and within coupler 119 keeping the tips and balloons joined. More specifically, the OTW guide wire remains within the OTW guide wire lumens 105,108, and 130 as previously described. The distal end of the OTW guide wire 313 is positioned within coupler blind lumen 121 during delivery and up to this point in time. As the catheter is advanced through tortuous coronary arteries, the OTW guide wire distal end 313 should be able to slide axially a slight amount relative the coupler blind lumen to compensate for the bending of the distal end of the catheter. As the catheter distal end moves through tight twists and turns, the coupler moves axially relative to the balloon shaft that it is not attached to thereby creating relative axial movement with the OTW guide wire. Stated differently, the coupler moves axially a slight amount while the OTW guide wire remains axially fixed (until uncoupled) relative to the catheter shaft. If the OTW guide wire were fixed with respect to the coupler at the distal end, it would make the distal end of the catheter stiffer and more difficult to advance through the coronary arteries, and may cause the distal end of the catheter to kink or to be difficult to push through tight turns. Thus, the coupler moves axially relative to the distal end of the OTW guide wire in a range of approximately 0.5 mm up to about 5.0 mm. Preferably, the coupler moves axially relative to the OTW guide wire distal end 313 about 0.5 mm to about 2.0 mm. The amount of axial movement will vary depending on a particular application and the severity of the tortuosity. The proximal end of the OTW guide wire (or joining wire or mandrel) should be removably fixed relative to the catheter shaft during delivery so that the distal end of the OTW guide wire does not prematurely pull out of the coupler. The distal end of the OTW guide wire still moves axially a small amount within the coupler as the distal end of the catheter bends and twists in negotiating tortuous anatomy.

As previously disclosed and as shown in FIG. 28A, radiopaque markers 140 are positioned on the inner shaft and coincide or align with the long balloon 117 and the short balloon 129. The radiopaque markers will assist in positioning the catheter assembly 101, and more specifically the long balloon and short balloon with respect to the opening to the side branch vessel 303. Typically, it is desirable to have one radiopaque marker centered with respect to the length of the long balloon, and perhaps several other radiopaque markers defining the overall length of the long balloon, or defining the length of the unexpanded or expanded stent 20. Similarly, a radiopaque marker associated with the short balloon is preferably aligned with the center radiopaque marker of the long balloon.

Figure 36:
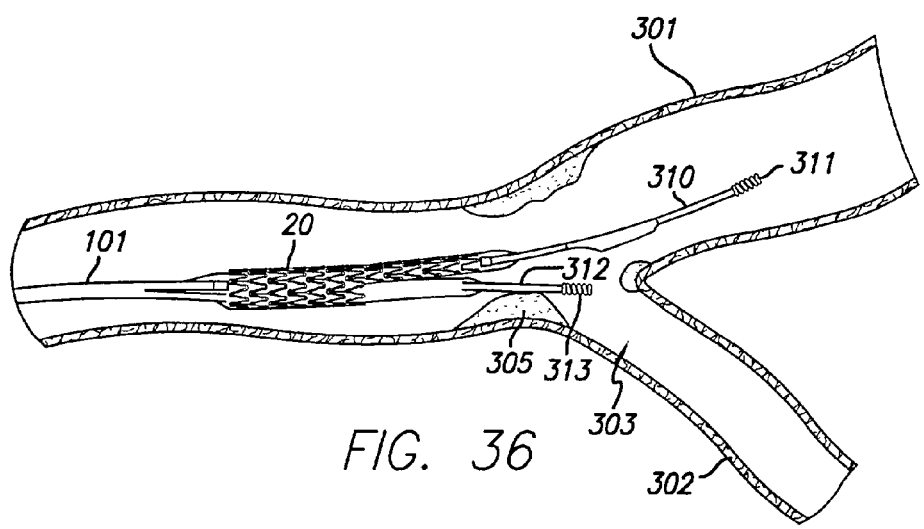
FIG. 36 is an elevational view of the catheter assembly in the main vessel prior to advancement into the side branch vessel.
Figure 37:
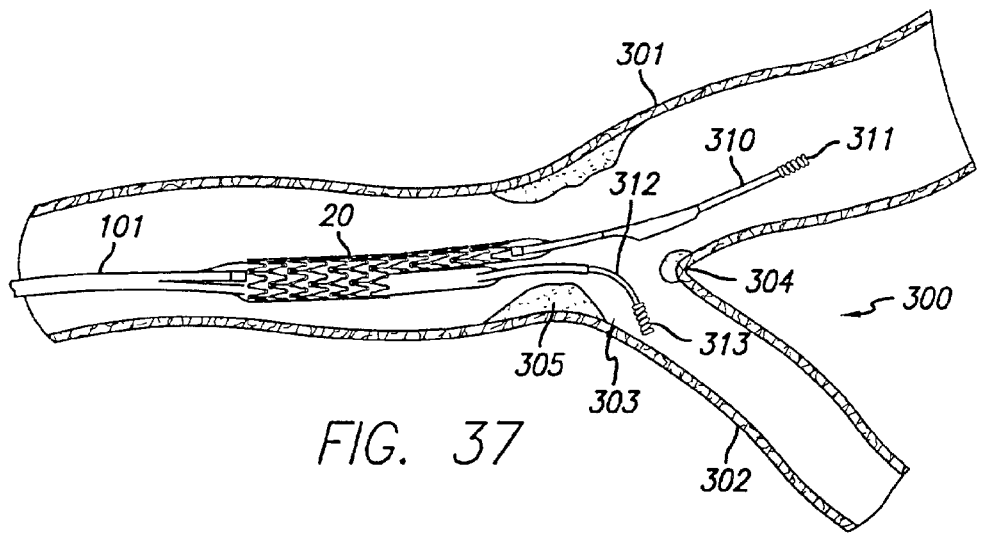
FIG. 37 is an elevational view of the catheter assembly as the over-the-wire guide wire is being advanced into the side branch vessel.
Figure 38:
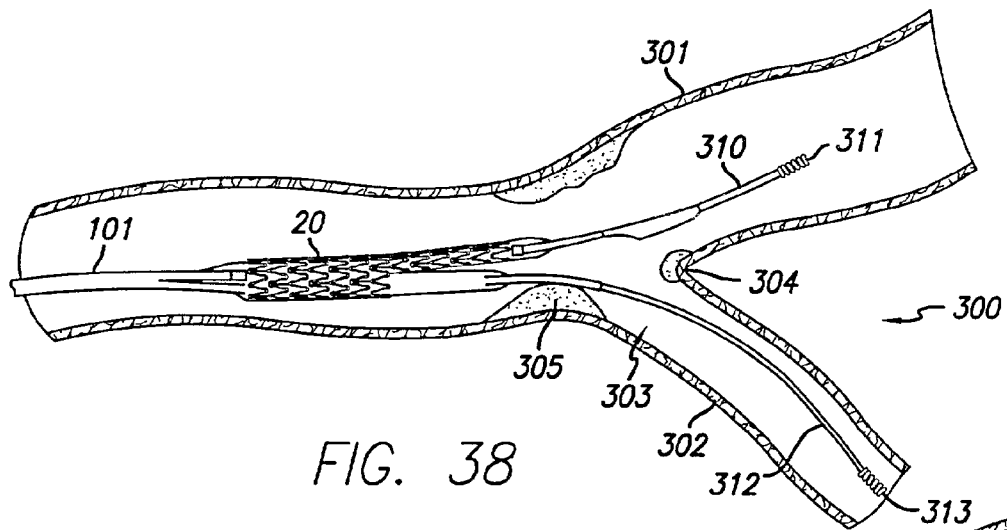
FIG. 38 is an elevational view of the catheter assembly positioned in the main vessel and the over-the-wire guide wire advanced and positioned in the side branch vessel.
Figure 39:
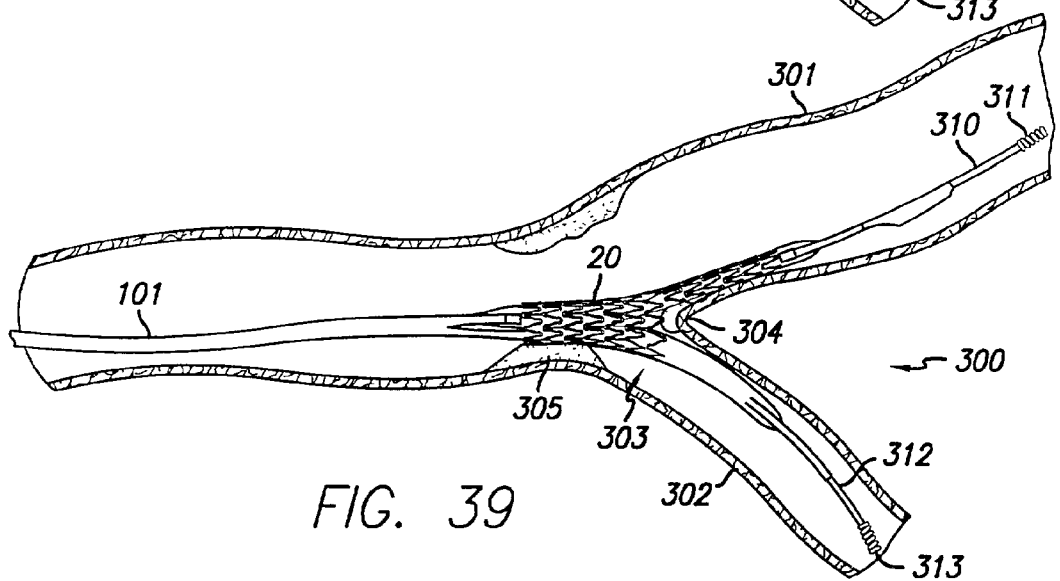
FIG. 39 is an elevational view of the catheter assembly advanced so that the long balloon is in the main vessel and a portion of the short balloon is positioned in the side branch vessel.
Figures 40, 41:
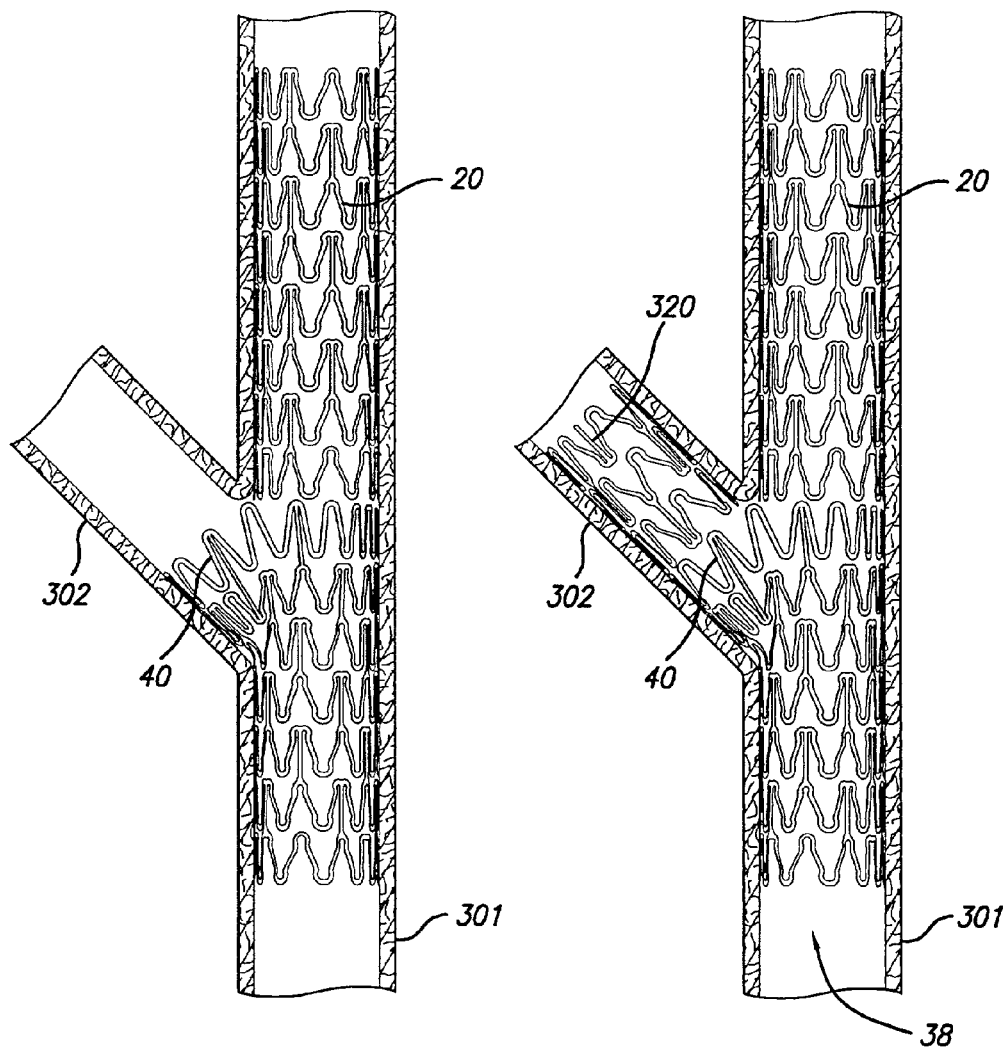
FIG. 40 is an elevational view of a bifurcation depicting the stent of the invention implanted in the main vessel and the opening to the side branch vessel.
FIG. 41 is an elevational view of a bifurcation in which the stent of the present invention is implanted in the main vessel, and a second stent is implanted in the side branch vessel.
Figure 42:
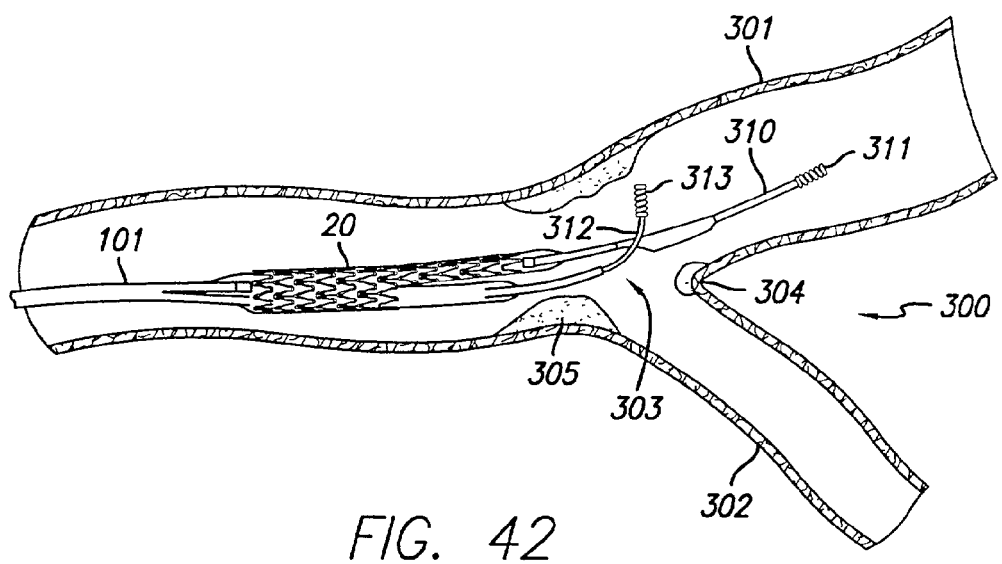
FIG. 42 is an elevational view depicting the catheter assembly positioned in the main vessel and the over-the-wire guide wire advancing out of the catheter.
Figure 43:
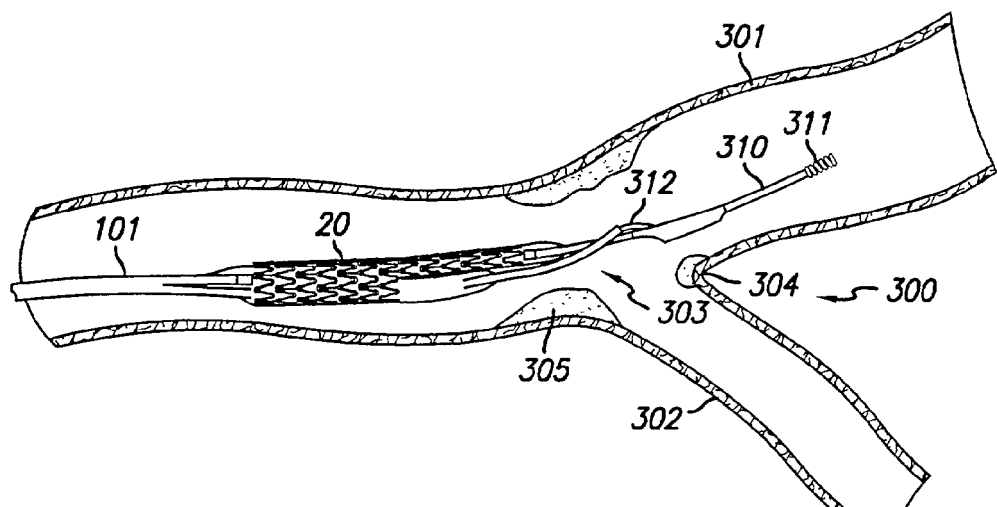
FIG. 43 is an elevational view of the catheter assembly positioned in the main vessel and the over-the-wire guide wire wrapping around the coupler.
Figure 44:
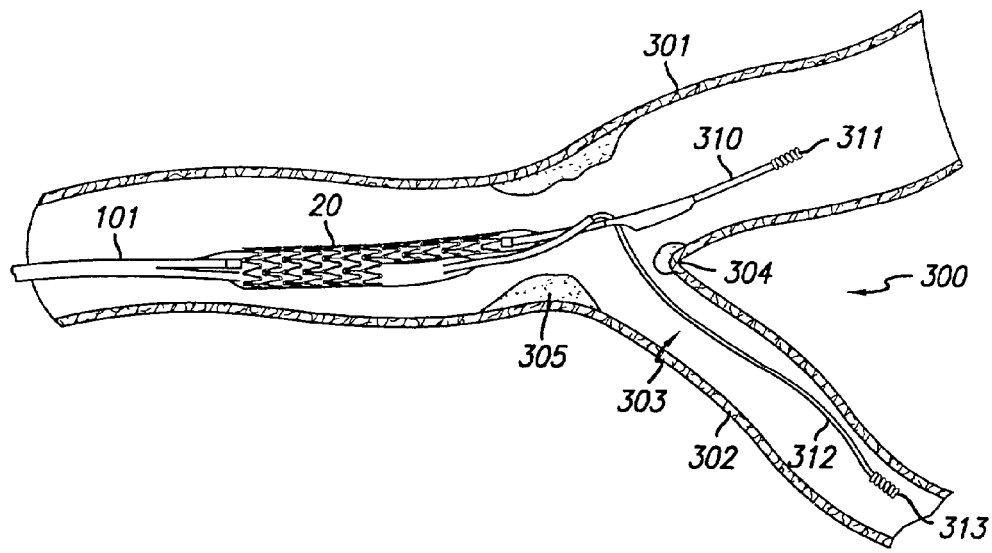
FIG. 44 is an elevational view showing the catheter assembly positioned in the main vessel and the over-the-wire guide wire wrapped over the coupler and positioned in the side branch vessel.

As shown for example in FIG. 36, the OTW guide wire 312 next is withdrawn proximally so that the OTW guide wire distal end 313 is removed from the coupler blind lumen 121. As shown in FIG. 37, the OTW guide wire next is advanced distally into the side branch vessel 302, extending past the opening to the side branch vessel 303 and advancing distally into the vessel for a distance as shown in FIG. 38. Once the Rx guide wire 310 is in position in the main vessel, and the OTW guide wire 312 is in position in the side branch vessel, this will have a tendency to impart a slight separation between the long balloon 117 and the short balloon 129. As shown in FIG. 39, the catheter assembly 101 is advanced distally over the Rx guide wire and the OTW guide wire and, as the assembly is further advanced, the long balloon 117 continues to separate from the short balloon 129 as each advances into the main vessel 301 and the side branch vessel 302 respectively. As the assembly continues to advance distally, it will reach the point where on the stent 20 is adjacent the opening to the side branch vessel 303. At this point, the catheter assembly can no longer be advanced distally since the stent is now pushing up against the opening to the side branch vessel. The long balloon 117 and the short balloon 129 are next inflated simultaneously to expand the stent 20 into the main vessel and into the opening to the side branch vessel. As shown in FIG. 40, a portion of the central opening of the stent will expand into contact with the opening to the side branch vessel and the central opening the stent should coincide with the opening to the side branch vessel providing a clear blood flow path through the proximal opening of the stent 38 and through the central opening into the side branch vessel. The expanded stent 20 is shown in FIG. 40 covering both the portion of the main vessel that is proximal to the side branch vessel and the opening to the side branch vessel.

In keeping with the invention, as the catheter assembly is advanced through tortuous coronary arteries, the central opening 40 of the stent 20 may or may not always be perfectly aligned with the opening to the side branch vessel 303. If the central opening of the stent is in rotational alignment with the opening to the side branch vessel the stent is said to be "in phase" and represents the ideal position for stenting the main branch vessel and the opening to the side branch vessel. When the opening and the opening to the side branch vessel are not rotationally aligned it is said to be "out of phase" and depending upon how may degrees out of phase, may require repositioning or reorienting the central opening with respect to the opening to the side branch vessel. More specifically, the misalignment can range anywhere from a few degrees to 360°. If the central opening is in excess of 90° out of phase with respect to the opening to the side branch vessel, it may be difficult to position the stent with respect to the longitudinal axis. When the out of phase position is approximately 270° or less, the stent 20 still can be implanted and the central opening will expand into the opening to the side branch vessel and provide adequate coverage provided that the stent and radiopaque markers can be positioned longitudinally. Due to the unique and novel design of the catheter assembly and the stent of the present invention, this misalignment is minimized so that the central opening 40 generally aligns with the opening to the side branch vessel, even if the central opening is out of phase approximately 90° from the opening of the side branch vessel 303. Typically, the alignment between the central opening and the opening to the side branch vessel will be less than perfect, however, once the OTW guide wire 312 is advanced into the side branch vessel 302, as previously described, the assembly will slightly rotate the central opening 40 into better alignment with the opening to the side branch vessel. As can be seen in FIGS. 35-39, after the stent has been properly oriented, it is expanded into contact with the main branch vessel and the central opening expanded to contact with the opening to the side branch vessel.

As shown in FIG. 41, a second stent 320 can be implanted in the side branch vessel 302 such that it abuts central opening 40 of stent 20. The second stent can be delivered and implanted in the following manner. After implanting stent 20, the long balloon 117 and the short balloon 119 are deflated and catheter assembly 101 (or 140) are removed from the patient by first withdrawing the Rx guide wire 310 and then withdrawing the catheter assembly over the in-place OTW guide wire 312 (an extension guide wire which is known in the art may be required), which remains in the side branch vessel 302. Alternatively, the catheter assembly can be withdrawn from the patient while leaving both the Rx and OTW guide wires in place in their respective vessels. Next, a second catheter assembly (not shown) on which second stent 320 is mounted, is backloaded onto the proximal end of the OTW guide wire 312. The catheter assembly is next advanced through the guiding catheter and into the coronary arteries over the OTW guide wire, and advanced such that it extends into proximal opening 38 of the expanded and implanted stent 20. The second catheter assembly is advanced so that it extends through the opening to the side branch vessel and advances over the OTW guide wire 312 and into the side branch vessel where second stent 320 can be expanded and implanted in the side branch vessel to abut the trap door portion of stent 20. Alternatively, the catheter assembly 101 can be withdrawn to just proximal of the bifurcation, the Rx guide wire 310 withdrawn proximally into the catheter, and then the catheter assembly advanced into the side branch vessel over the in-place OTW guide wire 312. The Rx guide wire can then be advanced into the side branch vessel, the OTW guide wire safely withdrawn into the catheter assembly, and the catheter assembly then safely removed in an Rx exchange over the Rx guide wire which remains in place in the side branch vessel. Thereafter the second catheter assembly can be advanced over the in-place Rx guide wire 310 and into the side branch vessel where the second stent is implanted as previously described. Care must be taken in this approach to avoid wire wrapping, that is avoiding wrapping the Rx and OTW guide wires in the side branch vessel.

In another alternative embodiment for implanting second stent 320, the long balloon 117 and the short balloon 119 are deflated and catheter assembly 101 is removed from the patient by first withdrawing OTW guide wire 312 so that it resides within the catheter assembly, and then withdrawing the catheter assembly over the in-place Rx guide wire 310, which remains in the main vessel 301. Next, a second catheter assembly (not shown) on which second stent 320 is mounted, is back loaded onto the proximal end of Rx guide wire 310, advanced through the guiding catheter into the coronary arteries, and advanced such that it extends into the proximal opening 38 of the expanded and implanted stent 20. The Rx guide wire is then withdrawn proximally a short distance so that the Rx guide wire distal end 311 can be torqued and rotated so that it can be advanced into the side branch vessel 302. Once the Rx guide wire is advanced into the side branch vessel, the second catheter is advanced and the second stent 320 is positioned in the side branch vessel where it is expanded and implanted in a conventional manner as shown in FIG. 41. The second catheter assembly is then withdrawn from the patient over the Rx guide wire.

Figure 35:
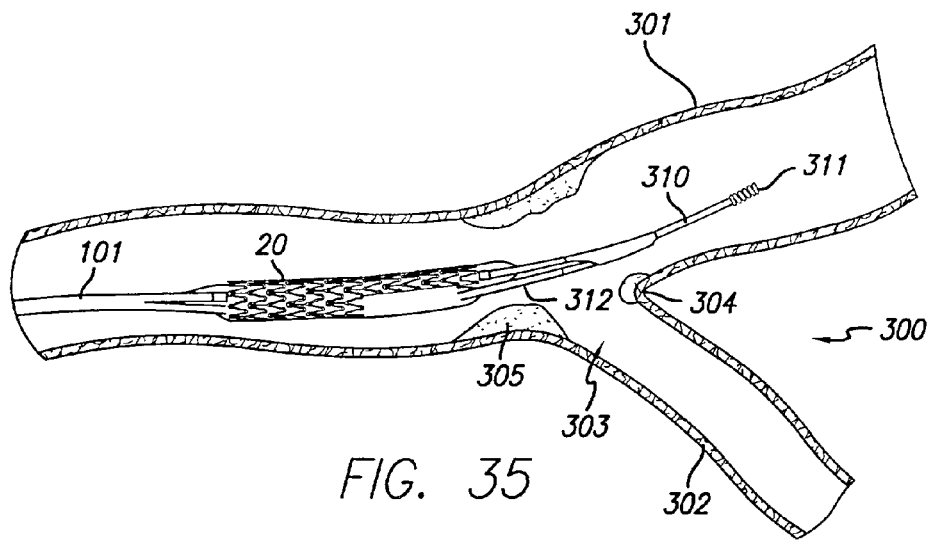
FIG. 35 is an elevational view of the catheter assembly being advanced into the main vessel.

In an alternative method of deploying and implanting stent 20, the catheter assembly 101 as shown in FIGS. 35-41 can be adapted to carry a mandrel (not shown) instead of the OTW guide wire. For example, during delivery and positioning of the stent in the main branch vessel 301, a mandrel resides in the OTW guide wire lumens 105,108, and 130, and the distal end of the mandrel extends into and resides in coupler blind lumen 121. As the catheter assembly is positioned just proximal to the bifurcation, such as shown in FIGS. 35 and 36, the mandrel is withdrawn proximally from the catheter assembly allowing the long balloon 117 and the short balloon 129 to slightly separate. Thereafter, an OTW guide wire 312 is front-loaded into the proximal end of the catheter assembly and advanced through the OTW guide wire lumens and into the side branch vessel 302 as shown in FIGS. 37 and 38. After this point, the delivery and implanting of the stent is the same as previously described.

In an alternative method of delivering and implanting the stent of the invention, the catheter assembly 101 or 140 is advanced through a guiding catheter (not shown) in a known manner. Once the distal end 102 of the catheter reaches the ostium to the coronary arteries, the Rx guide wire 310 is advanced out of the Rx shaft 111 and advanced distally into the coronary arteries (or any other bifurcated vessels) so that the Rx guide wire distal end 311 extends through the opening to the side branch vessel 303. (As noted above, the Rx guide wire may already be positioned in the main vessel or side branch vessel as a result of a pre-dilatation procedure). After the distal end of the Rx guide wire is advanced into the side branch vessel, the catheter is advanced over the Rx guide wire so that the catheter distal end 102 is positioned distal to the opening to the side branch vessel and partially within the side branch vessel. More specifically, the short tip of the short balloon 129 should be distal to the carina 304. Up to this point in time, the OTW guide wire 312 remains within the catheter and within coupler 119. More specifically, the OTW guide wire remains within the OTW guide wire lumens 105,108, 130 as previously described. The distal end of the OTW guide wire 313 is positioned within coupler blind lumen 121 during delivery and up to this point in time. As the catheter is advanced through tortuous coronary arteries, for example, the OTW guide wire distal end 313 should be able to move axially a slight amount within the coupler blind lumen to compensate for the bending of the distal end of the catheter. If the OTW guide wire were fixed with respect to the catheter shaft and the coupler at the distal end, it would make the distal end of the catheter stiffer and more difficult to advance through the coronary arteries, and may cause the distal end of the catheter to kink or be more difficult to push through tight turns. Thus, the distal end of the OTW guide wire will move axially in a range of approximately 0.5 mm up to about 5.0 mm. Preferably, the OTW guide wire distal end 313 will move back and forth axially about 0.5 mm to about 2.0 mm. The amount of axial movement depends on a particular application or vessel tortuousity. The proximal end of the OTW guide wire should be removably fixed relative to the catheter shaft during delivery so that the distal end of the OTW guide wire does not prematurely pull out of the coupler. The distal end of the OTW guide wire still moves axially a small amount within the coupler as the distal end of the catheter bends and twists in negotiating tortuous anatomy.

The OTW guide wire 312 next is withdrawn proximally so that the OTW guide wire distal end 313 is removed from the coupler blind lumen 121. The OTW guide wire next is advanced distally into the side branch vessel 302 a short distance. The catheter assembly is next withdrawn proximally so the long balloon 117 and the short balloon 129 are in the main vessel just proximal of the opening of the side branch vessel. More specifically, the coupler distal tip is proximal to vessel carina 304. As the catheter assembly is withdrawn from the side branch vessel, the long balloon and short balloon will begin to separate slightly. Thereafter, the Rx guide wire 310 is withdrawn proximally until it is clear of the opening to the side branch vessel, whereupon it is advanced distally into the main branch vessel for a distance. The catheter assembly next is advanced distally over the Rx guide wire in the main branch vessel and the OTW guide wire in the side branch vessel. As the catheter advances distally, the long balloon and short balloon will separate at least partially until the short balloon enters the side branch vessel and the long balloon continues in the main branch vessel. As the balloons and stent push up against the ostium of the bifurcation, the catheter assembly cannot be advanced further and the stent is now in position to be expanded and implanted. At this point the radiopaque markers should be appropriately positioned. The central opening 40 on the stent 20 should be approximately adjacent the opening to the side branch vessel 303. The long balloon 117 and the short balloon 129 are next inflated simultaneously to expand the stent 20 into the main vessel and into the opening into the side branch vessel respectively. A portion of the central section 28 of the stent will expand into contact with the opening to the side branch vessel and the central opening 40 of the stent should coincide to the opening of the side branch vessel providing a clear blood flow path through the proximal opening of the stent 38 and through the central opening 40 into the side branch vessel. When fully expanded, stent 20 should cover at least a portion of the main vessel and the opening to the side branch vessel. After the stent has been expanded and implanted, the balloons are deflated and the assembly is withdrawn from the vascular system over the Rx and OTW guide wires. The Rx and OTW guide wires remain in place in the main and side branch vessels for further procedures.

The above procedures can also be performed with a spare safety wire placed in the alternate vessel. The safety wire is removed from the patient after the OTW guide wire has been advanced into the side branch vessel (first case) or the Rx guide wire has been advanced into the distal main vessel (second case). The safety wire allows access to the vessel should closure from a dissection or spasm occur.

Figure 45:
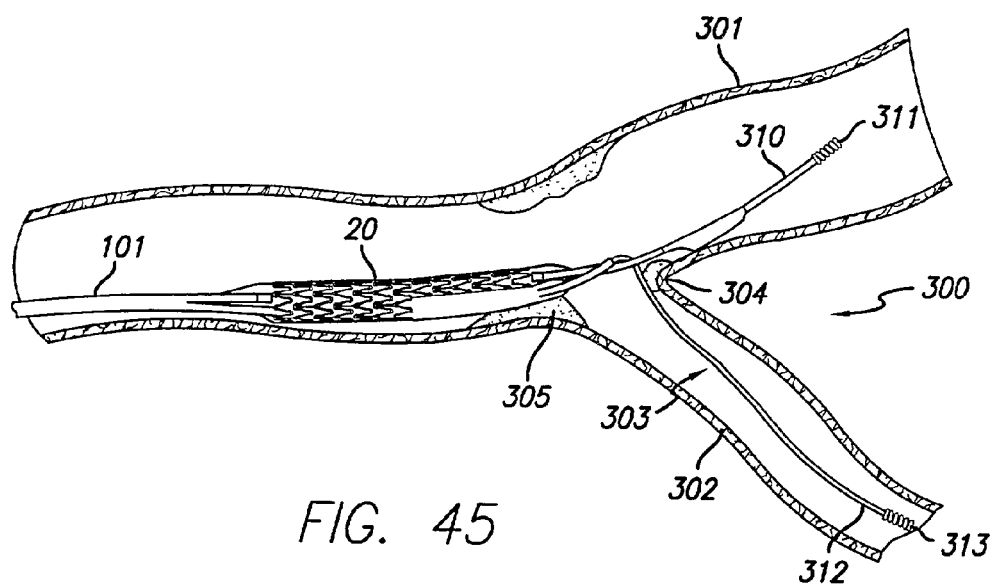
FIG. 45 is an elevational view of the catheter assembly advanced toward the carina or bifurcation junction but unable to advance further due to the over-the-wire guide wire wrapped over the coupler and/or the long tip.

As can be seen in FIGS. 42-45, the OTW guide wire 312 on occasion can be inadvertently torqued in the wrong direction and wrap around the distal end 102 of the catheter or around the coupler 119 prior to advancing into the side branch vessel 302. If this occurs, and the OTW guide wire is advanced into the side branch vessel, the catheter assembly can be advanced distally only a certain distance before the crossed wires reach the junction or carina of the main vessel and the side branch vessel and the catheter can no longer be advanced distally. At this point, the physician knows that the wires are wrapped or that the central opening is severely out of alignment with the opening of the side branch vessel, in which cases the OTW guide wire 312 is withdrawn proximally into the catheter and the catheter assembly is reoriented by rotating the assembly to better position the central opening 40 with respect to the opening to the side branch vessel prior to advancing the OTW guide wire 312. Thus, as shown in FIG. 45, once the guide wires are wrapped, the OTW guide wire must be withdrawn proximally, and then readvanced into the side branch vessel taking care to avoid wrapping. The catheter assembly would then be readvanced in an effort to reorient the central opening 40 with the opening to the side branch vessel.

If it becomes impossible to deliver the stent for whatever reason, including that described above with respect to the wrapped guide wires, the catheter assembly 101 can be withdrawn into the guiding catheter and removed from the patient. Typically, the OTW guide wire 312 would be withdrawn proximally into the catheter and the catheter assembly would be withdrawn proximally over the Rx guide wire which remains in place in the main vessel 301. Alternatively, as the catheter assembly is withdrawn, the stent can be safely implanted proximal to the bifurcation. If desired, a second catheter assembly can be backloaded over in-place Rx guide wire 310 and advanced through the guiding catheter and into the coronary arteries as previously described to implant another stent.

Alternative Catheter Assemblies

In keeping with the invention, as shown in FIGS. 46-50, the stent 20 is mounted on alternative catheter assembly 401 which has a distal end 402 and a proximal end 403. The catheter assembly includes a proximal shaft 404 which has a proximal shaft over-the-wire (OTW) guide wire lumen 405 and a proximal shaft inflation lumen 406 which extends therethrough. The proximal shaft OTW guide wire lumen is sized for slidably receiving an OTW guide wire. The inflation lumen extends from the catheter assembly proximal end where an indeflator or similar device is attached in order to inject inflation fluid to expand balloons or expandable members as will be herein described. The catheter assembly also includes a mid-shaft 407 having a mid-shaft OTW guide wire lumen 408 and a mid-shaft rapid-exchange (Rx) guide wire lumen 409. The proximal shaft OTW guide wire lumen 405 is in alignment with and an extension of the mid-shaft OTW guide wire lumen 408 for slidably receiving an OTW guide wire. The mid-shaft also includes a mid-shaft inflation lumen 410 which is in fluid communication with the proximal shaft inflation lumen 406 for the purpose of providing inflation fluid to the expandable balloons. There is an Rx proximal port or exit notch 415 positioned on the mid-shaft such that the Rx proximal port is substantially closer to the distal end 402 of the catheter assembly than to the proximal end 403 of the catheter assembly. While the location of the Rx proximal port may vary for a particular application, typically the port would be between 10 and 50 cm from the catheter assembly distal end 402. The Rx proximal port or exit notch provides an opening through which an Rx guide wire 416 exits the catheter and which provides the rapid exchange feature characteristic of such Rx catheters. The Rx port 415 enters the mid-shaft such that it is in communication with the mid-shaft Rx guide wire lumen 409.

The catheter assembly 401 also includes a distal Rx shaft 411 that extends from the distal end of the mid-shaft and which includes an Rx shaft Rx guide wire lumen 412, to the proximal end of the inner member 411A inside balloon 417. The distal Rx shaft 411 also contains an Rx shaft inflation lumen 414. The Rx shaft Rx guide wire lumen 412 is in alignment with the Rx guide wire lumen 409 for the purposes of slidably carrying the Rx guide wire 416. The Rx shaft inflation lumen 414 is in fluid communication with the mid-shaft inflation lumen 410 for the purposes of carrying inflation fluid to the long expandable member or long balloon.

The catheter assembly also contains an Rx inner member 411A that extends from the distal end of the distal Rx shaft 411 to a blind lumen port 422 of coupler 419. The Rx inner member 411A contains an Rx guide wire lumen 411B. The Rx inner member guide wire lumen 411B is in alignment with the Rx shaft Rx guide wire lumen 412 for the purpose of slidably carrying the Rx guide wire 416. The Rx guide wire will extend through the Rx proximal port 415 and be carried through Rx guide wire lumen 409 and Rx shaft Rx guide wire lumen 412, and through Rx guide wire lumen 411B and into coupler 419.

The catheter assembly further includes a long balloon 417 positioned adjacent the distal end of the catheter assembly and a distal tip 418 at the distal end of the Rx shaft. Further, coupler 419 is associated with distal Rx shaft 411 such that the Rx shaft Rx guide wire lumen 412 extends into the coupler. The coupler 419 includes a blind lumen 421 for receiving and carrying the Rx guide wire 416. The blind lumen includes a blind lumen port 422 for receiving the distal end of the Rx guide wire 416. The coupler blind lumen 421 will carry the distal end of the Rx guide wire 416 during delivery of the catheter assembly through the vascular system and to the area of a bifurcation. The blind lumen is approximately 3 to 20 mm long, however, the blind lumen can vary in length and diameter to achieve a particular application or to accommodate different sized guide wires having different diameters and length. The guide wire that resides in the blind lumen 421 should be able to slide axially in the coupler as the coupler moves during delivery of the catheter assembly through the vascular system and tortuous anatomy so that the guide wire does not get jammed into the dead end portion of the blind lumen, which may cause the distal end of the catheter assembly to bind or kink as it travels along tight curves. A distance should be maintained between the distal end of the Rx guide wire 416 and the dead end of the blind lumen. The distance can range from approximately 0.5 to 5.0 mm, however, this range may vary to suit a particular application. Preferably, the distance between the Rx guide wire distal end and the dead end of the blind lumen should be about 0.5 mm to about 2.0 mm.

In further keeping with the invention, the catheter assembly 401 also includes an OTW shaft 428 which extends from the distal end of mid-shaft 407. The OTW shaft carries a short balloon 429 that is intended to be shorter than long balloon 417 and positioned substantially adjacent to the long balloon. The OTW shaft 428 also includes an OTW lumen 430 that is in alignment with the mid-shaft OTW guide wire lumen 408 and proximal shaft OTW guide wire lumen 405. Thus, an OTW lumen extends from one end of the catheter assembly to the other and extends through the OTW shaft 428. An OTW shaft distal port 431 is at the distal end of the OTW lumen 430 and the OTW shaft 428 also includes an OTW shaft inflation lumen 432. Inflation lumen 432 is in alignment and fluid communication with inflation lumens 410 and 406 for the purpose of providing inflation fluid to the long balloon 417 and the short balloon 429. In this particular embodiment, an OTW guide wire 425 would extend from the proximal end 403 of the catheter assembly and through proximal shaft OTW guide wire lumen 405, mid-shaft OTW guide wire lumen 408, OTW lumen 430 where it would extend through the coupler 419, and more specifically through the coupler through lumen 426 and out distal port 413.

In order for the catheter assembly 401 to smoothly track and advance through tortuous vessels, it is preferred that the Rx lumen 411B be substantially aligned with the blind lumen 421 of coupler 419. In other words, as the Rx guide wire 416 extends out of the Rx lumen 411B, it should be aligned without bending more than about 10° so that it extends fairly straight into the coupler blind lumen 421. If the Rx lumen 411 and the coupler blind lumen 421 are not substantially aligned, the pushability and the trackability of the distal end of the catheter assembly may be compromised and the physician may feel resistance as the catheter assembly is advanced through tortuous vessels, such as the coronary arteries.

There are numerous alternative embodiments of the catheter assembly 101,140 and 401 which includes different arrangements for coupling the long and short balloons together during delivery over either the Rx guide wire or the OTW guide wire. These embodiments are disclosed in FIGS. 51-58.

Figure 51:
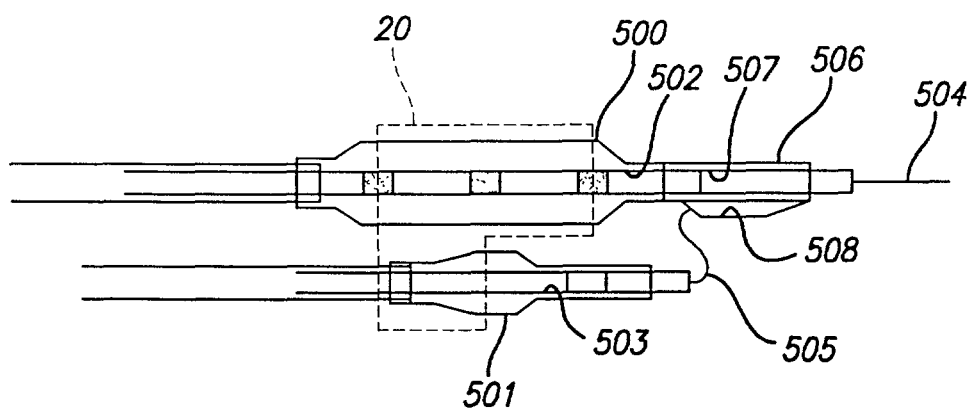
FIG. 51 is a partial schematic view depicting one embodiment of the coupler of the catheter assembly.

In the embodiment disclosed in FIG. 51, the long balloon 500 is adjacent the short balloon 501 with the stent 20 mounted thereon. An Rx guide wire lumen 502 extends through the long balloon and through coupler 506 which has a through lumen 507. An OTW guide wire lumen 503 extends through the short balloon and carries the OTW guide wire 505. The Rx guide wire 504 extends through the Rx guide wire lumen 502 in the long balloon and exits the coupler through lumen 507. A distal end of the OTW guide wire 505 extends into a blind or dead end lumen 508 in the coupler 506 and is adjacent to through lumen 507. Thus, the coupler 506 has dual lumens that are side by side, one of which is a through lumen 507 and the other is a blind lumen 508. In this embodiment, the catheter assembly tracks over the Rx guide wire to the target site or the bifurcation area while the OTW guide wire remains in blind lumen 508, thereby coupling the long balloon and the short balloon during delivery. Once positioned at the bifurcation area, the OTW guide wire is withdrawn proximally to uncouple the short balloon from the long balloon so that the stent can be deployed and implanted.

Figure 52:
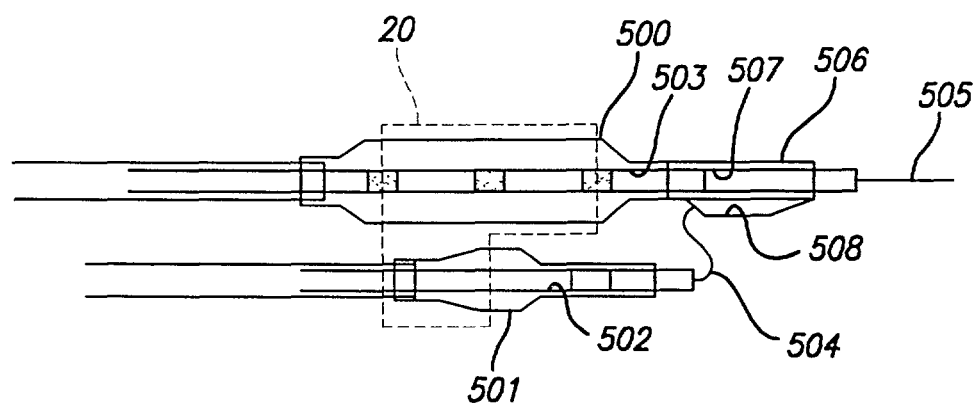
FIG. 52 is a partial schematic view depicting another embodiment of the coupler of the catheter assembly.

In an alternative embodiment, the OTW guide wire lumen extends through the long balloon and the Rx guide wire lumen extends through the short balloon, as shown in FIG. 52. Thus, long balloon 500 is mounted adjacent short balloon 501 and the long balloon carries the OTW guide wire lumen 503, while the short balloon carries the Rx guide wire lumen 502. A coupler 506 has a through lumen 507 which carries the OTW guide wire 505 and a blind lumen 508 which contains the distal end of Rx guide wire 504. During delivery, the catheter assembly tracks over the OTW guide wire 505 until the catheter assembly reaches the target site or bifurcation. Thereafter, the Rx guide wire 504 is withdrawn proximally to uncouple the short balloon from the long balloon so that the catheter assembly can be advanced over the Rx guide wire and the OTW guide wire to further position and implant the stent as previously described. In this embodiment, a locking mechanism to releasably lock the proximal portion of the Rx guide wire will be located on the proximal catheter shaft as previously described.

Figure 53:
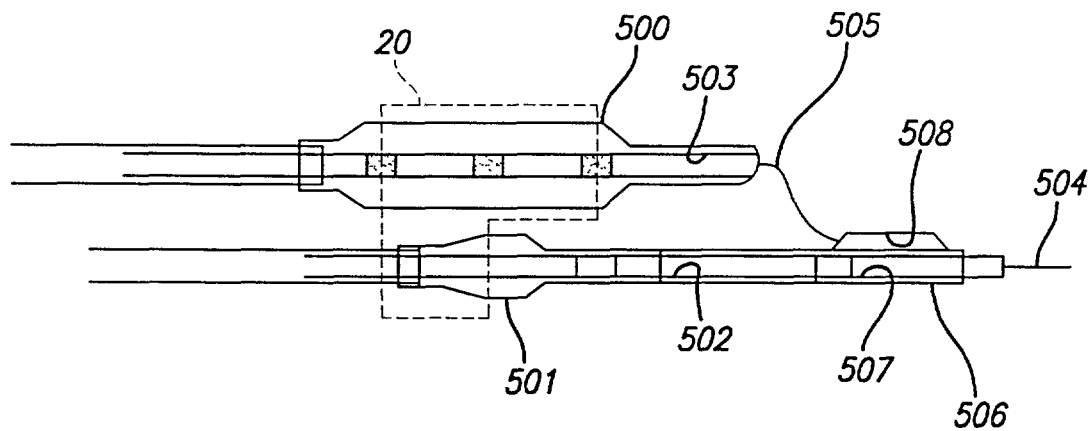
FIG. 53 is a partial schematic view depicting another embodiment of the coupler of the catheter assembly.

In another embodiment, the catheter assembly is delivered over the Rx guide wire which extends through the short balloon and the coupler through lumen. As shown in FIG. 53, the long balloon 500 and the short balloon 501 are adjacent to each other with the stent 20 mounted thereon. Rx guide wire lumen 502 extends through the short balloon and OTW guide wire lumen 503 extends through the long balloon. The Rx guide wire 504 extends through the Rx guide wire lumen and through coupler 506 and through coupler through lumen 507 to extend out of the catheter assembly. The OTW guide wire 504 extends through the OTW guide wire lumen and into blind lumen 508 in coupler 506. During delivery, the catheter is advanced over the Rx guide wire 504 until the target site or bifurcation is reached, whereupon the OTW guide wire is withdrawn proximally from the blind lumen 508 of the coupler 506 so that the short balloon 501 is uncoupled from the long balloon 500. Thereafter, the catheter assembly can be advanced over the guide wire as previously discussed so that the stent can be further delivered and implanted at the bifurcation.

Figure 54:
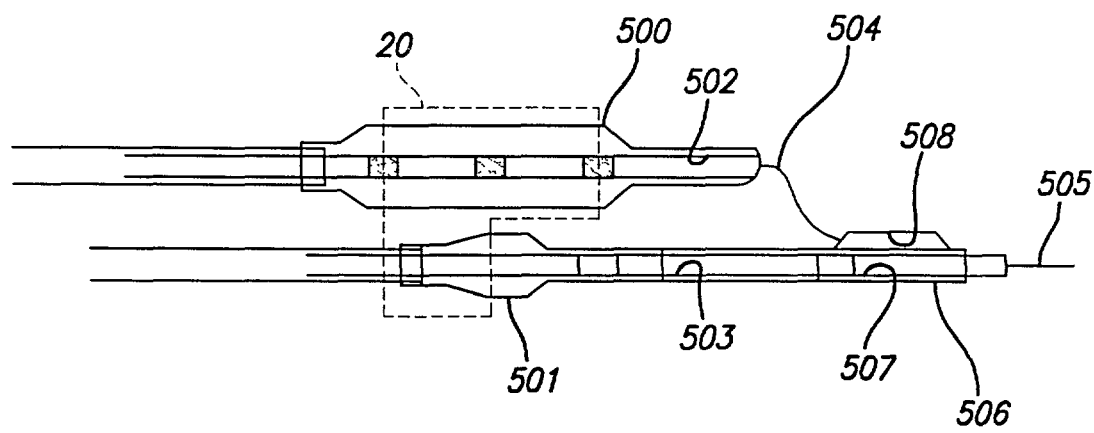
FIG. 54 is a partial schematic view depicting another embodiment of the coupler of the catheter assembly.

In FIG. 54, an alternative embodiment is shown in which the long balloon 500 is adjacent the short balloon 501 with a stent 20 mounted thereon. In this embodiment, the Rx guide wire lumen 502 extends through the long balloon while the OTW guide wire lumen 503 extends through the short balloon. The Rx guide wire 504 extends through the Rx guide wire lumen in the long balloon and extends into coupler 506 so that the distal end of the Rx guide wire is positioned in blind lumen 508. The OTW guide wire extends through the short balloon and through coupler through lumen 507 to extend into the vascular system. The catheter assembly is delivered over the OTW guide wire 505 until the assembly reaches the target site or bifurcation, whereupon the Rx guide wire is withdrawn proximally to uncouple the short balloon from the long balloon. Thereafter, the catheter is further advanced over the guide wires to further position the stent so that the stent can be implanted at the bifurcation. In the embodiments disclosed in FIGS. 51 and 53, the OTW guide wire can be substituted with a joining wire or mandrel for the purpose of coupling the short balloon to the long balloon. Once the catheter assembly has been positioned at the bifurcation by advancing the catheter over the Rx guide wire, the mandrel or joining wire can be removed from the catheter assembly, and the OTW guide wire 505 can be backloaded into the catheter and advanced through the catheter assembly and into the side branch vessel so that the catheter assembly can be further advanced and the stent implanted.

In another embodiment, as shown in FIGS. 55-58, the coupler has side-by-side dual lumens, both of which are through lumens.

Figure 55:
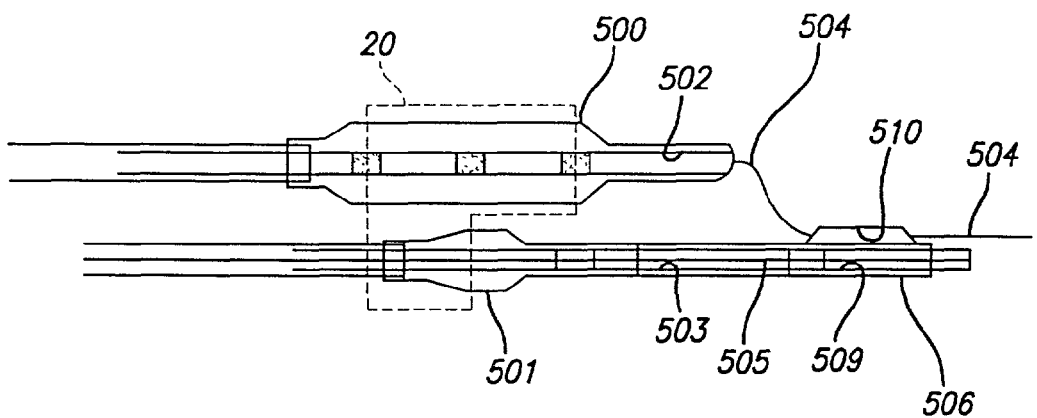
FIG. 55 is a partial schematic view depicting another embodiment of the coupler of the catheter assembly.

In the embodiment disclosed in FIG. 55, the long balloon 500 is positioned adjacent the short balloon 501 with a stent 20 mounted thereon. An Rx guide wire lumen 502 extends through the long balloon and an OTW guide wire lumen 503 extends through the short balloon. The coupler 506 is mounted on the distal tip of the short balloon and has side-by-side dual lumens, including a first through lumen 509 and a second through lumen 510 adjacent thereto. The first through lumen 509 is in alignment with the OTW guide wire lumen 503 while the second through lumen 510 is in alignment with the Rx guide wire lumen 502. Rx guide wire 504 extends through the Rx guide wire lumen and the second through lumen, while the OTW guide wire 505 extends through the OTW guide wire lumen 503 and the first through lumen 509. During delivery, the catheter assembly is advanced over the Rx guide wire 504 while the OTW guide wire 505 remains within second through lumen 510. The catheter assembly is advanced over the Rx guide wire 504 until the catheter assembly is positioned at the bifurcation, whereupon the OTW guide wire can be advanced distally out of through lumen 509 and into the side branch vessel, and the Rx guide wire can then be withdrawn proximally to uncouple the short balloon from the long balloon. The Rx guide wire is then advanced into the main vessel and the catheter assembly advanced over the guide wires as previously described to further position and implant the stent.

Figure 56:
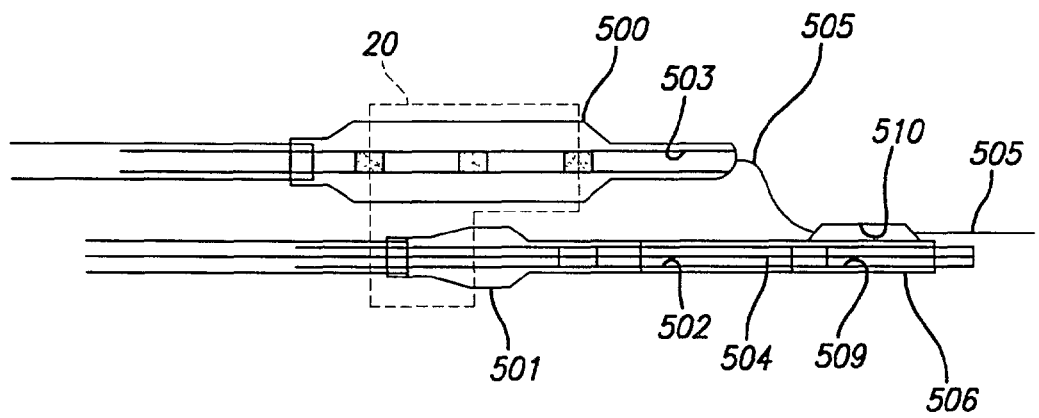
FIG. 56 is a partial schematic view depicting another embodiment of the coupler of the catheter assembly.

In another embodiment, as shown in FIG. 56, the catheter assembly tracks over the OTW guide wire. In this embodiment, the long balloon 500 is adjacent the short balloon 501 with the stent 20 mounted thereon. An Rx guide wire lumen 502 extends through the short balloon while an OTW guide wire lumen 503 extends through the long balloon. An Rx guide wire 504 extends through the Rx guide wire lumen 502 while an OTW guide wire 505 extends through the OTW guide wire lumen 503. The coupler 506 is attached to the distal end of the short balloon and has a first through lumen 509 which aligns with the Rx guide wire lumen 502. The second through lumen 510 extends through the coupler and is substantially in alignment with the OTW guide wire lumen 503. In this embodiment, the OTW guide wire 505 extends through the second through lumen 510 to couple the long balloon to the short balloon. During delivery, the catheter assembly tracks over the OTW guide wire 505 while the Rx guide wire 504 remains in the Rx guide wire lumen and in the first through lumen 509 of the coupler. When the catheter assembly is positioned at the bifurcation, the Rx guide wire 504 is extended distally into the side branch vessel, whereupon the OTW guide wire 505 is withdrawn proximally to uncouple the long balloon and the short balloon. Thereafter, the catheter assembly is advanced over the guide wires so that the stent may be further positioned and implanted as previously described.

Figure 57:
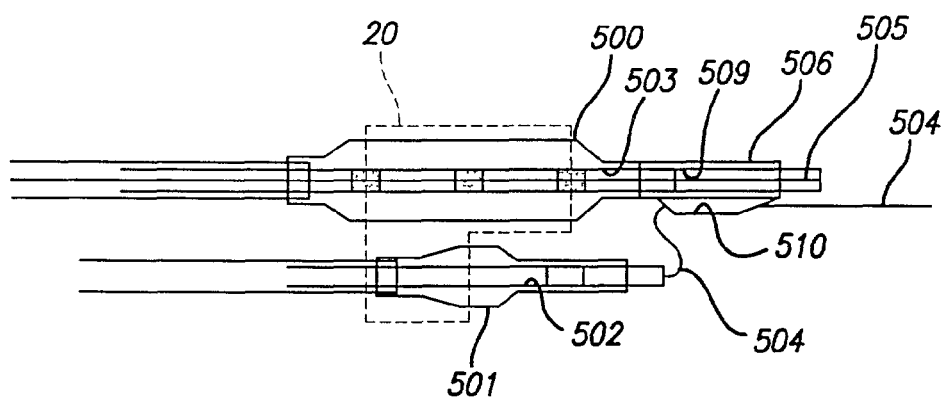
FIG. 57 is a partial schematic view depicting another embodiment of the coupler of the catheter assembly.

In another embodiment, as shown in FIG. 57, the coupler has side-by-side through lumens and the catheter assembly tracks over the Rx guide wire while the OTW guide wire remains in the catheter assembly during delivery. More specifically, as shown in FIG. 57, the long balloon 500 and the short balloon 501 are adjacent to each other with the stent 20 mounted thereon. An Rx guide wire lumen 502 extends through the short balloon while an OTW guide wire lumen 503 extends through the long balloon. An Rx guide wire 504 extends through the Rx guide wire lumen and into and through coupler 506 and through second through lumen 510. The OTW guide wire 505 extends through OTW guide wire lumen 503 and into the coupler where the distal end of the OTW guide wire resides in through lumen 509, but does not extend out of lumen 509 until after the catheter assembly has initially been positioned at the bifurcation. During stent delivery, the catheter assembly is advanced over the Rx guide wire 504 until the distal end of the catheter assembly is positioned at the bifurcation, whereupon the OTW guide wire 505 is advanced distally out of first through lumen 509 and into the main vessel. The Rx catheter 504 is withdrawn proximally from the second through lumen and the coupler 506 to uncouple the long balloon and the short balloon. The Rx guide wire is next advanced into the side branch vessel and the catheter assembly advanced over the guide wires as previously described to further position and implant the stent.

Figure 58:
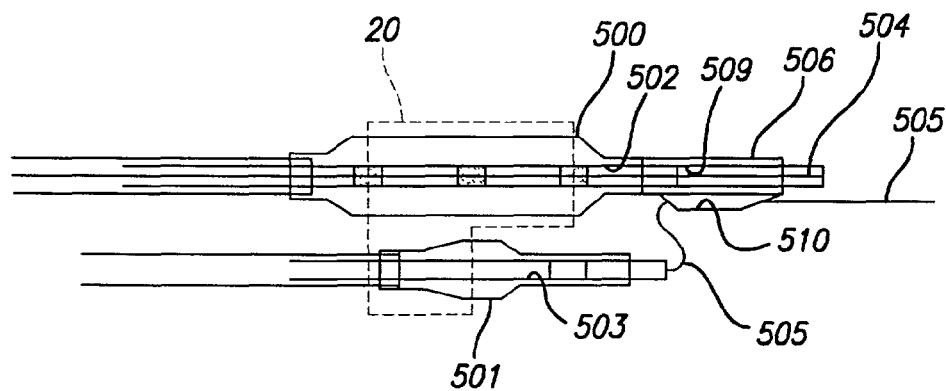
FIG. 58 is a partial schematic view depicting another embodiment of the coupler of the catheter assembly.

In another embodiment, as shown in FIG. 58, a catheter assembly is advanced over the OTW guide wire which is positioned in a coupler having side-by-side through lumens. More specifically, a long balloon 500 is positioned adjacent a short balloon 501 with a stent 20 mounted thereon. An Rx guide wire lumen 502 extends through the long balloon and carries the Rx guide wire 504. An OTW guide wire lumen 503 extends through the short balloon and carries an OTW guide wire 505. The OTW guide wire couples the short balloon to the long balloon by extending through coupler 506 and more specifically through second through lumen 510. The Rx guide wire 504 resides in first through lumen 509 of coupler 506. During delivery of the stent, the catheter assembly is advanced distally over the OTW guide wire 505 until the catheter assembly reaches the target site or bifurcation. Thereafter, the Rx guide wire 504, which has to this point resided in the first through lumen 509 of the coupler is advanced distally out of the first through lumen 509 and into the main vessel. The OTW guide wire 505 is withdrawn proximally from the coupler and the second through lumen 510 to uncouple the short balloon from the long balloon. The OTW guide wire lumen 505 is next advanced into the side branch vessel as previously described, and the catheter assembly is advanced over the guide wires to further position and implant the stent.

A number of alternative embodiments are available for coupling the long balloon to the short balloon as disclosed herein, and particularly as disclosed in embodiments shown in FIGS. 51-58. As described below, alternative coupler embodiments include a sewn tip, a slit tip, a double slit tip, and an expandable slit tip.

Figure 59:
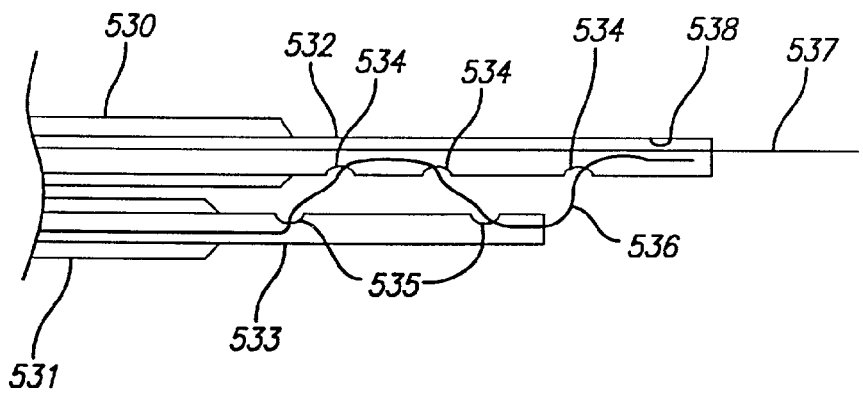
FIG. 59 is a partial schematic view depicting another embodiment for coupling the distal end of the catheter assembly.

As shown in FIG. 59, the so-called sewn tip design is shown in which long balloon 530 is coupled to short balloon 531 with the stent (not shown) mounted thereon. Long tip 532 is adjacent short tip 533 and the long tip has holes 534 and the short tip has holes 535. The holes are aligned and spaced on the long and short tips such that a staggered relationship exists between the hole pairs along the long tip and the short tip. The tips are coupled by a joining wire 536 which is threaded through the staggered holes in the distal section of the long and short tips. The proximal end of the joining wire (not shown) extends proximally through the guide wire lumen to the proximal hub where it is locked into place as previously described by a suitable locking mechanism. A guide wire 537 (either an OTW or Rx guide wire) extends through a guide wire lumen 538. The diameter of the joining wire 536 is such that it occupies minimal space in the guide wire lumen 538 and does not create frictional interference with the guide wire 537. For example, the joining wire can be a nitinol wire having a diameter of approximately 0.006 inch and is flexible enough to extend through the holes 534,535, yet remain rigid enough to couple the long tip 532 to the short tip 533. As previously described, the catheter assembly is advanced over the guide wire 537 until it reaches the target site or bifurcation, whereupon the joining wire 536 is withdrawn from the catheter assembly thereby uncoupling the tips and uncoupling the short balloon from the long balloon.

Figure 60:
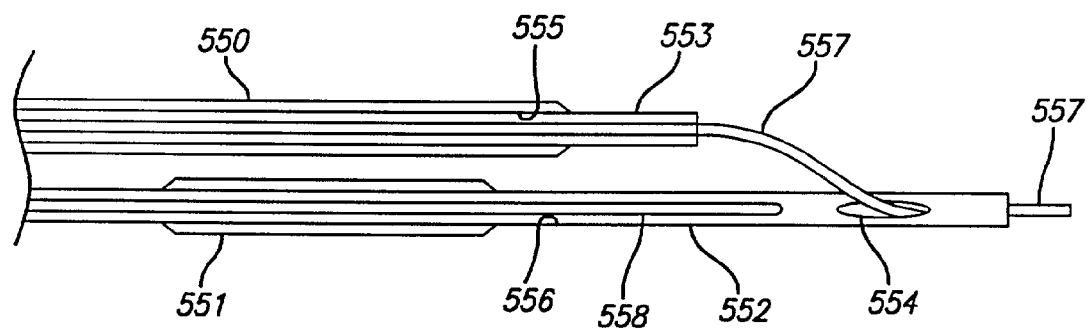
FIG. 60 is a partial schematic view depicting another embodiment for coupling the distal end of the catheter assembly.

In an alternative embodiment for coupling the balloons, as shown in FIG. 60, a long balloon 550 is coupled to short balloon 551. A long tip 552 is attached to the short balloon while a short tip 553 is attached to the long balloon. A slit 554 is formed in a distal section of the long tip 552. An Rx guide wire lumen 555 extends through the long balloon and through the section of the long tip 552 that is distal to the slit 554. An OTW guide wire lumen 556 extends through the catheter assembly and through the short balloon and extends into the long tip 552. An Rx guide wire 557 extends through the Rx guide wire lumen and through slit 554 to couple the two balloons together. An OTW guide wire 558 resides in the OTW guide wire lumen and extends into the long tip 552 to a point just proximal of slit 554. During delivery, the catheter assembly is advanced over the Rx guide wire 557 until the assembly reaches the bifurcation, whereupon the tips are uncoupled by withdrawing the Rx guide wire proximally through the slit. The Rx guide wire is next advanced into the main vessel and the OTW guide wire is advanced through the long tip 552 and into the side branch vessel where the catheter assembly is advanced over the guide wires to further position the stent and implant it at the bifurcation.

Figure 61:
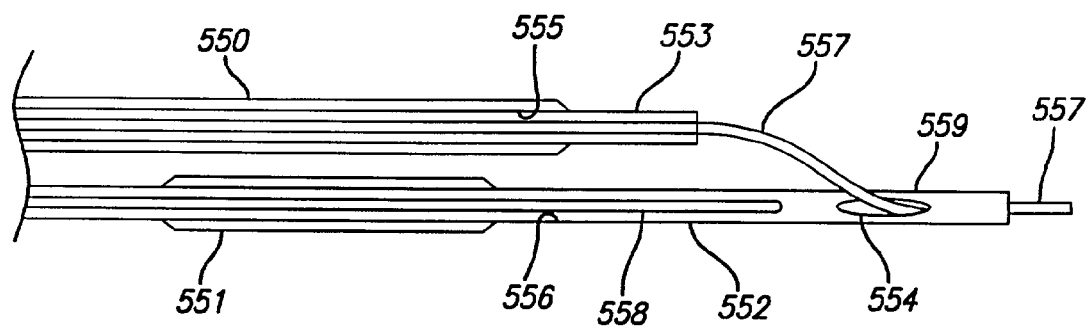
FIG. 61 is a partial schematic view depicting another embodiment for coupling the distal end of the catheter assembly.

In an alternative embodiment that is similar to that shown in FIG. 60 and referring to FIG. 61, a first slit 554 is formed in the long tip 552 and has a second slit 559 that is positioned 1800 opposite the first slit 554 on the distal end of the long tip 552. In this embodiment, the Rx guide wire 557 extends through the Rx guide wire lumen 555 contained in the short tip 553 and extends proximally through the center of the long balloon 550. The Rx guide wire extends distally through the Rx guide wire lumen and exits the short tip then enters the distal section of the long tip through first slit 554. The Rx guide wire exits the long tip and continues distally through the anatomy. The OTW guide wire 558 extends from the distal end of the long tip just proximal of the first slit 554 and extends through the short balloon 551. During the delivery of the stent in this embodiment, the catheter assembly is advanced over the Rx guide wire 557 until the distal end of the catheter assembly reaches the bifurcation. Before the tips are uncoupled, the OTW guide wire is advanced distally through the long tip and exits second slit 559 and continues into the distal anatomy. Advancing the OTW guide wire before retracting the Rx guide wire for uncoupling will ensure wire placement in the distal and diseased anatomy. Maintaining a wire in the distal and diseased anatomy insures access to the vessel in the event of vessel closure due to dissection or spasm. In order to uncouple the balloons, the Rx guide wire 557 is withdrawn proximally through first slit 554 only after the OTW guide wire 558 has been advanced through second slit 559. After the Rx guide wire is retracted out of first slit 554, the long balloon separates from the short balloon and the catheter assembly can be further advanced over the guide wires for further positioning and implanting the stent.

Figure 62:
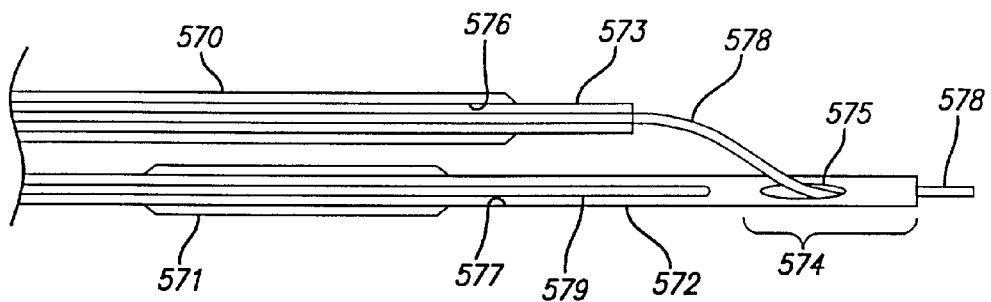
FIG. 62 is a partial schematic view depicting another embodiment for coupling the distal end of the catheter assembly.
Figure 63:
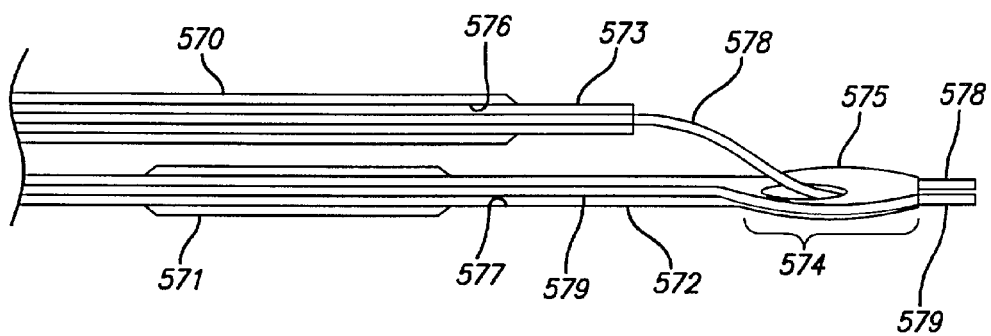
FIG. 63 is a partial schematic view depicting another embodiment for coupling the distal end of the catheter assembly.
Figure 70:
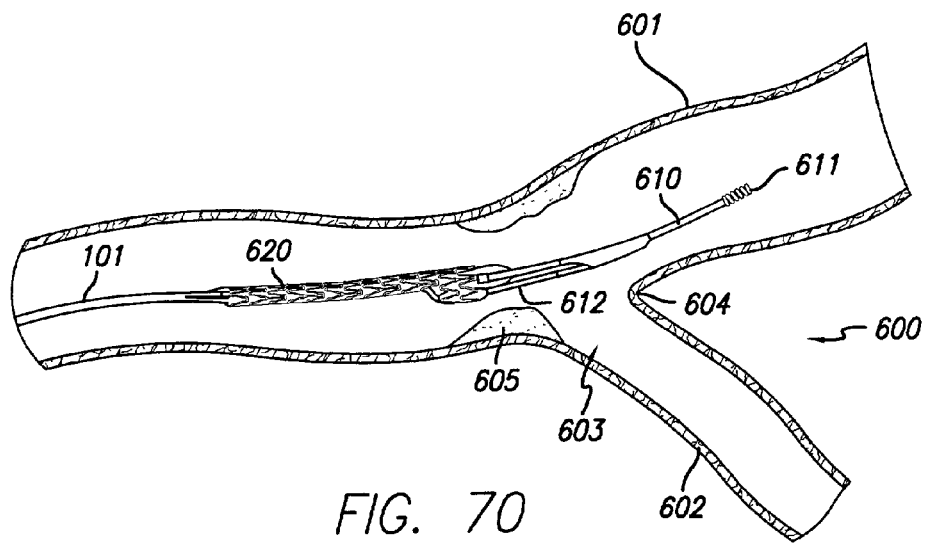
FIGS. 70-74 are elevational views depicting the catheter assembly and stent showing the sequence of advancing the catheter into the vascular system and implanting the stent in the bifurcated vessel.
Figure 71:
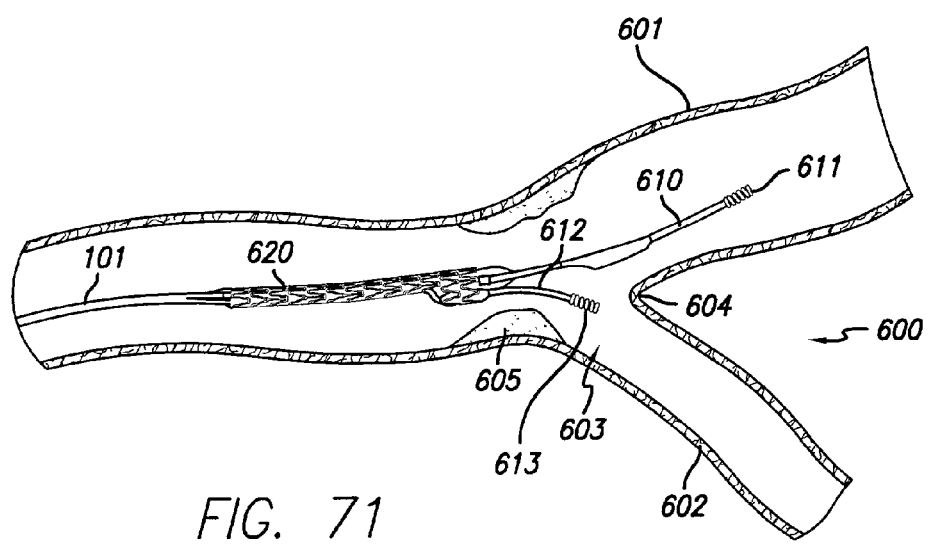

In another embodiment of the bifurcated catheter assembly, the long tip contains a slit in the distal section and also is configured such that the inner diameter of the lumen of the long tip is allowed to expand when two guide wires are advanced simultaneously therethrough. In this embodiment, as shown in FIGS. 62 and 63, the long balloon 570 is positioned adjacent short balloon 571 with the stent (not shown) mounted thereon. A long tip 572 extends from the short balloon and a short tip 573 extends from the long balloon 570. The long tip has an expandable section 574 that is capable of expanding when more than one guide wire is advanced therethrough. The expandable section 574 also has a slit 575 for receiving the Rx guide wire 578. An Rx guide wire lumen extends through the long balloon and the short tip and carries the Rx guide wire 578. An OTW guide wire lumen 577 extends through the short balloon and the long tip 572 and extends all the way to the distal end of the long tip. The Rx guide wire 578 extends distally through the Rx guide wire lumen and exits the short tip and then enters the distal section of the long slit 575. The Rx guide wire exits the long tip and continues distally through the anatomy. During delivery of the stent, the catheter assembly is advanced over the Rx guide wire until it is positioned at the bifurcation. Before the tips are uncoupled, the OTW guide wire 579 is advanced distally through the long tip 572 which will expand upon advancement of the OTW guide wire into the distal and diseased anatomy. The expandable section 574 of the long tip is formed of a material that will easily expand as the OTW guide wire 579 advances through the section in a side-by-side relationship with the Rx guide wire 578, and it will contract after the guide wires are pulled back through the section. The expandable section 574 may have numerous small slits in it, made by a laser for example, to enhance expandability. The expandable section should be formed from an elastomeric material known in the art. After the OTW guide wire is advanced distally through the expandable section, the Rx guide wire 578 is withdrawn proximally through the expandable section and out of slit 575 to uncouple the long balloon from the short balloon. Thereafter, the Rx guide wire is advanced distally and the catheter assembly is advanced over the guide wires to further position the stent for implanting at the bifurcation as previously described.

In FIGS. 51-63, the joining wire (whether in Rx or OTW guide wire or joining wire) is not bent as shown in the drawings. Rather, the joining wire should be substantially straight (or just slightly curved) and the angle between the coupler and the joining tip should be less than about 10° for optional performance in smoothly tracking through the vascular system. The drawings are illustrations only, and it is preferred that the joining wires be generally straight.

It may be advantageous to provide a catheter assembly that is capable of inflating the expandable portions or balloons either simultaneously or independently. For example, it may be advantageous to partially inflate the balloon in the main vessel and fully inflate the balloon in the side branch vessel to avoid plaque shifting or to make sure the stent opening to the side branch vessel is fully opened. The present invention catheter assembly provides for independent balloon inflation and is shown in FIGS. 64-67. The reference numbers are primed to indicate like structure shown in FIG. 29-33. The description of the catheter assembly set forth for FIGS. 29-33 is essentially the same as for FIGS. 64-67 except for the independent inflation lumen and associated structure of the latter drawings.

In keeping with the invention, as shown in FIGS. 64-67, the catheter assembly 140' includes a proximal shaft section 144', an intermediate shaft section 158', and a multifurcated distal shaft section 148 connected together as previously disclosed. Adapter 169' on the proximal end of the catheter assembly has a fifth inflation lumen 190' that extends through first inflation lumen 146' in the proximal shaft section 144'. Fifth inflation lumen 190' extends distally from the adapter, through proximal shaft section 144', through intermediate shaft section 158' and fourth inflation lumen 160', and terminates at the distal end of the intermediate or mid-shaft section 158'. The distal end 191' of the fifth inflation lumen extends into and is in fluid communication with second inflation lumen 154' which extends into first branch 150'. Alternatively, (not shown) the distal end 191' of the fifth inflation lumen can extend into and be in fluid communication with the third inflation lumen 156' which extends into the second branch 152'.

With the distal end 191' of the fifth inflation lumen connected to the second inflation lumen 154', independent balloon inflation is easily achieved by injecting inflation fluid from one source (usually an indeflator) through first proximal port 192' to inflate first balloon 166', and injecting inflation fluid from a second source through second proximal port 193' to inflate second balloon 168'. The balloons 192' and 193' be inflated independently at any pressure or simultaneously at equal pressure.

The delivery of the catheter assembly 140' through the vascular system over the Rx guide wire 194' and the OTW guide wire 180' is substantially the same as previously described for FIGS. 29-33.

In another embodiment of the stent of the invention, as shown in FIGS. 68A, 68B and 69, stent 620 has a distal end 621 and a proximal end 622. There is a longitudinal axis 623 extending through the longitudinal center of the stent. The stent has a first delivery diameter 624 when the stent is mounted on a catheter (if balloon expandable) or mounted within a catheter or retained thereon by other means (if the stent is self-expanding such as with a nitinol stent). As will be seen, the stent has a second implanted diameter when it is implanted in a vessel, such as a coronary artery. The stent of this embodiment has first rings 626 that are configured to be crimpable so that the stent can be crimped to its first delivery diameter, and expandable so that the stent can be expanded and implanted in a vessel. The stent also has one or more second rings 627 that are also crimpable and expandable and generally form the trap door section 628. Further, one or more distal end rings 629 can form the trap door section as well. In order to facilitate crimping the stent onto the catheter or expanding the stent in a vessel, the first rings and second rings are comprised of undulations or valleys 632 and peaks 633. The valleys and peaks will expand or contract as necessary to achieve the purpose of delivering and implanting the stent. The first rings and second rings are interconnected by links 634 that can have any configuration such as linear, non-linear, curved, or a combination of curved and linear configurations. As shown for example in FIG. 68B, the stent can be said to have U-shaped portions 645, Y-shaped portions 646, and W-shaped portions 647. While the rings are intended to be closed rings without any breaks or gaps, it facilitates discussion of the stent by referring to the U-shaped, Y-shaped and W-shaped portions.

Figure 72:
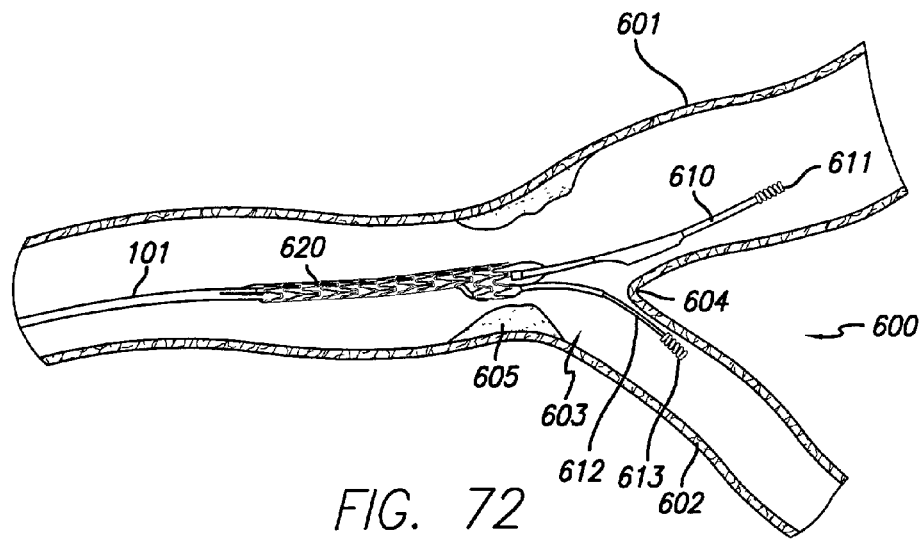
Figure 73:
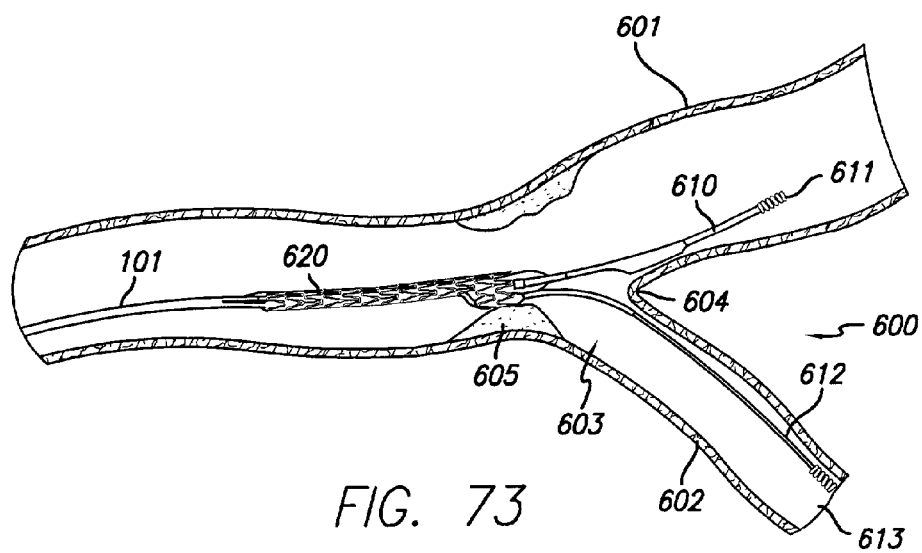
Figure 74:
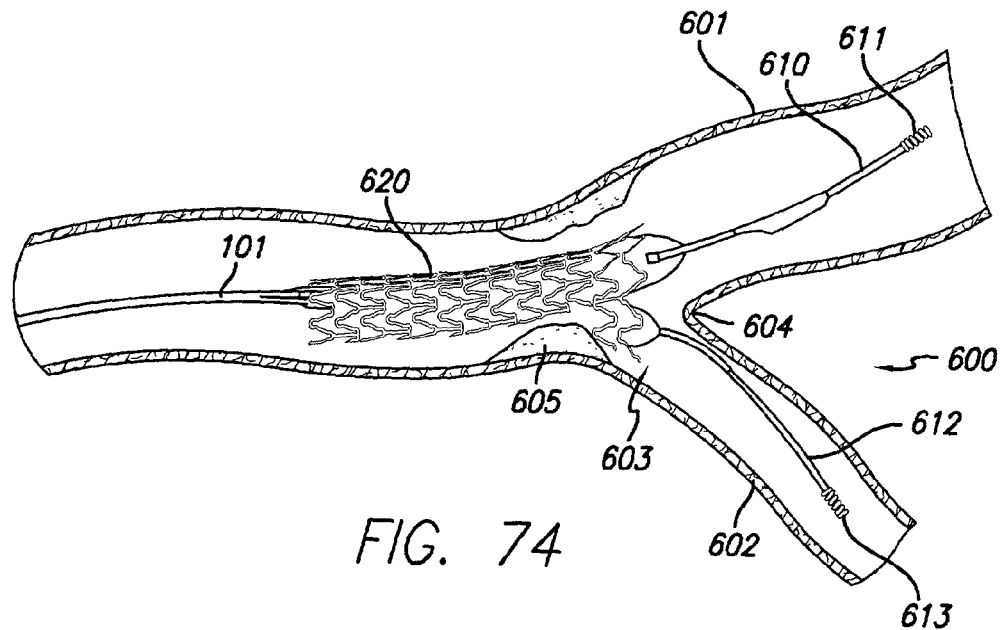
Figure 75A:
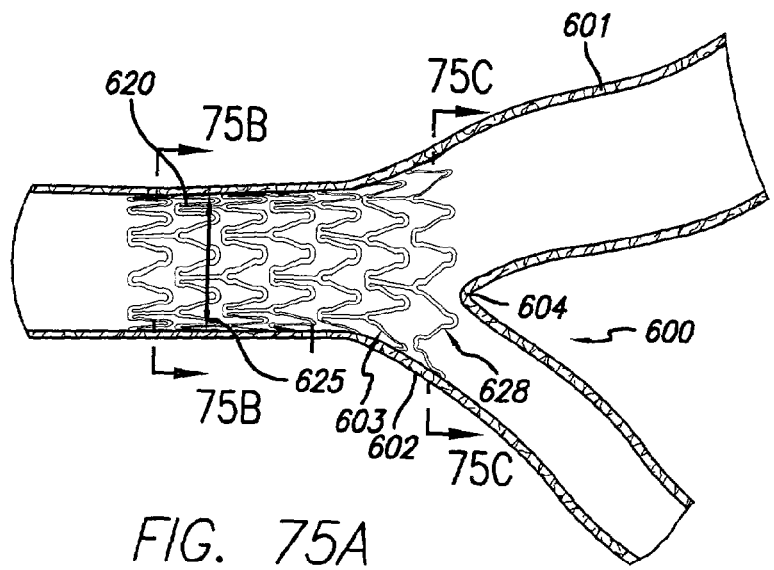
FIG. 75A is elevational views of a bifurcated vessel depicting the stent of the present invention implanted in the main vessel proximal to the bifurcation and the trap door portion of the stent apposing the opening to the side branch vessel.
Figure 75B:
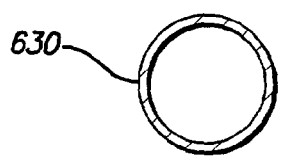
FIG. 75B is a cross-sectional view taken along lines 75B-75B showing the proximal end of the implanted stent having a substantially circular cross-section.
Figure 75C:
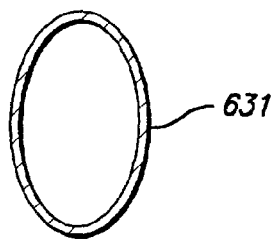
FIG. 75C is a cross-sectional view taken along lines 75C-75C depicting the distal end of the implanted stent having a substantially elliptical cross-section.
Figures 76, 77:
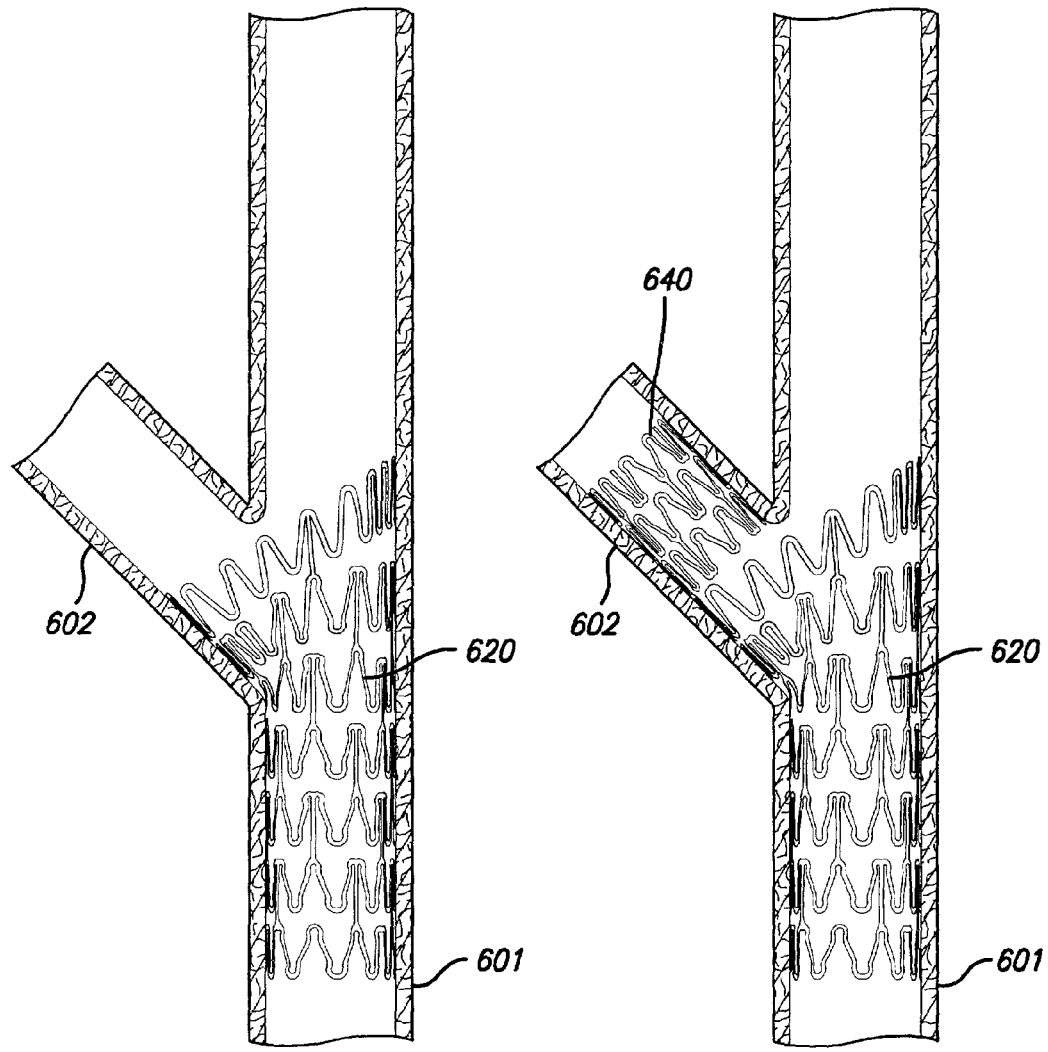
FIGS. 76-77 are elevational views of a bifurcated vessel depicting the stent of the present invention implanted in the main vessel proximal to the bifurcation and the trap door portion of the stent apposing the opening to the side branch vessel.

In keeping with the embodiment of the stent shown in FIGS. 68A-69, the method of implanting the stent 620 is shown in FIGS. 70-77. Stent 620 is particularly useful in stenting a bifurcated vessel where there is very little or no plaque build-up distal to the side branch vessel. For this reason, there would be no reason to stent the portion of the main vessel that is distal to the side branch vessel. Accordingly, the stent and the delivery catheter on which it is mounted is configured to stent that portion of the main vessel that is proximal to the side branch vessel and to stent the opening to the side branch vessel. Thus, as shown in FIGS. 70-77, the main vessel 601 and the side branch vessel 602 form a junction which is defined by the opening to the side branch vessel 603. The carina 304 defines the junction between the side branch vessel and the main vessel. In keeping with the invention, the catheter assembly 101 or 140 (as previously referred to herein) is advanced through a guiding catheter (not shown) in a known manner. Once the distal end 102 of the catheter reaches the ostium to the coronary arteries, the Rx guide wire 610 is advanced distally into the coronary arteries (or any other bifurcated vessel) so that the Rx guide wire distal end 611 extends past the opening to the side branch vessel 603. (In most cases, the main vessel will have been dilated in a known manner prior to delivery of the trap door stent. In these cases, the Rx guide wire will have been left in place across and distal to the target site prior to loading the catheter assembly onto the Rx guide wire for advancement to the target site.) After the distal end of the Rx guide wire is advanced into the main vessel past the opening to the side branch vessel, the catheter is advanced over the Rx guide wire so that the catheter distal end 102 is just proximal to the opening to the side branch vessel. Up to this point in time, the OTW guide wire 312 (or mandrel) remains within the catheter and within coupler 119 keeping the tips and balloons joined as previously described. As shown for example in FIG. 71, the OTW guide wire 612 next is withdrawn proximally so that the OTW guide wire distal end 613 is removed from the coupler blind lumen 121. As shown in FIG. 72, the OTW guide wire next is advanced distally into the side branch vessel 602, extending past the opening to the side branch vessel 303 and advancing distally into the vessel for a distance as shown in FIG. 73. Once the Rx guide wire 610 is in position in the main vessel, and the OTW guide wire 312 is in position in the side branch vessel, this will have a tendency to impart a slight separation between the long balloon 117 and the short balloon 129. As shown in FIG. 74, the catheter assembly 101 is advanced distally over the Rx guide wire and the OTW guide wire, and, as the assembly is further advanced, the long balloon 117 continues to try to separate from the short balloon 129 as each advances into the main vessel 601 and the side branch vessel 602 respectively. As the assembly continues to advance distally, it will reach the point where the distal end 621 of stent 620 is adjacent the opening to the side branch vessel 603 and will press against the carina 604. At this point, the catheter assembly can no longer be advanced distally since the stent is now pushing up against the opening to the side branch vessel. The long balloon 117 and the short balloon 129 are next inflated simultaneously to expand the stent into the main vessel and into the opening to the side branch vessel. As shown in FIG. 75A, the first rings 626 expand into contact with that portion of the main vessel that is proximal to the opening to the side branch vessel. The trap door section 628 having second ring 627 and distal end ring 629 expand into contact with the opening into the side branch vessel and span across the main vessel as well. As shown in FIGS. 75B and 75C, the proximal end of the expanded stent 620 has a substantially circular cross-section 630 while the distal end of the stent has a substantially elliptical cross-section 631 as shown in FIG. 75C. The implanted stent is depicted in a different bifurcated vessel as shown in FIG. 76. Further, should it be necessary to stent the side-branch vessel, the second stent 640 can be inserted through the implanted stent 620 and implanted in the side branch vessel so that it substantially abuts distal end ring 629.

While particular forms of the invention have been illustrated and described, it will be apparent to those skilled in the art that various modifications can be made without departing from the scope of the invention. Accordingly, it is not intended that the invention be limited except by the appended claims.

What is claimed:

1. A method for treating the proximal portion of a main vessel and the opening of a side branch vessel at a bifurcation, comprising:
   providing a stent having a plurality of rings being connected by links, each ring having a plurality of first peaks and second peaks, and each link having a link distal end connected to a valley and a link proximal end connected to the second peak, the stent having a single distal opening;
   mounting the stent on a catheter having a long balloon and a short balloon wherein the long balloon and short balloon are positioned side by side within the stent adjacent the stent distal end and both the long balloon and short balloon extend through the single distal opening;
   advancing the catheter and stent over an RX guide wire while an OTW guide wire is carried by the catheter to the target site;
   advancing the catheter and stent through the vascular system to a position wherein at least some of the first peaks are aligned with the opening to the side branch vessel, and no portion of the stent is distal to the opening;
   inflating the long balloon and the short balloon to radially expand the stent so that at least some of the rings appose and contact the main vessel proximal to the bifurcation and the at least some of the first peaks flare radially outwardly into contact with the opening to the side branch vessel and extend into and contact the opening of the side branch vessel so that the opening to the side branch vessel is not blocked by any portion of the stent; and
   deflating the long balloon and the short balloon and withdrawing the catheter from the vascular system.

2. The method of claim 1, wherein the at least some of the first peaks form a substantially elliptical shape when expanded to appose and contact the opening to the side branch vessel.

3. The method of claim 1, wherein the catheter includes a rapid exchange (RX) guide wire passageway for receiving an RX guide wire and an over-the-wire (OTW) guide wire passageway for receiving an OTW guide wire so that as the stent is positioned at the bifurcation, the catheter is slidably advancing over the RX guide wire and the OTW guide wire.

4. The method of claim 3, wherein as the catheter is advanced through the vascular system, the catheter slides over the RX guide wire positioned in the main vessel while a distal end of the OTW is positioned within a blind lumen.

5. The method of claim 4, wherein after the catheter is positioned proximal to the bifurcation, the OTW guide wire is withdrawn from the blind lumen and advanced into the side branch vessel.

6. The method of claim 5, wherein after the OTW guide wire is advanced into the side branch vessel, the catheter is advanced distally over the RX guide wire and the OTW guide wire to position the stent at the bifurcation.

* * * * *